US012661647B2

(12) United States Patent
Khurana et al.

(10) Patent No.: US 12,661,647 B2
(45) Date of Patent: Jun. 23, 2026

(54) METHODS FOR ENCLOSING AND ANALYZING A CELL IN A FLUIDIC DEVICE

(71) Applicant: Cellanome, Inc., Foster City, CA (US)

(72) Inventors: Tarun Kumar Khurana, Palo Alto, CA (US); Ali Agah, Palo Alto, CA (US); Yir-Shyuan Wu, Palo Alto, CA (US); Pier Federico Gherardini, Palo Alto, CA (US); Filiz Gorpe Yasar, Palo Alto, CA (US)

(73) Assignee: Cellanome, Inc., Foster City, CA (US)

( * ) Notice: Subject to any disclaimer, the term of this patent is extended or adjusted under 35 U.S.C. 154(b) by 0 days.

(21) Appl. No.: 19/278,614

(22) Filed: Jul. 23, 2025

(65) Prior Publication Data

US 2025/0345792 A1 Nov. 13, 2025

Related U.S. Application Data

(63) Continuation of application No. 18/891,555, filed on Sep. 20, 2024, now abandoned, which is a continuation of application No. PCT/US2023/015806, filed on Mar. 21, 2023.

(60) Provisional application No. 63/322,601, filed on Mar. 22, 2022.

(51) Int. Cl.

| | |
|---|---|
| ***C12Q 1/68*** | (2018.01) |
| ***B01L 3/00*** | (2006.01) |
| ***C12Q 1/6869*** | (2018.01) |
| ***C12Q 1/6874*** | (2018.01) |
| ***G01N 33/543*** | (2006.01) |
| ***G01N 33/68*** | (2006.01) |

(52) U.S. Cl.

CPC ... *B01L 3/502715* (2013.01); *B01L 3/502707* (2013.01); *B01L 3/502761* (2013.01); *C12Q 1/6869* (2013.01); *C12Q 1/6874* (2013.01); *G01N 33/54386* (2013.01); *G01N 33/6842* (2013.01); *B01L 2200/0647* (2013.01); *B01L 2200/12* (2013.01); *B01L 2300/0663* (2013.01); *B01L 2300/0883* (2013.01); *B01L 2300/12* (2013.01); *B01L 2300/163* (2013.01); *B01L 2300/18* (2013.01); *C12Q 2600/158* (2013.01); *G01N 2570/00* (2013.01)

(58) Field of Classification Search

CPC ........................................................ C12Q 1/02

See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,800,159 | A | 1/1989 | Mullis et al. |
| 4,942,124 | A | 7/1990 | Church |
| 4,965,188 | A | 10/1990 | Mullis et al. |
| 5,002,867 | A | 3/1991 | Macevicz |
| 5,126,022 | A | 6/1992 | Soane et al. |
| 5,168,038 | A | 12/1992 | Tecott et al. |
| 5,210,015 | A | 5/1993 | Gelfand et al. |
| 5,367,066 | A | 11/1994 | Urdea et al. |
| 5,399,491 | A | 3/1995 | Kacian et al. |
| 5,498,392 | A | 3/1996 | Wilding et al. |
| 5,587,128 | A | 12/1996 | Wilding et al. |
| 5,635,400 | A | 6/1997 | Brenner |
| 5,641,658 | A | 6/1997 | Adams et al. |
| 5,700,642 | A | 12/1997 | Monforte et al. |
| 5,739,386 | A | 4/1998 | Holmes |
| 5,830,655 | A | 11/1998 | Monforte et al. |
| 5,854,033 | A | 12/1998 | Lizardi |
| 5,858,195 | A | 1/1999 | Ramsey |
| 5,925,517 | A | 7/1999 | Tyagi et al. |
| 5,981,179 | A | 11/1999 | Lorinez et al. |
| 6,001,229 | A | 12/1999 | Ramsey |
| 6,010,607 | A | 1/2000 | Ramsey |
| 6,033,546 | A | 3/2000 | Ramsey |
| 6,054,034 | A | 4/2000 | Soane et al. |
| 6,060,288 | A | 5/2000 | Adams et al. |
| 6,063,339 | A | 5/2000 | Tisone et al. |
| 6,090,592 | A | 7/2000 | Adams et al. |
| 6,174,670 | B1 | 1/2001 | Wittwer et al. |
| 6,176,962 | B1 | 1/2001 | Soane et al. |

(Continued)

FOREIGN PATENT DOCUMENTS

| | | |
|---|---|---|
| CA | 3030558 A1 | 1/2018 |
| CA | 3134848 A1 | 6/2021 |

(Continued)

OTHER PUBLICATIONS

Abraham, Vivek C. et al. Application of a high-content multiparameter cytotoxicity assay to prioritize compounds based on toxicity potential in humans. SLAS Discovery 13(6):527-537 (2008).

Adessi, Celine. et al. Solid phase DNA amplification: characterisation of primer attachment and amplification mechanisms. Nucleic acids research 28(20):E87, 1-8 (2000).

Adey, Andrew C. Tagmentation-based single-cell genomics. Genome research 31(10): 1693-1705 (2021).

Albrecht et al, "Photo- and electropatterning of hydrogel-encapsulated living cell arrays," LabChip, 5: 111-118 (2005).

Allen, Elizabeth S. et al. Autologous lymphapheresis for the production of chimeric antigen receptor T cells. Transfusion 57(5):1133-1141 (2017).

(Continued)

*Primary Examiner* — Kenneth R Horlick

(74) *Attorney, Agent, or Firm* — Wilson Sonsini Goodrich & Rosati

(57) ABSTRACT

Described herein are systems and methods for analyzing biological samples (e.g., cells), including a method comprising (a) introducing a first cell into a fluidic device, (b) introducing a second cell into the fluidic device, (c) introducing a polymer precursor into the fluidic device, (d) using a virtual photomask to selectively apply light to the fluidic device to polymerize the polymer precursor, thereby selectively enclosing the first cell and the second cell in the fluidic device.

46 Claims, 24 Drawing Sheets

(56) References Cited

U.S. PATENT DOCUMENTS 6,300,070 B1 10/2001 Boles et al.
6,312,134 B1 11/2001 Jain et al.
6,399,952 B1 6/2002 Maher et al.
6,514,706 B1 2/2003 Von Kalle et al.
6,569,627 B2 5/2003 Wittwer et al.
6,613,525 B2 9/2003 Nelson et al.
6,787,308 B2 9/2004 Balasubramanian et al.
6,803,019 B1 10/2004 Bjornson et al.
6,838,156 B1 1/2005 Neyer et al.
6,908,594 B1 6/2005 Schaevitz et al.
6,960,437 B2 11/2005 Enzelberger et al.
7,097,809 B2 8/2006 Van et al.
7,276,381 B2 10/2007 Kitagawa
7,425,431 B2 9/2008 Church et al.
7,537,897 B2 5/2009 Brenner et al.
7,666,598 B2 2/2010 Piepenburg et al.
7,695,954 B2 4/2010 Bachman et al.
7,759,119 B2 7/2010 Allbritton et al.
7,763,427 B2 7/2010 Piepenburg et al.
7,771,949 B2 8/2010 Kramer
7,790,418 B2 9/2010 Mayer
7,824,854 B2 11/2010 Arai et al.
7,951,580 B2 5/2011 Li et al.
7,985,565 B2 7/2011 Kawashima et al.
8,173,080 B2 5/2012 Lebl et al.
8,426,134 B2 4/2013 Piepenburg et al.
8,652,810 B2 2/2014 Adessi et al.
8,691,274 B2 4/2014 Xu et al.
8,778,849 B2 7/2014 Bowen et al.
8,822,647 B2 9/2014 Jensen
8,900,828 B2 12/2014 Smith et al.
8,906,684 B2 12/2014 Bhatia et al.
8,921,073 B2 12/2014 Reed et al.
9,057,097 B2 6/2015 Piepenburg et al.
9,068,155 B2 6/2015 Allbritton et al.
9,085,801 B2 7/2015 Grunenwald et al.
9,115,396 B2 8/2015 Grunenwald et al.
9,169,513 B2 10/2015 Shen et al.
9,249,461 B2 2/2016 Hinz et al.
9,309,558 B2 4/2016 Li et al.
9,367,049 B2 6/2016 Jariwala et al.
9,416,415 B2 8/2016 Ronaghi et al.
9,476,080 B2 10/2016 Li et al.
9,487,745 B2 11/2016 Wang et al.
9,512,422 B2 12/2016 Barnard et al.
9,555,007 B2 1/2017 Ma et al.
9,561,622 B2 2/2017 Das et al.
9,593,328 B2 3/2017 Kawashima et al.
9,593,365 B2 3/2017 Frisen et al.
9,631,092 B2 4/2017 Bowman et al.
9,642,914 B2 5/2017 Alsberg et al.
9,758,578 B2 9/2017 Fujino et al.
9,765,291 B2 9/2017 Allbritton et al.
9,777,326 B2 10/2017 Ronaghi et al.
9,902,951 B2 2/2018 Kawashima et al.
9,963,666 B2 5/2018 Allbritton et al.
10,011,872 B1 7/2018 Belgrader et al.
10,072,257 B2 9/2018 Bhatia et al.
10,260,039 B2 4/2019 Bhatia et al.
10,351,819 B2 7/2019 Hribar et al.
10,385,335 B2 8/2019 McGall
10,423,071 B2 9/2019 Hribar
10,464,307 B2 11/2019 Chung et al.
10,570,447 B2 2/2020 Ronaghi et al.
10,661,275 B2 5/2020 Levner et al.
10,774,374 B2 9/2020 Frisen et al.
11,003,071 B2 5/2021 Hribar et al.
11,046,926 B2 6/2021 Allbritton et al.
11,065,620 B2 7/2021 Levner et al.
11,085,036 B2 8/2021 Norberg et al.
11,137,385 B2 10/2021 Khurana et al.
11,142,787 B2 10/2021 Hosokawa et al.
11,143,638 B2 10/2021 Khurana et al.
11,180,752 B2 11/2021 Wu et al.
RE48,913 E 2/2022 Fodor et al.
11,299,774 B2 4/2022 Frisen et al.
11,319,534 B2 5/2022 Steemers et al.
11,390,912 B2 7/2022 Frisen et al.
11,554,370 B2 1/2023 Khurana et al.
11,612,890 B2 3/2023 Kurz et al.
12,030,047 B2 7/2024 Khurana et al.
12,151,242 B2 11/2024 Khurana et al.
12,303,892 B2 5/2025 Khurana et al.
12,313,624 B2 5/2025 Oliner et al.
12,440,837 B2 * 10/2025 Khurana ............ G01N 33/6842
2002/0117517 A1 8/2002 Unger et al.
2003/0096239 A1 5/2003 Gunderson et al.
2003/0175824 A1 9/2003 Pishko et al.
2003/0186226 A1 10/2003 Brennan et al.
2004/0106728 A1 6/2004 McGall et al.
2004/0219214 A1 11/2004 Gravett et al.
2005/0084912 A1 4/2005 Poponin
2005/0208465 A1 9/2005 Arai et al.
2005/0250147 A1 11/2005 Macevicz
2005/0282156 A1 12/2005 Rava et al.
2006/0110722 A1 5/2006 Beebe et al.
2006/0263263 A1 11/2006 Shimizu
2008/0193536 A1 8/2008 Khademhosseini et al.
2010/0292931 A1 11/2010 Wang et al.
2010/0309304 A1 12/2010 Chalmond et al.
2012/0129719 A1 5/2012 Quake et al.
2012/0148552 A1 6/2012 Jensen
2012/0202263 A1 8/2012 Blakely et al.
2012/0270209 A1 10/2012 Shah et al.
2012/0316086 A1 12/2012 Lin et al.
2013/0123988 A1 5/2013 Jariwala et al.
2013/0288368 A1 10/2013 June et al.
2013/0344601 A1 12/2013 Soman et al.
2014/0080717 A1 3/2014 Li et al.
2014/0134142 A1 5/2014 Smith et al.
2014/0163736 A1 6/2014 Azizian et al.
2014/0235468 A1 8/2014 Cheng et al.
2014/0314795 A1 10/2014 Riddell et al.
2014/0378322 A1 12/2014 Hindson et al.
2015/0119280 A1 4/2015 Srinivas et al.
2015/0159204 A1 6/2015 Drmanac et al.
2015/0175734 A1 6/2015 Light et al.
2015/0267251 A1 9/2015 Cai et al.
2016/0060621 A1 3/2016 Agresti et al.
2016/0138086 A1 5/2016 Seelig et al.
2016/0177030 A1 6/2016 Sugiura et al.
2016/0208308 A1 7/2016 Cohen et al.
2016/0221262 A1 8/2016 Das et al.
2016/0375143 A1 12/2016 Gunatillake et al.
2017/0087766 A1 3/2017 Chung et al.
2017/0312368 A1 11/2017 Ashley et al.
2018/0030515 A1 2/2018 Regev et al.
2018/0066299 A1 3/2018 Kim et al.
2018/0113114 A1 4/2018 Lütolf et al.
2018/0292428 A1 10/2018 Murayama et al.
2018/0320224 A1 11/2018 Gaublomme et al.
2019/0017107 A1 1/2019 Light et al.
2019/0062835 A1 2/2019 López Escámez et al.
2019/0106667 A1 4/2019 Hribar
2019/0127782 A1 5/2019 Regev et al.
2019/0136170 A1 5/2019 Allbritton et al.
2019/0256817 A1 8/2019 Gebhart et al.
2019/0345488 A1 11/2019 Soumillon et al.
2019/0360121 A1 11/2019 Fan et al.
2020/0080046 A1 3/2020 Gebhart et al.
2020/0080060 A1 3/2020 Matheu et al.
2020/0122137 A1 4/2020 Jung et al.
2020/0139696 A1 5/2020 Chung et al.
2020/0181604 A1 6/2020 Jacobson et al.
2020/0216895 A1 7/2020 Khurana et al.
2020/0325467 A1 10/2020 Mather et al.
2020/0362334 A1 11/2020 Regev et al.
2020/0399428 A1 12/2020 Kleine-Brüggeney et al.
2021/0018503 A1 1/2021 Varadarajan et al.
2021/0019287 A1 1/2021 Prasad et al.
2021/0079386 A1 3/2021 Kaper et al.
2021/0123040 A1 4/2021 Macosko et al.
2021/0162408 A1 6/2021 Sabaawy et al.
2021/0172856 A1 6/2021 Zhao

(56) References Cited

U.S. PATENT DOCUMENTS

| | | | |
|---|---|---|---|
| 2021/0246495 | A1 | 8/2021 | Hosokawa et al. |
| 2021/0253625 | A1 | 8/2021 | Kazakov et al. |
| 2021/0285036 | A1 | 9/2021 | Yin et al. |
| 2021/0349075 | A1 | 11/2021 | Bronevetsky et al. |
| 2021/0405019 | A1 | 12/2021 | Khurana et al. |
| 2022/0003728 | A1 | 1/2022 | Khurana et al. |
| 2022/0010367 | A1 | 1/2022 | Ramachandran Iyer et al. |
| 2022/0025447 | A1 | 1/2022 | Tentori et al. |
| 2022/0033893 | A1 | 2/2022 | Lan et al. |
| 2022/0034867 | A1 | 2/2022 | Butler et al. |
| 2022/0143603 | A1 | 5/2022 | Khurana et al. |
| 2022/0145361 | A1 | 5/2022 | Frenz et al. |
| 2022/0160445 | A1 | 5/2022 | Meglan et al. |
| 2022/0163513 | A1 | 5/2022 | Fowler et al. |
| 2022/0219170 | A1 | 7/2022 | Khurana et al. |
| 2022/0226820 | A1 | 7/2022 | Khurana et al. |
| 2022/0243269 | A1 | 8/2022 | Khurana et al. |
| 2023/0001413 | A1 | 1/2023 | Khurana et al. |
| 2023/0348974 | A1 | 11/2023 | Khurana et al. |
| 2024/0198332 | A1 | 6/2024 | Khurana et al. |
| 2024/0301465 | A1 | 9/2024 | Gherardini et al. |
| 2025/0027133 | A1 | 1/2025 | Khurana et al. |
| 2025/0050301 | A1 | 2/2025 | Macevicz et al. |
| 2025/0102419 | A1 | 3/2025 | Khurana et al. |
| 2025/0149119 | A1 | 5/2025 | Khurana |
| 2025/0164496 | A1 | 5/2025 | Gherardini et al. |
| 2026/0001076 | A1 | 1/2026 | Khurana et al. |

FOREIGN PATENT DOCUMENTS

| | | | |
|---|---|---|---|
| DE | 102015001998 | B3 | 2/2016 |
| EP | 0799897 | A1 | 10/1997 |
| EP | 1488006 | B1 | 5/2008 |
| EP | 3450471 | A1 | 3/2019 |
| EP | 3145689 | B1 | 1/2020 |
| EP | 3450471 | B1 | 12/2020 |
| EP | 2784151 | B1 | 3/2021 |
| EP | 3752634 | B1 | 8/2022 |
| EP | 3484620 | B1 | 3/2024 |
| EP | 3836887 | B1 | 7/2024 |
| GB | 2315700 | A | 2/1998 |
| IL | 308886 | A | 1/2024 |
| JP | H04262799 | A | 9/1992 |
| KR | 20210103010 | A | 8/2021 |
| NL | 2017834 | | 5/2018 |
| WO | WO-9844151 | A1 | 10/1998 |
| WO | WO-9919717 | A1 | 4/1999 |
| WO | WO-0023458 | A1 | 4/2000 |
| WO | WO-0224322 | A2 | 3/2002 |
| WO | WO-2004006840 | A2 | 1/2004 |
| WO | WO-2005074569 | A2 | 8/2005 |
| WO | WO-2006125458 | A1 | 11/2006 |
| WO | WO-2010132795 | A2 | 11/2010 |
| WO | WO-2012064172 | A1 | 5/2012 |
| WO | WO-2014031997 | A1 | 2/2014 |
| WO | WO-2015010019 | A1 | 1/2015 |
| WO | WO-2015164212 | A1 | 10/2015 |
| WO | WO-2015179572 | A1 | 11/2015 |
| WO | WO-2016138496 | A1 | 9/2016 |
| WO | WO-2017048993 | A1 | 3/2017 |
| WO | WO-2017075265 | A1 | 5/2017 |
| WO | WO-2017151582 | A1 | 9/2017 |
| WO | WO-2018013646 | A1 | 1/2018 |
| WO | WO-2018097715 | A1 | 5/2018 |
| WO | WO-2018097950 | A1 | 5/2018 |
| WO | WO-2018172726 | A1 | 9/2018 |
| WO | WO-2019028047 | A1 | 2/2019 |
| WO | WO-2019028166 | A1 | 2/2019 |
| WO | WO-2019157529 | A1 | 8/2019 |
| WO | WO-2019203728 | A1 | 10/2019 |
| WO | WO-2020047002 | A1 | 3/2020 |
| WO | WO-2020120442 | A2 | 6/2020 |
| WO | WO-2020190509 | A1 | 9/2020 |
| WO | WO-2020255108 | A1 | 12/2020 |
| WO | WO-2021108499 | A1 | 6/2021 |
| WO | WO-2021122579 | A1 | 6/2021 |
| WO | WO-2021155057 | A1 | 8/2021 |
| WO | WO-2021163374 | A2 | 8/2021 |
| WO | WO-2022013094 | A1 | 1/2022 |
| WO | WO-2022015600 | A2 | 1/2022 |
| WO | WO-2022069993 | A1 | 4/2022 |
| WO | WO-2022096294 | A2 | 5/2022 |
| WO | WO-2022150659 | | 7/2022 |
| WO | WO-2022178095 | A1 | 8/2022 |
| WO | WO-2022261507 | | 12/2022 |
| WO | WO-2023183327 | A1 | 9/2023 |
| WO | WO-2023194435 | A1 | 10/2023 |
| WO | WO-2023196603 | A1 | 10/2023 |
| WO | WO-2023225366 | A1 | 11/2023 |
| WO | WO-2023240207 | A1 | 12/2023 |
| WO | WO-2024020398 | A1 | 1/2024 |
| WO | WO-2024092056 | A1 | 5/2024 |
| WO | WO-2024145393 | A1 | 7/2024 |
| WO | WO-2025072571 | A1 | 4/2025 |
| WO | WO-2025111469 | A1 | 5/2025 |
| WO | WO-2025128916 | A1 | 6/2025 |

OTHER PUBLICATIONS

Altschuler, Steven J, and Lani F Wu. Cellular heterogeneity: do differences make a difference? Cell 141(4):559-563 (2010).

Anagnostidis, Vasileios. et al. Deep learning guided image-based droplet sorting for on-demand selection and analysis of single cells and 3D cell cultures. Lab on a Chip 20(5):889-900 (2020).

Anderson, Rhona. Multiplex fluorescence in situ hybridization (M-FISH). Fluorescence in situ Hybridization (FISH) Protocols and Applications 659:83-97 (2010).

Annabi, Nasim. et al. Controlling the porosity and microarchitecture of hydrogels for tissue engineering. Tissue Engineering: Part B 16(4):371-383 (2010).

Ardila, Federico, and Richard P. Stanley. Tilings. Mathematical Entertainments 32:32-43 (2010).

Attayek, Peter J. et al. Array-based platform to select, release, and capture Epstein-barr virus-infected cells based on intercellular adhesion. Analytical chemistry 87(24):12281-12289 (2015).

Attayek, Peter J. et al. Identification and isolation of antigen-specific cytotoxic T lymphocytes with an automated microraft sorting system. Integrative Biology 8(12):1208-1220 (2016).

Avishay, Dor M and Kevin M. Tenny. Henry's Law. StatPearls, NCBI Bookshelf (2021).

Barczak, Andrea. et al. Spotted long oligonucleotide arrays for human gene expression analysis. Genome Research 13(7):1775-1785 (2003).

Barrett, David M. et al. Chimeric Antigen Receptor Therapy For Cancer. Annual Review of Medicine 65:333-347 (2014). Published online Nov. 20, 2013.

Basu, Swarna, and Campagnola, Paul J. Enzymatic activity of alkaline phosphatase inside protein and polymer structures fabricated via multiphoton excitation. Biomacromolecules, American Chemical Society 5(2):572-579 (2004).

Bayani, Jane, and Jeremy A Squire. Unit 22.4: Fluorescence in situ Hybridization (FISH). Current Protocols in Cell Biology Supplement 23:22.4, 1-52 (2004).

Beaucage, S L. Strategies in the preparation of DNA oligonucleotide arrays for diagnostic applications. Current medicinal chemistry 8(10):1213-1244 (2001).

Beaucage, Serge L. Strategies in the preparation of DNA oligonucleotide arrays for diagnostic applications. Current medicinal chemistry 8(10):1213-1244 (2001). (Abstract Only).

Beck, Martin. et al. The quantitative proteome of a human cell line. Molecular Systems Biology 7(1):549, 1-8 (2011).

Becker, Holger, and Laurie E Locascio. Polymer microfluidic devices. Talanta 56(2):267-287 (2002).

Ben-Chetrit, Nir. et al. Integrated protein and transcriptome high-throughput spatial profiling. bioRxiv :1-35 (2022).

Bennett, et al. T cell activation could be defined by the expression of CD45RA, CCR7, CD25, PD1 and HLA-DR. Methods in Enzymology 1-13 (2020).

(56) References Cited

OTHER PUBLICATIONS

Bercovici, Nadege. et al. New Methods for Assessing T-Cell Responses. Clinical and Diagnostic Laboratory Immunology 7(6):859-864 (2000).
Biasco, Luca. et al. Analyzing the Genotoxicity of Retroviral Vectors in Hematopoietic Cell Gene Therapy. Molecular Therapy Methods & Clinical Development 8:21-30 (2017).
Bickle, Marc. High Content Screening in Drug Discovery. Technology Development Studio, Max Planck Institute of Molecular Cell Biology and Genetics :1-12 (2010).
Bigfoot Spectral Cell Sorter, High-throughput plate sorting. Invitrogen :1-5 (2021).
Bose, Sayantan. et al. Scalable Microfluidics for Single-cell RNA Printing and Sequencing. Genome Biology 16(1):120, 1-16 (2015).
Boutros, Michael. et al. Microscopy-Based High-Content Screening. Cell 163(6):1314-1325 (2015).
Bradford, Jolene A, and Gayle M. Buller. Dead Cell Stains In Flow Cytometry: A Comprehensive Analysis. Poster presented at Molecular Probes. p. 1 (2009).
Buenrostro, Jason D. et al. Single-cell chromatin accessibility reveals principles of regulatory variation. Nature 523(7561):486-490 (2015).
Burdick et al, "Moving from static to dynamic complexity in hydrogel design," Nature Comm., 3: 1269 (Dec. 11, 2012).
Burgess. Spatial transcriptomics coming of age. Nature Reviews Genetics 20:317 (2019).
Burnham, Mary Rose. et al. Biological functionalization and surface micropatterning of polyacrylamide hydrogels. Biomaterials 27(35):5883-5891 (2006). (Abstract Only).
Cadwell, Cathryn R. et al. Multimodal profiling of single-cell morphology, electrophysiology, and gene expression using Patch-seq. Nature protocols 12(12):2531-2553 (2017).
Cai. Turning single cells into microarrays by super-resolution barcoding. Briefings in Functional Genomics 12(2):75-80 (2012).
Caicedo, Juan C. et al. Applications in image-based profiling of perturbations. Current opinion in biotechnology 39:134-142 (2016).
Caliari, Steven R. et al. A Practical Guide to Hydrogels for Cell Culture. Nature Methods 13(5):405-414 (2016).
Carpenter, Anne E. "Image-based chemical screening." Nature Chemical Biology 3.8 (2007):461-465 (2007).
Cartesian PA Series. Cartesian Technologies a Genomic Solutions Company, 1998. Available at URL:https://www.seaviewsci.com/cartesian/pixsyspa.htm. pp. 1-5.
Cha et al, "Structural reinforcement of cell-laden hydrogels with microfabricated three dimensional scaffolds," Biomaterial Science, 2(5): 703-709 (2014).
Chava, Suresh. et al. Measurement of Natural Killer Cell-Mediated Cytotoxicity and Migration in the Context of Hepatic Tumor Cells. Journal of Visualized Experiments 156:e60714, 1-7 (2020).
Chavey, D. Tilings By Regular Polygons—II: A Catalog of Tilings. Computers & Mathematics with Applications 17(1-3):147-165 (1989).
Chen, A. et al. Vector copy number quality control testing for CAR T-cells: critical validation parameters. Cytotherapy 22(5):S142, 1-1 (2020).
Chen, Ao. et al. Spatiotemporal transcriptomic atlas of mouse organogenesis using DNA nanoball-patterned arrays. Cell 185(10):1777-1792 (2022).
Chen, Ao. et al. Spatiotemporal Transcriptomic Atlas of Mouse Organogenesis2 using DNA Nanoball Patterned Arrays. bioRxiv :1-75 (2021).
Chen, et al. Large field of view-spatially resolved transcriptomics at nanoscale resolution. bioRxiv 2021.01.17.427004; doi: https://doi.org/10.1101/2021.01.17.427004 (2021).
Chen et al.: Rare cell isolation and analysis in microfluidics. Lab Chip14(4):626-645 (Feb. 2014).
Chen, He. et al. Tagmentation on microbeads: restore long-range DNA sequence information using Next Generation Sequencing with library prepared by surface-immobilized transposomes. ACS applied materials and interfaces 10(14):11539-11545 (2018).
Chen, Kok Hao. et al. Spatially resolved, highly multiplexed RNA profiling in single cells. Science 348(6233):aaa6090, 1-15 (2015).
Chen, Minfeng. et al. Comparison of multiple displacement amplification (MDA) and multiple annealing and looping-based amplification cycles (MALBAC) in single-cell sequencing. PLoS One 9(12):e114520, 1-12 (2014).
Chen, Siyuan. et al. Controlling oligonucleotide surface density in light-directed DNA array fabrication. Langmuir 25(11):6570-6575 (2009).
Cheng, Jing, and Larry J. Kricka. Biochip Technology. CRC Press (2001).
Cheng, Jiqiu. et al. Single-cell copy number variation detection. 12(8):R80, 1-14 (2011).
Cho, Chun-Seaok. et al. Seq-Scope: Submicrometer-resolution Spatial Transcriptomics for Single Cell and Subcellular Studies. bioRxiv :1-50 (2021).
Cho, Chun-Seok. et al. Microscopic examination of spatial transcriptome using Seq-Scope. Cell 184(13):3559-3572 (2021).
Choi, Hyun Jo. et al. Micropatterning of biomolecules on glass surfaces modified with various functional groups using photoactivatable biotin. Analytical Biochemistry 341(1):60-66 (2005). (Abstract Only).
Choi, Jane Ru. et al. Recent advances in photo-crosslinkable hydrogels for biomedical applications. BioTechniques 66(1):40-53 (2019).
Conditioning cell culture media. Cell Guidance Systems. Jun. 17, 2020; [retrieved on Sep. 25, 2023]. Available at URL: https://www.cellgs.com/blog/conditioning-cell-culture-media.html pp. 1-5.
Conrad, Christian. et al. Micropilot: automation of fluorescence microscopy-based imaging for systems biology. Nature methods 8(3):246-249 (2011).
Conzone, Samuel D, and Carlo G. Pantanot. Glass Slides to DNA Microarrays. Materials Today 7(3):20-26 (2004).
Co-pending U.S. Appl. No. 19/052,121, inventors Moeinzadeh; Seyedsina et al., filed Feb. 12, 2025.
Cornetta, Kenneth. et al. Meeting FDA Guidance recommendations for replication-competent virus and insertional oncogenesis testing. Molecular Therapy Methods & Clinical Development 28:28-39 (2022).
Corre, Guillaume. et al. Lentiviral Standards to Determine the Sensitivity of Assays That Quantify Lentiviral Vector Copy Numbers and Genomic Insertion Sites in Cells 29(9):536-543 (2022).
Cortes-Llanos, Belen. et al. A technology of a different sort: microraft arrays. Lab on a Chip 21(17):3204-3218 (2021).
Cui, X F. et al. Single-sperm typing: determination of genetic distance between the G gamma-globin and parathyroid hormone loci by using the polymerase chain reaction and allele-specific oligomers. Proceedings of the National Academy of Sciences of the United States of America 86(23):9389-9393 (1989).
Curley et al, "Fabrication of micropatterned hydrogels for neural culture systems using dynamic mask projection photolithography," J. Visualized Experiments, 48: e2636 (2011).
Cuvelier, et al. Micropatterned "adherent/repellent" glass surfaces for studying the spreading kinetics of individual red blood cells onto protein-decorated substrates. Eur Biophys J 32:342-354 (2003).
Dadfar, Seyed Mohammad Mahdi. et al. Site-Specific Surface Functionalization via Microchannel Cantilever Spotting (MuCS): Comparison between Azide-Alkyne and Thiol-Alkyne Click Chemistry Reactions. Small 14(21):1800131, 1-10 (2018).
Danuser, Gaudenz. Computer vision in cell biology. Cell 147(5):973-978 (2011).
Datlinger, Paul. et al. Pooled CRISPR screening with single-cell transcriptome readout. Nature methods 14(3):297-301 (2017).
Deforest, Cole A. and Anseth, Kristi S. Cytocompatible Click-based Hydrogels with Dynamically-Tunable Properties Through Orthogonal Photoconjugation and Photocleavage Reactions. Nature Chemistry. 3(12):925-931 (2011).
Deleye, Lieselot. et al. Performance of four modern whole genome amplification methods for copy number variant detection in single cells. Scientific Reports 7:3422, 1-9 (2017).
Deleye, Lieselot. et al. Whole genome amplification with SurePlex results in better copy number alteration detection using sequencing data compared to the MALBAC method. Scientific Reports 5:11711, 1-13 (2015).

(56) References Cited

OTHER PUBLICATIONS

Delley, Cyrille L, and Adam R Abate. Modular barcode beads for microfluidic single cell genomics. Scientific reports 11(1):10857, 1-9 (2021).
D'Eramo et al, "Microfluidic actuators based on temperature-responsive hydrogels," Microsystems & Nanoengineering, 4: 17069 (2018).
Desfarges, Sébastien, and Angela Ciuffi. Retroviral Integration Site Selection. Viruses 2(1):111-130 (2010).
Devor, Eric J. et al. Strategies for Attaching Oligonucleotides to Solid Supports. Integrated DNA Technologies :1-24 (2005).
Ding et al, "Single-cell RNA sequencing in breast cancer: understanding tumor heterogeneity and paving roads to individualized therapy," Cancer Communications, 40: 329-344 (2020).
Dittrich, Petra, and Norbert Jakubowski. Current trends in single cell analysis. Analytical and Bioanalytical Chemistry 406(27):6957-6961 (2014).
Drury, Jeanie L, and David J Mooney. et al. Hydrogels for Tissue Engineering: Scaffold Design Variables and Applications. Biomaterials 24(24):4337-4351 (2003).
Dubay, Ryan. et al. Single-Cell Microgels for Diagnostics and Therapeutics. Advanced functional materials 31(44):2009946, 1-54 (2021).
Edelman, Gerald M, and Joseph A. Gally. Degeneracy and complexity in biological systems. Proc Natl Acad Sci USA. 98(24):13763-13768 (2001).
Eich, Marcus. Cell Sorting, an Overview. Dkfz :1-38 (2016).
Engineering of CAR T cells for research use, Isolation of donor T cells, in vitro activation, transduction, expansion, phenotyping, and functional analysis. Miltenyi Biotec :1-12 (2019).
Eyer, Klaus. et al. A microchamber array for single cell isolation and analysis of intracellular biomolecules. Lab on a Chip 12(4):765-772 (2012).
Eyer, Klaus. et al. Implementing enzyme-linked immunosorbent assays on a microfluidic chip to quantify intracellular molecules in single cells. Analytical Chemistry 85(6):3280-3287 (2013).
Fairbanks, Benjamin D. et al. A Versatile Synthetic Extracellular Matrix Mimic via Thiol-Norbornene Photopolymerization. Advanced Materials 21(48):5005-5010 (2009).
Fairbanks, Benjamin D. et al. Photodegradable, Photoadaptable Hydrogels via Radical-Mediated Disulfide Fragmentation Reaction. Macromolecules 44(8):2444-2450 (2011).
Falconnet, Didier. et al. Surface engineering approaches to micropattern surfaces for cell-based assays. Biomaterials 27(16):3044-3063 (2006).
Falconnet, Didier. et al. Surface Engineering Approaches to Micropattern Surfaces for Cell-based Assays. Biomaterials 27(16):3044-3063 (2006). (Abstract Only).
Fan, H Christina. et al. Expression profiling. Combinatorial labeling of single cells for gene expression cytometry. Science 347(6222): 1258367, 1-10 (2015).
Fattahi, et al., Photodegradable hydrogels for rapid screening, isolationm and genetic characterization of bacteria with rare phenotypes. Biomacromolecules, ACS, Jun. 19, 2020; 12 Pages.
Fattahi, Niloufar. Hydrogel interfaces for applications in microbial biotechnology. 2021. 172 Pages.
Fiorini, Gina S, and Daniel T Chiu. Disposable microfluidic devices: fabrication, function, and application. BioTechniques 38(3):429-446 (2005).
Fischbach, Michael A. et al. Cell-based Therapeutics: the Next Pillar of Medicine. Science Translational Medicine 5(179):179ps7, 1-6 (2013).
Fixe, F. et al. Functionalization of poly (methyl methacrylate)(PMMA) as a substrate for DNA microarrays. Nucleic acids research 32(1):e9, 1-8 (2004).
Frydrych-Tomczak, Emilia. et al. Application of epoxy functional silanes in the preparation of DNA microarrays. BioTechnologia. Journal of Biotechnology Computational Biology and Bionanotechnology 95(1):5-16 (2014).
Fu, et al. Digital encoding of cellular mRNAs enabling precise and absolute gene expression measurement by single-molecule counting. Anal Chem. Mar. 18, 2014;86(6):2867-70. doi: 10.1021/ac500459p. Epub Mar. 4, 2014.
Fu, Xiaonan. et al. Continuous Polony Gels for Tissue Mapping with High Resolution and RNA Capture Efficiency. bioRxiv :1-20 (2021).
Fu, Xiaonan et al, Continuous polony gels for tissue mapping with high resolution and RNA capture efficiency. bioRxiv (2021.03.17. 435795).
Fu, Xiaonan. et al. Polony gels enable amplifiable DNA stamping and spatial transcriptomics of chronic pain. Cell 185(24):4621-4633 (2022).
Futamura, Yushi. et al. Morphobase, an encyclopedic cell morphology database, and its use for drug target identification. Chemistry and biology 19(12):1620-1630 (2012).
Gao, Shipeng. et al. Oriented immobilization of antibodies onto sensing platforms—A critical review. Analytica chimica acta 1189:338907, 1-24 (2022).
Garagorri, Nerea. et al. Keratocyte behavior in three-dimensional photopolymerizable poly(ethylene glycol) hydrogels. Acta Biomaterialia 4(5):1139-1147 (2008).
Gascoyne, Peter RC. et al. Isolation of rare cells from cell mixtures by dielectrophoresis. Electrophoresis 30(8):1388-1398 (2009).
Gauvin et al, "Microfabrication of complex porous tissue engineering scaffolds using 3D projection stereolithography," Biomaterials, 33(15): 3824-3834 (2012).
Geckil et al, "Engineering hydrogels as extracellular matrix mimics," Nanomedicine (Lond.) 5(3): 469-484 (2010).
Gerstner, Andreas OH. et al. Comparison of immunophenotyping by slide-based cytometry and by flow cytometry. Journal of immunological methods 311(1-2):130-138 (2006).
Gharizadeh, Baback. et al. Viral and Microbial Genotyping by a Combination of Multiplex Competitive Hybridization and Specific Extension Followed by Hybridization to Generic Tag Arrays. Nucleic Acids Research 31(22):e146, 1-12 (2003).
Ghassemi, Zahra. et al. Stability of proteins encapsulated in Michael-type addition polyethylene glycol hydrogels. Biotechnology and bioengineering 118(12):4840-4853 (2021).
Giese, Roger W. Electrophoric Release Tags: Ultrasensitive Molecular Labels Providing Multiplicity. TrAC Trends in Analytical Chemistry 2(7):166-168 (1983).
Giordano, Frank A. et al. High-throughput Monitoring of Integration of Integration Site Clonality in Preclinical and Clinical Gene Therapy Studies. Molecular Therapy Methods & Clinical Development 2:14061, 1-8 (2015).
Goda, Keisuke. et al. In flow cytometry, image is everything. Cytometry Part A 95(5):475-477 (2019).
Goldring, Chris E P. et al. Assessing the safety of stem cell therapeutics. Cell Stem Cell 8(6):618-628 (2011).
Gomes, Tomás et al. Immunology driven by large-scale single-cell sequencing. Trends in immunology 40(11):1011-1021 (2019).
Gopinath, Ashwin. et al. Engineering and mapping nanocavity emission via precision placement of DNA origami. Nature 535(7612):401-405 (2016).
Gordeeva, Veronika. et al. Progress in Methods for Copy Number Variation Profiling. International Journal of Molecular Sciences 23(4):2143, 1-20 (2022).
Greenbaum, Dov. et al. Comparing protein abundance and mRNA expression levels on a genomic scale. Genome Biology 4(9):117, 1-8 (2003).
Greenberg, Marc M, and John L. Gilmore. Cleavage of Oligonucleotides from Solid-Phase Supports Using o-Nitrobenzyl Photochemistry. 59(4):746-753 (1994).
Grier, David G. A revolution in optical manipulation. nature 424(6950):810-816 (2003).
Griffin et al, "Photodegradable macromers and hydrogels for live cell encapsulation and release," J. Amer. Chem. Soc., 134: 13103-13107 (2012).
Gunderson, Kevin L. et al. Decoding randomly ordered DNA arrays. Genome Research 14(5):870-877 (2004).
Gunning, Kerry B. et al. Improved Print and QC Methods for Oligonucleotide Arrays. Integrated DNA Technologies :1-10 (2003).

(56) References Cited

OTHER PUBLICATIONS

Haeberle, Stefan, and Roland Zengerle. Microfluidic platforms for lab-on-a-chip applications. Lab on a chip 7(9):1094-1110 (2007).
Hahn et al, "Photolithographic patterning of polyethylene glycol hydrogels," Biomaterials, 27: 2519-2524 (2006).
Hammoudi et al, "Long-term spatially defined coculture within three-dimensional photopatterned hydrogels," Tissue Engineering, 16(6): 1621-1628 (2010).
Han et al, "Fabrication of three-dimensional scaffolds for heterogeneous tissue engineering," Biomed. Microdevices, 12: 721-725 (2010).
Hao, Yiting. et al. Visible light cured thiol-vinyl hydrogels with tunable degradation for 3D cell culture. Acta biomaterialia 10(1):104-114 (2014).
Hardenbol, Paul. et al. Multiplexed genotyping with sequence-tagged molecular inversion probes. Nature biotechnology 21(6):673-678 (2003).
Hashimshony, Tamar. et al. CEL-Seq2: sensitive highly-multiplexed single-cell RNA-Seq. Genome Biology 17:77, 1-7 (2016).
Heiman, Myriam. et al. Cell type-specific mRNA purification by translating ribosome affinity purification (TRAP). Nature Protocols 9(6):1282-1291 (2014).
Heo et al, "A microfluidic bioreactor based on hydrogel-entrapped *E. coli*: Cell viability, lysis, and intracellular enzyme reactions," Anal. Chem., 75: 22-26 (2003).
Hickey, John W. et al. Spatial mapping of protein composition and tissue organization: a primer for multiplexed antibody-based imaging. Nature Methods 19(3):284-295 (2022). Published Online Nov. 22, 2021.
Hochgerner, et al. STRT-seq-2i: dual-index 5' single cell and nucleus RNA-seq on an addressable microwell array. Scientific Reports 7:16327 (2017).
Hollyman, Daniel. et al. Manufacturing Validation of Biologically Functional T Cells Targeted to CD19 Antigen for Autologous Adoptive Cell Therapy. Journal of Immunotherapy 32(2):169-180 (2009).
Holmes, Christopher P. Model Studies for New o-Nitrobenzyl Photolabile Linkers: Substituent Effects on the Rates of Photochemical Cleavage. The Journal of Organic Chemistry 62(8):2370-2380 (1997).
Hong et al, "Cell microarray technologies for high-throughput cell-based sensors," Sensors, 17: 1293 (2017).
Hoshino, Kazunori. et al. Microchip-based immunomagnetic detection of circulating tumor cells. Lab on a Chip 11(20):3449-3457 (2011).
Hou, Ping. et al. Photo-cross-linked biodegradable hydrogels based on n-arm-poly(ethylene glycol), poly(e-caprolactone) and/or methacrylic acid for controlled drug release. Journal of Biomaterials Applications 32(4):511-523 (2017).
Hou, Young. et al. Comparison of variations detection between whole-genome amplification methods used in single-cell resequencing. Gigascience 4:37, 1-16 (2015).
Hsieh, Wan-Chen. et al. Spatial multi-omics analyses of the tumor immune microenvironment. Journal of Biomedical Science 29(1):96, 1-17 (2022).
Hu, Fangxiao. et al. Hematopoietic lineage-converted T cells carrying tumor-associated antigen-recognizing TCRs effectively kill tumor cells. Journal for Immunotherapy of Cancer 8(2):1-8 (2020).
Hu, Jingjing. et al. A thermo-degradable hydrogel with light-tunable degradation and drug release. Biomaterials 112:133-140 (2017).
Hu, Jingjing. et al. A thermo-degradable hydrogel with light-tunable degradation and drug release. Biomaterials 112:133-140 (2017). (Abstract Only).
Huang, Bo. et al. Counting low-copy number proteins in a single cell. Science 315(5808):81-84 (2007).
Huang et al, "Light-addressed electrodeposition of enzyme-entrapped chitosan membranes for multiplexed enzyme-based bioassays using a digital micromirror device," Sensors, 13: 10711-10724 (2013).
Huang, Lu, et al. Current Advances in Highly Multiplexed Antibody-Based Single-Cell Proteomic Measurements. Chemistry An Asian Journal 12(14):1680-1691 (2017).
Huang, Shih-Hao. et al. Light-addressable Electrodeposition of Cell-encapsulated Alginate Hydrogels for a Cellular Microarray Using a Digital Micromirror Device. Biomicrofluidics 5(3):034109, 1-10 (2011).
Hughes, T.R. et al. Expression profiling using microarrays fabricated by an ink-jet oligonucleotide synthesizer. Nature biotechnology 19(4):342-347 (2001).
Hui, Jeremy R., and Massachusetts Institute of Technology. Department of Electrical Engineering and Computer Science. Optical Tweezers Using the Texas Instruments' Digital Micromirror Device(Tm). Massachusetts Institute of Technology, Department of Electrical Engineering and Computer Science. 71 pages (2001).
Ifkovits et al, "Review: Photopolymerizable and degradable biomaterials for tissue engineering applications," Tissue Engineering, 13(10): 2369-2385 (2007).
Illumina Bio-Rad SureCell 3' WTA for ddSEQ. [retrieved on Sep. 23, 2020]. Available at URL: https://teichlab.github.io/scg_lib_structs/methods_html/SureCell.html pp. 1-2.
Illumina. For all you seq. Illumina Acientific Affairs. 2 pages (2015).
InstrumentZERO, Your Modular Solution in Micro-Dispensing. M2-Automation :1-2 (2018).
Integrated generation and characterization of CAR T cells. ThermoFisher Scientific :1-7 (2020).
Introduction to Illumina Sequencing. The Overwhelming Landscape of Next-Gen Sequencing Methods :1-14 (2025).
Isakova, Alina et al., Single cell profiling of total RNA using Smart-seq-total. bioRxiv preprint. pp. 1-18 (2020). Available at https://www.biorxiv.org/content/10.1101/2020.06.02.131060v1.
Islam, Saiful, et al., Characterization of the single-cell Transcriptional landscape by Highly Multiplex RNA-seq. Genome Research 21(7):1160-1167 (2011).
Islam, Saiful. et al. Quantitative Single-cell RNA-Seq With Unique Molecular Identifiers. Nature Methods 11(2):163-166 (2014).
Ismagilov, Rustem F. et al. Microfluidic Arrays of Fluid-Fluid Diffusional Contacts as Detection Elements and Combinatorial Tools. Analytical Chemistry 73:5207-5213 (2001).
Isozaki, Akihiro. et al. A practical guide to intelligent image-activated cell sorting. Nature protocols 14(8):2370-2415 (2019).
Jen, Chun-Ping. et al. Single-cell chemical lysis on microfluidic chips with arrays of microwells. Sensors 12(1):347-358 (2012). Published Online Dec. 30, 2011.
Jones, Jesse W, and Robins, Ronald K. Purine Nucleosides 111 Methylation Studies of Certain Naturally Occurring Purine Nucleosides. Journal of the American Chemical Society 85(2):193-201 (1963).
Jung, Sukwon. et al. Controlled network structures of chitosan-poly(ethylene glycol) hydrogel microspheres and their impact on protein conjugation. Biochemical Engineering Journal 135:123-132 (2018).
Kabb, Christopher P. et al. Photoreversible Covalent Hydrogels for Soft-Matter Additive Manufacturing. ACS Applied Materials and Interfaces 10(19):16793-16801 (2018).
Kahl, Jeffrey D, and Marc M. Greenberg. Solution-Phase Bioconjugate Synthesis Using Protected Oligonucleotides Containing 3'-Alkyl Carboxylic Acids. The Journal of Organic Chemistry 64(2):507-510 (1999).
Kahl, Jeffrey D. et al. High-Yielding Method for On-col. Derivatization of Protected Oligodeoxy-nucleotides and Its Application to the Convergent Synthesis of 5',3'-Bis-conjugates. Journal of Organic Chemistry 63(15):4870-4871 (1998).
Kaiser. Towards a commercial process for the manufacture of genetically modified T cells for therapy. Cancer Gene Thera 22(2):72-78 (2015).
Kamentsky, Louis A, and Lee D. Kamentsky. Microscope-based multiparameter laser scanning cytometer yielding data comparable to flow cytometry data. Cytometry: The Journal of the International Society for Analytical Cytology 12(5):381-387 (1991).
Kanfer, Gil. et al. Image-based pooled whole-genome CRISPRi screening for subcellular phenotypes. Journal of Cell Biology 220(2):e202006180, 1-24 (2021).

(56) References Cited

OTHER PUBLICATIONS

Kang, Chi-Chih. et al. Single cell-resolution western blotting. Nature Protocols 11(8):1508-1530 (2016).
Kang, Chi-Chih. et al. Single-cell western blotting after whole-cell imaging to assess cancer chemotherapeutic response. Analytical Chemistry 86(20):10429-10436 (2014).
Kang, Joo H. et al. Analysis of pressure-driven air bubble elimination in a microfluidic device. Lab on a Chip 8(1):176-178 (2008).
Kar, Mrityunjoy. et al. Poly (ethylene glycol) hydrogels with cell cleavable groups for autonomous cell delivery. Biomaterials 77:186-197 (2016). Published Online Nov. 10, 2015.
Kelly, Ryan T. Single-cell proteomics: progress and prospects. Molecular and Cellular Proteomics 19(11):1739-1748 (2020).
Kharkar, Prathamesh M. et al. Design of Thiol- and Light-sensitive Degradable Hydrogels using Michael-type Addition Reactions. Polymer Chemistry. 6(31):5565-5574 (2015).
Kharkar, Prathamesh M. et al. Designing degradable hydrogels for orthogonal control of cell microenvironments. Chem Soc Rev 42(17):7335-7372 (2013).
Kharkar, Prathamesh M. et al. Thiol-ene click hydrogels for therapeutic delivery. ACS biomaterials science & engineering 2(2):165-179 (2016).
Kikuchi et al, "Arraying heterotypic single cells on photoactivatable cell-culturing substrates," Langmuir, 24: 13084-13095 (2008).
Kim, Heon Seok. et al. CReVIS-Seq: A Highly Accurate and Multiplexable Method for Genome-wide Mapping of Lentiviral Integration Sites. Molecular Therapy Methods & Clinical Development 20:792-800 (2021).
Kim, Sung Ah. et al. An Efficient and Reliable DNA Extraction Method for Preimplantation Genetic Diagnosis: a Comparison of Allele Drop Out and Amplification Rates Using Different Single Cell Lysis Methods. Fertility and Sterility 92(2):814-818 (2009).
Kim, Tae Kyung, and James H Eberwine. Mammalian cell transfection: the present and the future. Analytical and Bioanalytical Chemistry 397(8):3173-3178 (2010).
Kivlehan et al, "Three-dimensional hydrogel structures as optical sensor arrays, or the detection of specific DNA sequences," Anal. Biochem., 421: 1-8 (2012).
Kleino, Livari. et al. Computational solutions for spatial transcriptomics. Computational and structural biotechnology journal 20:4870-4884 (2022).
Klito, Niels GF. et al. Arrayed Primer Extension in the "Array of Arrays" Format: A Rational Approach for Microarray-Based SNP Genotyping. Genetic Testing 11(2):160-166 (2007).
Kloxin et al, "Photodegradable hydrogels for dynamic tuning of physical and chemical properties," Science, 324(5923): 59-63 (2009).
Koh, "Cell microarrays based on hydrogel microstructures for the application to cell-based biosensor," Chapter 7, in Biological Microarrays: Methods and Protocols, Methods in Molecular Biology, vol. 671 (2011).
Koh et al, "Fabrication of cell-containing hydrogel microstructures inside fluidic devices that can be used as cell-based biosensors," Anal. Bioanal. Chem., 385: 1389-1397 (2006).
Koh, Won-Gun. et al. Poly(ethylene glycol) Hydrogel Microstructures Encapsulating Living Cells. Langmuir 18(7):2459-2462 (2002).
Kovac, Joseph. et al. Image-predicated sorting of adherent cells using photopatterned hydrogels. Advanced healthcare materials 2(4):552-556 (2012).
Kozak, Karol. et al. Data mining techniques in high content screening: a survey. Journal of Computer Science and Systems Biology 2(4):219-239 (2009).
Kozak, Karol. et al. Multiparametric analysis of high content screening data. Journal of Biomedicine 2:78-88 (2017).
Krämer, Stefan D. et al. How to copy and paste DnA microarrays. Scientific Reports. 9:13940, 1-10 (2019).
Kubiak-Ossowska, Karina, and Paul A. Mulheran. What governs protein adsorption and immobilization at a charged solid surface?. Langmuir 26(11):7690-7694 (2010).
Kwon, Seong Gyu. et al. Recent Advances in Stem Cell Therapeutics and Tissue Engineering Strategies. Biomaterials Research 22:36, 1-8 (2018).
Labelle, Cody A. et al. Image-Based Live Cell Sorting. Trends in Biotechnology 39(6):613-623 (2021). Published online on Nov. 13, 2020.
Lange, Sebastian A. et al. Microcontact printing of DNA molecules. Analytical chemistry 76(6):1641-1647 (2004). (Abstract Only).
Latour, Robert A. Biomaterials: Protein-Surface Interactions. Encyclopedia of Biomaterials and Biomedical Engineering 1:270-284 (2005).
Lauer, Stephanie. et al. Single-cell copy No. variant detection reveals the dynamics and diversity of adaptation. PLoS Biol 16(12):e3000069, 1-35 (2018).
Le, Hue P. Chapter 1: Progress and Trends in Ink-jet Printing Technology. Recent Progress in Ink Jet Technologies II. 1-14 (1999).
Leary, James F. Ultra high-speed sorting. Cytometry Part A: The Journal of the International Society for Analytical Cytology 67(2):76-85 (2005).
Lee, Je Hyuk. et al. Highly multiplexed subcellular RNA sequencing in situ. Science 343(6177):1360-1363 (2014).
Lee, Jeong H. al. Lossless immunocytochemistry using photopolymerized hydrogel thin-films. Analyst 145(8):2897-2903 (2020).
Lee, Jeongwoo. et al. Single-cell multiomics: technologies and data analysis methods. Experimental & Molecular Medicine 52(9):1428-1442 (2020).
Leenman, Elena E. et al. Rapid Determination of Epstein-barr Virus Latent or Lytic Infection in Single Human Cells Using in Situ Hybridization. Modern Pathology 17(12):1564-1572 (2004).
Lehninger, Albert L. The Molecular basis of Cell Structure and Function, Second Edition. Biochemistry :1-2 (1975).
Lei, Yuguo, and Tatiana Segura. DNA delivery from matrix metalloproteinase degradable poly (ethylene glycol) hydrogels to mouse cloned mesenchymal stem cells. Biomaterials 30(2):254-265 (2009).
Leriche, Geoffray. et al. Cleavable linkers in chemical biology. Bioorganic & medicinal chemistry 20(2):571-582 (2012).
Levalley, Paige J. et al. On-demand and tunable dual wavelength release of antibody using light-responsive hydrogels. ACS Appl Bio Mater 3(10):6944-6958 (2020).
Levine, Bruce L. et al. Global Manufacturing of CAR T Cell Therapy. Molecular Therapy. Methods & Clinical Development 4:92-101 (2016).
Levy, Ezra, and Nikolai Slavov. Single cell protein analysis for systems biology. Essays in Biochemistry 62(4):595-605 (2018).
Lewis, Sabrina M. et al. Spatial omics and multiplexed imaging to explore cancer biology. Nature Methods 18(9):997-1012 (2021).
Li, Wenli, and Michael Olivier. Current analysis platforms and methods for detecting copy number variation. Physiol Genomics 45(1):1-16 (2013). Published online Nov. 6, 2012.
Li, Xinda. et al. Inkjet bioprinting of biomaterials. Chemical Reviews 120(19):10793-10833 (2020).
Li, Xinda. et al. Inkjet bioprinting of biomaterials. Chemical Reviews 120(19):10793-10833 (2020). (Abstract Only).
Li, Zhuxia, and Guangdun Peng. Spatial transcriptomics: new dimension of understanding biological complexity. Biophysics reports 8(3):119-135 (2022).
Lichtenberg, Jessanne Y. et al. Non-specific adsorption reduction methods in biosensing. Sensors 19(11):2488, 1-17 (2019).
Liehr, T. et al. Multicolor FISH probe sets and their applications. Histol Histopathol 19(1):229-237 (2004).
Liu et al, "A microfluidic photolithography for controlled encapsulation of single cells inside hydrogel microstructures," Science China Chemistry, 55(4): 494-501 (2012).
Liu et al, "Controlled photopolymerization of hydrogel microstructures inside microchannels for bioassays," LabChip, 9: 1301-1305 (2009).
Liu, Susan Marisa. The Thermodynamics of Irreversible Nonspecific Protein Adsorption at a Solid-Aqueous Interface. The University of British Columbia :1-151 (1997).
Liu, Yang. et al. High-spatial-resolution multi-omics sequencing via deterministic barcoding in tissue. Cell 183(6):1665-1681 (2020).

(56) References Cited

OTHER PUBLICATIONS

Ljosa, Vebjorn. et al. Comparison of methods for image-based profiling of cellular morphological responses to small-molecule treatment. Journal of biomolecular screening 18(10):1321-1329 (2013).
Lo, Catherine T. et al. Photopolymerized diffusion-defined polyacrylamide gradient gels for on-chip protein sizing. Lab on a Chip 8(8):1273-1279 (2008).
Loo, Lit-Hsin. et al. Image-based multivariate profiling of drug responses from single cells. Nature methods 4(5):445-453 (2007).
Low, Wan Shi, and Wan Abu Bakar Wan Abas. Benchtop technologies for circulating tumor cells separation based on biophysical properties. BioMed research international 2015(1):239362, 1-22 (2015).
Lu et al, "A digital micro-mirror device-based system for the microfabrication of complex, spatially patterned tissue engineering scaffolds," J. Biomed. Mater. Research, 77A(2): 396-405 (2006).
Lyubetskaya, Anna. et al. Assessment of spatial transcriptomics for oncology discovery. Cell Rep Methods 2(11):100340, 1-28 (2022).
Mace, David C. N6-Methyldeoxyadenosine 5"Triphosphate As a Probe of the Fidelity Mechanisms of Bacteriophage T4 DNA Polymerase. The Journal of Biological Chemistry 259(6):3616-3619 (1984).
Mackay, Ian M. et al. Real-time PCR in virology. Nucleic Acids Research 30(6):1292-1305 (2002).
Macosko, Evan Z. et al. Highly Parallel Genome-wide Expression Profiling of Individual Cells Using Nanoliter Droplets. Cell 161(5):1202-1214 (2015).
Macosko, Evan Z. et al. Highly Parallel Genome-wide Expression Profiling of Individual Cells Using Nanoliter Droplets. Cell 161(5):1202-1214 (2015). With Supplementary Information.
Mallory, Xian F. et al. Methods for copy number aberration detection from single-cell DNA-sequencing data. Genome Biology 21:208, 1-22 (2020).
Martel, Ralph R. et al. Array formats. Microarray technology and its applications :3-22 (2005).
Maruyama, Hisataka. et al. Immobilization of individual cells by local photo-polymerization on a chip. Analyst 130(3):304-310 (2005).
Milo, Ron. What is the total number of protein molecules per cell volume? A call to rethink some published values. Bioessays 35(12):1050-1055 (2013).
Mobed-Miremadi, Maryam. et al. Fickian-based empirical approach for diffusivity determination in hollow alginate-based microfibers using 2D fluorescence microscopy and comparison with theoretical predictions. Materials 7(12):7670-7688 (2014).
Moeinzadeh, Seyedsina. et al. Synthesis and gelation characteristics of photo-crosslinkable star poly (ethylene oxide-co-lactide-glycolide acrylate) macromonomers. Polymer 52(18):3887-3896 (2011).
Mondal, Manas. Multiplexed Single-cell Spatial Proteomics and Transcriptomics. Arizona State University :1-179 (2018).
Moses et al. Museum of spatial transcriptomics. Nat Methods 19(5):534-546 (2022).
Murphy, Travis W. et al. Recent advances in the use of microfluidic technologies for single cell analysis. Analyst 143(1):60-80 (2018).
Mustapha, Farah. et al. Protocol for measuring weak cellular traction forces using well-controlled ultra-soft polyacrylamide gels. STAR Protocols 3(1):101133, 1-16 (2022).
Myung, J. H, and S. Hong. Microfluidic devices to enrich and isolate circulating tumor cells. Lab on a Chip 15(24):4500-4511 (2015).
Nagarajan, et al. Spatially resolved and multiplexed MicroRNA quantification from tissue using nanoliter well arrays. Microsystems & Nanoengineering 6(51):1-9 (2020).
Naiser et al, "A versatile maskless microscope projection photolithography system and its application in light-directed fabrication of DNA microarrays," Rev. Sci. Instr., 77: 063711 (2006).
Nebbioso, Angela. et al. Time-resolved analysis of DNA-protein interactions in living cells by UV laser pulses. Scientific Reports 7(1):11725, 1-13 (2017).
Negishi et al, "High-throughput manipulation of circulating tumor cells using a multiple single-cell encapsulation system with a digital micromirror device," Anal. Chem., 90: 9734-9741 (2018).
Neumann, Alexander J. et al. Nondestructive evaluation of a new hydrolytically degradable and photo-clickable PEG hydrogel for cartilage tissue engineering. Acta biomaterialia 39:1-11 (2016).
New Product—MGB Eclipse CPG. The Glen Report. Glen Research 33.1:1-12 (2021).
Next-Generation Sequencing Illumina Workflow-4 Key Steps. ThermoFisher Scientific. 7 pages (2022).
Nguyen et al, "Photopolymerizable hydrogels for tissue engineering applications," Biomaterials, 23: 4307-4314 (2002).
Nichol et al, "Cell-laden microengineered gelatin methacrylate hydrogels," Biomaterials, 31(21): 5536-5544 (2010).
Nicodemus et al, "Cell encapsulation in biodegradable hydrogels for tissue engineering applications," Tissue Engineering, Part B, 14(2): 149-165 (2008).
Nsamela, Audrey. Microfluidics for sperm sorting: a review. Microfluidic Reviews, Apr. 22, 2021 ;[retrieved on Apr. 13, 2022]. Available at URL:https://www.elveflow.com/microfluidic-reviews/microfluidics-for-cell-biology/microfluidic-for-sperm-sorting-a-review/ pp. 1-5.
Nunc MaxiSorp flat-bottom, ELISA plates. Thermo Fisher Scientific (2016).
Oldenhof, Sander. et al. Imaging-assisted hydrogel formation for single cell isolation. Scientific Reports 10(1):6595, 1-10 (2020).
Oldenhof, Sander. et al. Imaging-assisted hydrogel formation for single cell isolation. Scientific Reports 10(6595):1-10 (2020).
Ozcelik, B. Degradable hydrogel systems for biomedical applications. Biosynthetic Polymers for Medical Applications, Woodhead Publishing :173-188 (2016).
Ozcelik, B. Degradable hydrogel systems for biomedical applications. Biosynthetic Polymers for Medical Applications, Woodhead Publishing :173-188 (2016). (Abstract Only).
Panda et al, "Stop-flow lithography to generate cell-laden microgel particles," LabChip, 8(7): 1056-1061 (2008).
Papavasiliou et al, "Three-dimensional patterning of poly(ethylene glycol) hydrogels through surface-initiated photopolymerization," Tissue Engineering, part C, 14(2): 129-140 (2008).
Paruzynski, Anna. et al. Genome-wide High-throughput Integrome Analyses by nrLAM-PCR and Next-generation Sequencing. Nature Protocols 5(8):1379-1395 (2010).
Paugh, Barbara S. et al. Reference standards for accurate validation and optimization of assays that determine integrated lentiviral vector copy number in transduced cells. Scientific Reports 11:389, 1-9 (2021).
PCT/US2017/041656 International Search Report and Written Opinion dated Sep. 21, 2017.
PCT/US2022/011720 International Search Report and Written Opinion dated Jun. 7, 2022.
PCT/US2022/033116 International Search Report and Written Opinion dated Nov. 3, 2022.
PCT/US2023/015806 International Search Report and Written Opinion dated Aug. 4, 2023.
PCT/US2023/015806 Invitation to Pay Additional Fees dated May 22, 2023.
PCT/US2023/017896 International Search Report and Written Opinion dated Jul. 3, 2023.
PCT/US2023/023004 International Search Report and Written Opinion dated Aug. 23, 2023.
PCT/US2023/068154 International Preliminary Report on Patentability dated Dec. 19, 2024.
PCT/US2023/068154 International Search Report and Written Opinion dated Oct. 10, 2023.
PCT/US2023/070428 International Search Report and Written Opinion dated Nov. 6, 2023.
PCT/US2023/077802 International Search Report and Written Opinion dated Mar. 15, 2024.
PCT/US2023/077802 Invitation to Pay Additional Fees dated Jan. 19, 2024.
PCT/US2023/086095 International Search Report dated Apr. 10, 2024.
PCT/US2024/048730 International Search Report and Written Opinion dated Jan. 10, 2025.

(56) References Cited

OTHER PUBLICATIONS

PCT/US2024/059913 International Search Report and Written Opinion dated Apr. 10, 2025.
PCT/US2024/059913 Invitation to Pay Additional Fees dated Feb. 20, 2025.
PCT/US2025/026829 Invitation to Pay Additional Fees dated Jun. 24, 2025.
PCT/US2025/027625 Invitation to Pay Additional Fees dated Jun. 17, 2025.
PCT/US2025/027630 International Search Report and Written Opinion dated Jul. 2, 2025.
PCT/US2025/027631 International Search Report and Written Opinion dated Jul. 3, 2025.
PCT/US2025/027635 International Search Report and Written Opinion dated Jul. 25, 2025.
PCT/US2025/027635 Invitation to Pay Additional Fees dated Jun. 5, 2025.
Peng, Yujia. et al. CD25: A potential tumor therapeutic target. International Journal of Cancer 152(7):1290-1303 (2023).
Pereiro, Iago. et al. Nip the bubble in the bud: a guide to avoid gas nucleation in microfluidics. Lab on a Chip 19(14):2296-2314 (2019).
Perlman, Zachary E. et al. Multidimensional drug profiling by automated microscopy. Science 306(5699):1194-1198 (2004).
Petalidis L. et al., Global amplification of mRNA by template-switching PCR: linearity and application to microarray analysis. Nucleic Acids Research. 31(22):e14, pp. 1-7 (2003).
Peterson, Vanessa M. et al. Multiplexed Quantification of Proteins and Transcripts in Single Cells. Nature Biotechnology 35(10):936-939 (2017).
Phillips, Margaret F. et al. In situ oligonucleotide synthesis on carbon materials: stable substrates for microarray fabrication. Nucleic Acids Res 36(1):e7, 1-9 (2008).
Picelli, Simone. et al. Tn5 Transposase and Tagmentation Procedures for Massively Scaled Sequencing Projects. Genome Research 24(12):2033-2040 (2014).
Ploem-Zaaijer, J J. et al. Automated image cytometry for detection of rare, viral antigen-positive cells in peripheral blood. Cytometry 15(3):199-206 (1994).
Pollock et al, "Highly multiplexed and quantitative cell-surface protein profiling using genetically barcoded antibodies," Proc. Natl. Acad. Sci., 115(11): 2836-2841 (2018).
Pon, Richard T. Solid-Phase Supports for Oligonucleotide Synthesis. Methods in Molecular Biology 20:465-496 (1993).
Porter, Shaina N. et al. Lentiviral and targeted cellular barcoding reveals ongoing clonal dynamics of cell lines in vitro and in vivo. Genome Biology 15:R75, 1-14 (2014).
Price, Graeme, and Kristin Baird. Scientific and Regulatory Considerations for Gene Modified T Cell Therapy. U.S. Food Drug Administration (2025).
Quan, Jiayuan. et al. Parallel on-chip Gene Synthesis and Application to Optimization of Protein Expression. Nature biotechnology 29(5):449-452 (2011).
Quan, Li Na. et al. Edge stabilization in reduced-dimensional perovskites. Nature Communications 11(1):170, 1-9 (2020).
Rabe, M. et al. Specific and Non-Specific Adsorption of Proteins on Solid Interfaces. NSTI Nanotech 2:500-503 (2007).
Rabe, Michael. et al. Understanding Protein Adsorption Phenomena at Solid Surfaces. University of Zurich :1-170 (2009).
Raman, Ritu. et al. Light-degradable hydrogels as dynamic triggers for gastrointestinal applications. Science advances 6(3):eaay0065, 1-11 (2020).
Ramskold, Daniel. et al. Supplemental Information (NIHMS379463-Supplement-1): Full-length mRNA-Seq from single-cell levels of RNA and individual circulating tumor cells. Nature Biotechnology 30(8):777-782 (2012).
Rana, Md Sohel. et al. Selection of object detections using overlap map predictions. Neural Computing and Applications 34:18611-18627 (2022).
Ratajczak, Tomasz. et al. The "Clickable" Method for Oligonucleotide Immobilization Onto Azide-Functionalized Microarrays. Methods in molecular biology 1368:25-36 (2016).
Ratajczak, Tomasz. et al. The "clickable" method for oligonucleotide immobilization onto azide-functionalized microarrays. Microarray Technology: Methods and Applications 1368:25-36 (2016). (Abstarct Only).
Recek, Nina. et al. Protein adsorption on various plasma-treated polyethylene terephthalate substrates. Molecules 18(10): 12441-12463 (2013).
Reimhult, Erik, and Fredrik Hook. Design of surface modifications for nanoscale sensor applications. Sensors 15(1):1635-1675 (2015).
Reina, Olwen. Six Ways to Measure T Cell Responses. BiteSize Bio, Jan. 21, 2015; [Retrieved on Feb. 13, 2022]. Available at URL: https://bitesizebio.com/22831/six-ways-to-measure-t-cell-responses/. pp. 1-8.
Ren, Dahai. et al. Micropatterning of Single Cell Arrays Using the PEG-silane and Biotin-(Strept)avidin System With Photolithography and Chemical Vapor Deposition. Sensors and Actuators B: Chemical 188:340-346 (2013). (Abstract Only).
Ren, Kangning. et al. Materials for microfluidic chip fabrication. Accounts of chemical research 46(11):2396-2406 (2013).
Restifo, Nicholas P. et al. Adoptive Immunotherapy for Cancer: Harnessing the T Cell Response. Nature Reviews. Immunology 12(4):269-281 (2012).
Rettig, et al. Large-scale single-cell trapping and imaging using microwell arrays. Anal Chem. Sep. 1, 2005;77(17):5628-34. Published on Web Jul. 30, 2005.
Rissin, David M. et al. Single-molecule enzyme-linked immunosorbent assay detects serum proteins at subfemtomolar concentrations. Nature Biotechnology 28(6):595-599 (2010).
Rodriques et al. Slide-seq: A scalable technology for measuring genome-wide expression at high spatial resolution. Science 363(6434):1463-1467 (Supplementary Material) (2019).
Rodriques, Samuel. et al. Slide-seq: A scalable technology for measuring genome-wide expression at high spatial resolution. Science 363(6434):1463-1467 (2019).
Rolf, Julia. et al. AMPK a1: A glucose sensor that controls CD 8 T-cell memory. European journal of immunology 43(4):889-896 (2013).
Russell et al, "Mass transfer in rapidly photopolymerized poly(ethylene glycol) hydrogels used for chemical sensing," Polymer, 42: 4893-4901 (2001).
Salazar, Georgina To'A. et al. Characterization of the laser-based release of micropallets from arrays. Journal of Biomedical Optics 13(3):034007, 1-9 (2008).
Saliba, Antoine-Emmanuel. et al. Single-cell RNA-seq: advances and future challenges. Nucleic acids research 42(14):8845-8860 (2014).
Saliba, et al. Survey and Summary Single-cell RNA-seq: advances and future challenges. Nucleic Acids Research 42(14):8845-8860 (2014).
Salmen, Fredrik. et al. Barcoded solid-phase RNA capture for Spatial Transcriptomics profiling in mammalian tissue sections. Nature protocols 13(11):2501-2534 (2018).
Sato, Katsuaki, and Shigeharu Fujita. Dendritic cells-nature and classification. Allergology International 56(3):183-191 (2007).
Saudemont, A. et al., "Current Status of Gene Engineering Cell Therapeutics," Front Immunol, 2018, vol. 9, No. 153.
Schiro, Perry G. et al. Sensitive and high-throughput isolation of rare cells from peripheral blood with ensemble-decision aliquot ranking. Angewandte Chemie (International ed. in English) 51(19):4618-4622 (2012).
Schmid, Ingrid. et al. Sensitive method for measuring apoptosis and cell surface phenotype in human thymocytes by flow cytometry. Cytometry 15(1):12-20 (1994).
Schmidt, Manfred. et al. High-resolution Insertion-site Analysis by Linear Amplification-mediated PCR (LAM-PCR). Nature Methods 4(12):1051-1057 (2007).
Schmidt, Wolfgang M., and Manfred W. Mueller. CapSelect: a highly sensitive method for 5' CAP-dependent enrichment of full-length cDNA in PCR-mediated analysis of mRNAs. Nucleic Acids Research 27(21):e31, 1-4 (1999).

(56) References Cited

OTHER PUBLICATIONS

Sekine, Kazuhiko. et al. Panning of Multiple Subsets of Leukocytes on Atibody-decorated Poly(ethylene) Glycol-coated Glass Slides. Journal of Immunological Methods 313(1-2):96-109 (2006).
Serien, Daniela, and Sugioka, Koji. Fabrication of three-dimensional proteinaceous micro- and nano-structures by femto-second laser cross-linking. Opto-Electronic Advances 1(4):18000801-18000818 (2018).
Serien, Daniela. et al. Femtosecond Laser Direct Write Integration of Multi-Protein Patterns and 3D Microstructures into 3D Glass Microfluidic Devices. Applied Sciences 8(2):147, 1-13 (2018).
Sesen, Muhsincan, and Graeme Whyte. Image-based single cell sorting automation in droplet microfluidics. Scientific reports 10(1):8736, 1-14 (2020).
Shadpour, Hamed. et al. Enrichment and expansion of cells using antibody-coated micropallet arrays. Cytometry Part A: The Journal of the International Society for Advancement of Cytometry 75(7):609-618 (2009).
Shamir, Lior. et al. Pattern recognition software and techniques for biological image analysis. PLoS computational biology 6(11):e1000974, 1-10 (2010).
Shapiro, et al. Single-cell sequencing-based technologies will revolutionize whole-organism science. Nat Rev Genet. Sep. 2013;14(9):618-30.
Shendure, Jay. et al. Accurate Multiplex Polony Sequencing Of An Evolved Bacterial Genome. Science 309(5741):1728-1732 (2005).
Shields IV, C. Wyatt. et al. Microfluidic cell sorting: a review of the advances in the separation of cells from debulking to rare cell isolation. Lab on a Chip 15(5):1230-1249 (2015).
Shifrut, Eric. et al. Genome-wide CRISPR Screens in Primary Human T Cells Reveal Key Regulators of Immune Function. Cell 175(7):1958-1971.e1-e15 (2018).
Shih, Han and Lin, Chien-Chi. Cross-linking and degradation of step-growth hydrogels formed by thiol-ene photoclick chemistry. Biomacromolecules 13(7):2003-2012 (2012).
Shin, et al., Photodegradable hydrogels for capture, detection, and release of live cells. Angew Chem Int Ed Engl. Jul. 28, 2014; 53(31): 8221-8224. doi:10.1002/anie.201404323.
Shinde, Pallavi. et al. Current trends of microfluidic single-cell technologies. International journal of molecular sciences 19(10):3143, 1-47 (2018).
Sia, Samuel K, and George M Whitesides. Microfluidic devices fabricated in poly(dimethylsiloxane) for biological studies. Electrophoresis 24(21):3563-3576 (2003).
Singh-Gasson, Sangeet. et al. Maskless Fabrication of Light-directed Oligonucleotide Microarrays Using a Digital Micromirror Array. Nature Biotechnology 17(10):974-978 (1999).
Skrdlant, Lindsey M. et al. Detection of Replication Competent Lentivirus using a qPCR Assay for VSV-G. Molecular Therapy Methods & Clinical Development 8:1-7 (2017).
Snyder, Kenneth A. et al. Using viscosity modifiers to reduce effective diffusivity in mortars. Journal of materials in civil engineering 24(8):1017-1024 (2012).
Sobek, Jens. et al. Drop drying on surfaces determines chemical reactivity—the specific case of immobilization of oligonucleotides on microarrays. BMC Biophysics 6:8, 1-14 (2013).
Soman et al, "Digital microfabrication of user-defined 3D microstructures in cell-laden hydrogels," Biotechnol. Bioeng., 110(11): 3038-3047 (2013).
Song, Kwang Hoon. et al. Complex 3D-printed microchannels within cell-degradable hydrogels. Advanced Functional Materials 28(31):1801331, 1-29 (2018).
Song, Yuanping. et al. A Review of Micromirror arrays. Precision Engineering 51:729-761 (2018).
Southern, Edwin M, and Uwe Maskos. Parallel synthesis and analysis of large numbers of related chemical compounds: applications to oligonucleotides. Journal of biotechnology 35(2-3):217-227 (1994).
Southern. Edwin M, and Uwe Maskos. Parallel Synthesis and Analysis of Large Numbers of Related Chemical Compounds: Applications to Oligonucleotides. Journal of Biotechnology 35(2-3):217-227 (1994). (Abstract Only).
Southern. Edwin M. High-density Gridding: Techniques and Applications. Current Opinion in Biotechnology 7(1):85-88 (1996). (Abstract Only).
Spencer, Sarah J. et al. Massively Parallel Sequencing of Single Cells by epicPCR Links Functional Genes With Phylogenetic Markers. ISME Journal 10(2):427-436 (2016).
Spitzer, Matthew H, and Garry P Nolan. Mass Cytometry: Single Cells, Many Features. Cell 165(4):780-791 (2016).
Stahl, Patrik L. et al. Visualization and analysis of gene expression in tissue sections by spatial transcriptomics. Science 353(6294):78-82 (2016).
Starkuviene, V. and R. Pepperkok. The potential of high-content high-throughput microscopy in drug discovery. British journal of pharmacology 152(1):62-71 (2007).
Steinhilber et al, "A microgel construction kit for bioorthogonal encapsulation and pH-controlled release of living cells," Angew. Chem. Int. Ed., 52: 13538-13543 (2013).
Stickels, Robert R et al. Highly sensitive spatial transcriptomics at near-cellular resolution with Slide-seqV2. Nature biotechnology 39(3):1-7 (2021).
Stickels, Robert R et al. Supplementary Information; Highly sensitive spatial transcriptomics at near-cellular resolution with Slide-seqV2. Nature biotechnology 39(3):1-7 (2021).
Stoeckius, Marlon. et al. Large-scale simultaneous measurement of epitopes and transcriptomes in single cells. Nature methods 14(9):865-868 (2017).
Strategies for Attaching Oligonucleotides to Solid Supports. IDT—Integrated DNA Technologies:1-7 (2014).
Sun, Tao. et al. Image-based single-cell sorting via dual-photopolymerized microwell arrays. Analytical chemistry 86(2):977-981 (2014).
Suri et al, "Solid freeform fabrication of designer scaffolds of hyaluronic acid for nerve tissue engineering," Biomed. Microdevices, 13: 983-993 (2011).
Suyama et al. "Photobase generators: Recent progress and application trend in polymer systems", Progress in Polymer Science, 34(2009), 194-209. (Year: 2008).
Tamminen, Manu V, and Marko PJ Virta. Single Gene-based Distinction of Individual Microbial Genomes From a Mixed Population of Microbial Cells. Frontiers in Microbiology 6:195, 1-11 (2015).
Tamura, et al., Optical cell separation from three-dimensional environment in photodegradable hydrogels for pure culture techniques. Scientific Reports, May 7, 2014; 4:4793, DOI: 10.1038/srep04793.
Tanaka, Masahiro. et al. An unbiased cell morphology-based screen for new, biologically active small molecules. PLoS biology 3(5):e128, 1-13 (2005).
Tanna, Jay G. et al. Critical Testing and Parameters for Consideration When Manufacturing and Evaluating Tumor-associated Antigen-specific T Cells. Cytotherapy 21(3):278-288 (2019).
Tendeiro, Rita. et al. TCR-Modified Cells (2018).
Thakker, Suhani. et al. Array-SeQ: An open array platform that simultaneously profiles genotype and phenotype of single cells. Poster Presented at QuantumCyte p. 1 (2018).
Thibault, C. et al. Direct microcontact printing of oligonucleotides for biochip applications. Journal of Nanobiotechnology. 3:7, 1-12 (2005).
Thiol-Modifier S-S Phosphoramidite and Supports. Glen Research [Retrieved on Jul. 8, 2025] Available at URL: www.glenres.com pp. 1-2.
Thornhill, Alan R. et al. A Comparison of Different Lysis Buffers to Assess Allele Dropout From Single Cells for Preimplantation Genetic Diagnosis. Prenatal Diagnosis 21(6):490-497 (2001).
Tian, Luyi. et al. The Expanding Vistas of Spatial Transcriptomics. Nature Biotechnology 41(6):773-782 (2022).
Tibbit et al, "Hydrogels as extracellular matrix mimics for 3D cell culture," Biotechnology and Bioengineering, 103(4): 655-663 (2009).
Trilling, Anke K. Antibody orientation on biosensor surfaces: a minireview. Analyst 138(6):1619-1627 (2013).

(56) References Cited

OTHER PUBLICATIONS

Tsang et al. Fabrication of 3D hepatic tissues by additive photopatterning of cellular hydrogels. The FASEB Journal 21(3):790-801 (2007).
Tsang. Three-Dimensional Tissue Fabrication, Advanced drug delivery reviews 56(11):1635-1647 (2004).
Tusneem, Nadeem. et al. Quantitation of Replication Competent Viruses using ddPCR. Poster Presented at Q2 Solutions p. 1 (2022).
Tyagarajan et al, "Optimizing CAR-T cell manufacturing processes during pivotal clinical trials," Molecular Therapy: Methods & Clinical Development, 16: 136-144 (2020).
Underhill et al, "Bioengineering methods for analysis of cells in vitro," Ann. Rev. Cell Devel. Biol., 28: 385-410 (2012).
Unger, et al. Monolithic microfabricated valves and pumps by multilayer soft lithography. Science. Apr. 7, 2000;288(5463):113-6.
Unger, Marc A. et al. Monolithic Microfabricated Valves and Pumps by Multilayer Soft Lithography. Science 288(5463):113-116 (2000).
U.S. Appl. No. 17/669,315 Office Action dated Oct. 13, 2023.
U.S. Appl. No. 17/896,742 Office Action dated Sep. 14, 2023.
U.S. Appl. No. 18/219,545 Notice of Allowance dated Jan. 31, 2024.
U.S. Appl. No. 18/219,545 Office Action dated Oct. 18, 2023.
U.S. Appl. No. 17/715,843 Notice of Allowance dated Aug. 31, 2022.
U.S. Appl. No. 17/715,843 Office Action dated Jul. 8, 2022.
U.S. Appl. No. 17/896,742 Office Action dated Mar. 13, 2023.
U.S. Appl. No. 17/896,742 Office Action dated Mar. 22, 2024.
U.S. Appl. No. 17/896,742 Office Action dated Nov. 21, 2022.
U.S. Appl. No. 18/593,787 Non-Final Office Action dated May 7, 2024.
U.S. Appl. No. 18/593,787 Notice of Allowance dated Jul. 11, 2024.
U.S. Appl. No. 18/776,193 Corrected Notice of Allowability dated Apr. 23, 2025.
U.S. Appl. No. 18/776,193 Notice of Allowance dated Jan. 16, 2025.
U.S. Appl. No. 18/776,193 Office Action dated Sep. 16, 2024.
U.S. Appl. No. 18/891,555 Office Action dated Apr. 28, 2025.
U.S. Appl. No. 18/974,436 Office Action dated May 15, 2025.
U.S. Appl. No. 19/177,401 Notice of Allowance dated Aug. 6, 2025.
U.S. Appl. No. 19/177,401 Office Action dated Jul. 1, 2025.
Uszczynska, Barbara. et al. Application of click chemistry to the production of DNA microarrays. Lab on a chip 12(6):1151-1156 (2012).
Valihrach, Lukas. et al. Platforms for single-cell collection and analysis. International journal of molecular sciences 19(3):807, 1-20 (2018).
Van Dam, Robert Michael. Solvent-resistant elastomeric microfluidic devices and applications. Doctoral Thesis, California Institute of Technology :1-334 (2005).
Van Der Vlies, et al., On Demand release and retrieval of bacteria from microwell arrays using photodegradable hydrogel membranes. ACS Appl. Bio Mater. 2019, 2, 266-276.
Vaninsberghe, Michael. et al. Highly multiplexed single-cell quantitative PCR. PLoS ONE 13(1):e0191601, 1-18 (2018).
Venkatesan, Hariharan, and Marc M. Greenberg. Improved Utility of Photolabile Solid Phase Synthesis Supports for the Synthesis of Oligonucleotides Containing 3'-Hydroxyl Termini. The Journal of Organic Chemistry 61(2):525-529 (1996).
Verma, Sandeep et al. Modified Oligonucleotides: Synthesis and Strategy for Users. Annual Review of Biochemistry 67(1):99-134 (1998).
Vickovic et al, "Massive and parallel expression profiling using microarrayed single-cell sequencing," Nature Communications, 7: 13182 (2016).
Vickovic, Sanja et al. High-definition Spatial Transcriptomics for in Situ Tissue Profiling. Nature methods 16(10):987-990 (2019).
Vistain, Luke F. and Savas Tay. Single-Cell Proteomics. Trends in Biochemical Sciences. 46(8):661-672 (2021).
Volozonoka, Ludmila. et al. Whole Genome Amplification in Preimplantation Genetic Testing in the Era of Massively Parallel Sequencing. International Journal of Molecular Sciences 23(9):4819, 1-24 (2022).
Wahlgren, Marie, and Thomas Arnebrant. Protein adsorption to solid surfaces. Trends in Biotechnology 9(1):201-208 (1991).
Walser, Marcel. et al. Novel method for high-throughput colony PCR screening in nanoliter-reactors. Nucleic acids research 37(8):e57, 1-8 (2009).
Wang, Chong. et al. Imaging-based pooled CRISPR screening reveals regulators of IncRNA localization. Proceedings of the National Academy of Sciences of the United States of America 116(22):10842-10851 (2019).
Wang et al, "Broadening cell selection criteria with micropallet arrays of adherent cells," Cytometry Part A, 71A: 866-874 (2007).
Wang et al, "Micromolded arrays for separation of adherent cells," LabChip, 10(21): 2917-2924 (2010).
Wang et al, "Micropallet arrays with poly(ethylene glycol) walls," LabChip, 8(5): 734-740 (2008).
Wang, Xiuyan, and Isabelle Riviere. Clinical Manufacturing of CAR T cells: Foundation of a Promising Therapy. Molecular Therapy Oncolytics 3:16015, 1-7 (2016).
Wang, Xuefeng. et al. DNA copy number profiling using single-cell sequencing. Briefings in Bioinformatics 19(5):731-736 (2018).
Wang, Yong and Navin, Nicholas E. Advances and Applications of Single-Cell Sequencing Technologies. molecular cell 58(4):598-609 (2015).
Wang, Yuchen. et al. Degradable poly (ethylene glycol)(PEG)-based hydrogels for spatiotemporal control of siRNA/nanoparticle delivery. Journal of Controlled Release 287:58-66 (2018).
Wang, Yuli. et al. Broadening cell selection criteria with micropallet arrays of adherent cells. Cytometry Part A: The Journal of the International Society for Analytical Cytology 71(10):866-874 (2007).
Wang, Yuli. et al. Micromolded arrays for separation of adherent cells. Lab on a Chip 10(21):2917-2924 (2010).
Wang, Yuli. et al. Micropallet arrays with poly (ethylene glycol) walls. Lab on a Chip 8(5):734-740 (2008).
Weile, Jochen, and Frederick P. Roth. Multiplexed assays of variant effects contribute to a growing genotype-phenotype atlas. Human genetics 137(9):665-678 (2018).
Weile, Jochen. Extending the Atlas of Variant Effects in Human Disease Genes. University of Toronto (2017).
Welch, Joshua D. et al. Selective single cell isolation for genomics using microraft arrays. Nucleic acids research 44(17):8292-8301 (2016).
Welch, Joshua D. et al. Supplementary Data: Selective single cell isolation for genomics using microraft arrays. Nucleic acids research 44(17):8292-8301 (2016).
Wendeln, Christian, and Bart Jan Ravoo. Surface patterning by microcontact chemistry. Langmuir 28(13):5527-5538 (2012). (Abstract Only).
Wheeler, Emily C. et al. Pooled CRISPR screens with imaging on microraft arrays reveals stress granule-regulatory factors. Nature Methods 17(6):636-642 (2020).
Williams, Cameron G. et al. An introduction to spatial transcriptomics for biomedical research. Genome medicine 14(1):68, 1-18 (2022).
Williams et al, "Variable cytocompatibility of six cell lines with photoinitiators used for polymerizing hydrogels and cell encapsulation," Biomaterials, 26: 1211-1218 (2005).
Winther, Jakob R, and Thorpe, Colin. Quantification of thiols and disulfides. Biochimica et Biophysica Acta (BBA) 1840(2):838-846 (2014).
Woolley, Christine F. et al. Theoretical limitations of quantification for noncompetitive sandwich immunoassays. Analytical and Bioanalytical chemistry 407(28):8605-8615 (2015).
Wu, Han. et al. Patterning Hydrophobic Surfaces by Negative Microcontact Printing and Its Applications. Small 14(38):e1802128 (2018). (Abstract Only).
Xu, Da-Ming. et al. Investigation of lymphocyte subsets in peripheral blood of patients with dyslipidemia. International Journal of General Medicine :5573-5579 (2021).
Xu et al, "Development of disposable PDMS micro cell culture analog devices with photopolymerizable hydrogel encapsulating living cells," Biomed. Microdevices, 14: 409-418 (2012).
Xu, Wei. et al. Microcup arrays for the efficient isolation and cloning of cells. Analytical chemistry 82(8):3161-3167 (2010).

(56) References Cited

OTHER PUBLICATIONS

Yan, Xiaowei. et al. High-content imaging-based pooled CRISPR screens in mammalian cells. Journal of Cell Biology 220(2):e202008158, 1-21 (2021).
Yang et al, "Rapid fabrication of hydrogel microstructures using UV-induced projection printing," Micromachines, 6:1903-1913 (2015).
Yang, Liwei. et al. Deep profiling of cellular heterogeneity by emerging single-cell proteomic technologies. Proteomics 20(13):1900226, 1-12 (2020). Published Online Dec. 2, 2019.
Yasar, et al. We have to solve barcode patterning to capture single cell mRNA!!! Cellanome 68 pages (2021).
Yenkin, Alex L. et al. Mitochondrial Phenotypes Distinguish Pathogenic MFN2 Mutations by Pooled Functional Genomics Screen. bioRxiv preprint:1-61 (2021).
Yin, H. B. et al. Chemical modification and micropatterning of Si (1 0 0) with oligonucleotides. Microelectronic Engineering 73:830-836 (2004). (Abstract Only).
Yin, Yi. et al. High-Throughput Single-Cell Sequencing with Linear Amplification. Molecular Cell 76(4):676-690.e10 (2019).
Yom-Tov, Ortal. et al. PEG-Thiol based hydrogels with controllable properties. European Polymer Journal 74:1-12 (2016).
Yu, Zhilong. et al. Microfluidic Whole Genome Amplification Device for Single Cell Sequencing. Analytical Chemistry 86(19):9386-9390 (2014).
Yuan, Jinzhou, and Peter A. Sims. An automated microwell platform for large-scale single cell RNA-seq. Scientific reports 6(1):33883, 1-10 (2016).
Yuan, Jinzhou, and Peter A Sims. An Automated Microwell Platform for Large-Scale Single Cell RNA-Seq. Scientific Reports 6:33883, 1-10 (2016).
Zalipsky, Samuel, and J. Milton Harris. Introduction to Chemistry and Biological Applications of Poly (ethylene glycol). American Chemical Society :1-13 (1997).
Zanella, Fabian. et al. High content screening: seeing is believing. Trends in biotechnology 28(5):237-245 (2010).
Zare, Richard N., and Samuel Kim. Microfluidic platforms for single-cell analysis. Annual review of biomedical engineering 12(1):187-201 (2010).
Zarrinkar, Patrick P. et al. Arrays of Arrays for High-Throughput Gene Expression Profiling. Genome Research 11:1256-1561 (2001).
Zborowski, Maciej, and Jeffrey J. Chalmers. Rare cell separation and analysis by magnetic sorting. analytical Chemisry:8050-8056 (2011).
Zguris et al, "A novel single-step fabrication technique to create heterogeneous poly(ethylene glycol) hydrogel microstructures containing multiple phenotypes of mammalian cells," Langmuir, 21: 4168-4174 (2005).
Zhang et al, "Rapid fabrication of complex 3D extracellular microenvironments by dynamic optical projection stereolithography," Adv. Mater., 24(310: 4266-4270 (2012).
Zhang, Lin. et al. Whole Genome Amplification From a Single Cell: Implications for Genetic Analysis. Proceedings of the National Academy of Sciences of the United States of America 89(13):5847-5851 (1992).
Zhang, Shiyun. et al. Predicting detection limits of enzyme-linked immunosorbent assay (ELISA) and bioanalytical techniques in general. Analyst 139(2):439-445 (2014).
Zhao, Zhao et al. Organizing DNA Origami Tiles into Larger Structures Using preformed scaffold Frames. Nano letters 11(7):2997-3002 (2011).
Zhou, et al. Encoding Method of Single-cell Spatial Transcriptomics Sequencing. International Journal of Biological Sciences 16.14 (2020): 2663-2674.
Zhu, He. et al. A Miniature Cytometry Platform for Capture and Characterization of T-lymphocytes from Human Blood. Analytica Chimica Acta 608(2):186-196 (2008). Online published Dec. 28, 2007.
Zhu, Y Y. et al. Reverse Transcriptase Template Switching: a SMART Approach for full-length cDNA library Construction. BioTechniques 30(4):892-897 (2001).
Zhuang, Ziyun, and Ho Pui Ho. Application of digital micromirror devices (DMD) in biomedical instruments. Journal of Innovative Optical Health Sciences 13(06):2030011, 1-22 (2020).
Zong et al. Genome-Wide Detection of Single Nucleotide and Copy-Number Variations of a Single Human Cell. Science 338(6114):1622-1626 (2012).
Antona, S. et al. Droplet-based combinatorial assay for cell cytotoxicity and cytokine release evaluation. Advanced Functional Materials. 30(46):003479 (2020).
Subedi, N. et al. An automated real-time microfluidic platform to probe single NK cell heterogeneity and cytotoxicity on-chip. Scientific Reports. 11(1):17084 (2021).
EP Application No. 23775564.0 Extended European Search Report dated Mar. 4, 2026.

* cited by examiner

Steps of Exemplary CAR T-Cell Development and Therapy

Exemplary Single Cell Assays Combinations
Within the Same Channel

[From Fig. 2E]

Add protein-detection antibodies
(255)

Count and/or quantify beads
With fluorescent signals
(256)

Wash to remove protein detection antibodies;
Perform steps of Fig. 2B:
Load cell surface antibodies with oligo labels
Release & capture labels;
Depolymerize;
Sequence captured labels
(260)

Treat with restriction endonuclease (444)

Ligate adaptors;
Amplification of adaptored strands followed by elution and off-instrument sequencing; or
Melt captured strands; perform bridge PCR and cluster formation followed by on-instrument sequencing (446)

METHODS FOR ENCLOSING AND ANALYZING A CELL IN A FLUIDIC DEVICE

CROSS-REFERENCE

This application is a continuation of U.S. patent application Ser. No. 18/891,555, filed Sep. 20, 2024, which is a continuation of International Patent Application No. PCT/US2023/015806, filed Mar. 21, 2023, which claims the benefit of U.S. Provisional Application No. 63/322,601, filed Mar. 22, 2022, each of which are incorporated herein by reference in entirety.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BACKGROUND

Engineered cell-based therapeutics provide promising new approaches to treating complex diseases because of a cell's ability to sense and integrate a wide range of signals, to actively move to specific tissue compartments, and to actuate context-dependent responses, e.g. Fischbach et al, Science Transl. Med., 5: 1797 (2013). Such cell-based approaches provide novel therapeutic devices that address current obstacles faced by small molecules and biologics, such as poor target specificity, undesirable tissue compartment localization, a lack of personalization, and limited potential for the effects of the drug to be modified once administered to a patient, either over space and time, or in response to a changing clinical picture. These issues can reduce the pharmaceutical utility of such compounds. Cytotoxic lymphocytes (CLs), such as cytotoxic T-lymphocytes (CTLs) and Natural Killer cells (NKs), are an excellent platform for engineering cell-based therapeutic systems for several reasons: (i) cytotoxic lymphocytes possess a unique delivery-cell-to-target-cell molecular transfer system in the granzyme-perforin pathway; (ii) T-cell receptors (TCRs), or the related chimeric antigen receptors (CARs), endow cytotoxic lymphocytes with an exquisite level of specificity in targeting a cell population presenting Major Histocompatibility Complex (MHC) bound cognate antigen or, in the case of CARS, an arbitrary surface antigen; (iii) activated cytotoxic lymphocytes differentially express cytokine and tissue specific receptors, enabling selective lymphocyte homing throughout the body to target tissue; and (iv) laboratory and clinical protocols for lymphocyte modification and therapeutic administration have been developed in the field of adoptive cell therapy, e.g., Restifo et al, Nature Reviews Immunology, 12: 269-281 (2012). In view of these advantages and positive clinical results, a host of cell-based therapies have been approved to treat a range of cancers and other disorders.

However, along with the successes of cell-based therapies there are significant development, manufacturing and quality assurance challenges due to the complexities of using living organisms as drugs. Tests must be carried out for selecting an appropriate cellular subpopulation to engineer and for assuring at each step of the manufacturing process that there is no deleterious change in the identity, purity, or operability of the engineered subpopulation, e.g. Tanna et al, Cytotherapy, 21: 278-288 (2019); Wang et al, Molecular Therapy, 3: 16015 (2016); Levine et al, Molecular Therapy: Methods & Clinical Development, 4: 92-101 (2017). Accordingly, the field of cell-based therapies would be advanced by the availability of a cellular analysis platform, including methods and systems, for performing a wide range of highly multiplexed cellular assays relevant to the development and manufacture of cell-based therapeutics.

SUMMARY OF THE INVENTION

The invention is directed to methods and systems for performing large-scale multiplexed single cell assays, particularly for characterizing populations engineered cells developed for medical or industrial applications, such as cell-based therapeutics. Exemplary single cell assays include, but are not limited to, cytotoxicity, proliferative capacity, activation status, vector copy number and insertion site analysis of transformed cells, and the like.

In an aspect, provided herein is a method of determining one or more cellular characteristics, the method comprising: (a) synthesizing one or more hydrogel chambers, wherein a hydrogel chamber of the one or more hydrogel chambers encloses a cell disposed on a surface of a channel; (b) lysing the cell so that genomic DNA of the cell is released into its hydrogel chamber; (c) amplifying the genomic DNA of the cell, thereby obtaining amplified genomic DNA; and (d) using the amplified genomic DNA, measuring a viral copy number, a viral integration site, or a genomic copy number variation of the cell.

In some cases, the measuring further comprises (i) annealing a vector-specific-primer to the amplified genomic DNA, (ii) extending the vector-specific primer, thereby obtaining an extension product comprising a copy of a segment of the genomic DNA, and (iii) identifying, from the segment, one or more sites of integration of the vector-specific-primer with the genomic DNA. In some cases, the cell is a mammalian cell, and the measuring further comprises: (i) sequencing one or more fragments of the amplified genomic DNA, thereby obtaining sequences of the one or more fragments; and (ii) determining a genomic copy number variation for the cell from the sequences of the one or more fragments. In some cases, the sequencing comprises acquiring a sequence coverage of the amplified genomic DNA of 0.25× or greater. In some cases, the determination of the genomic copy number variation has a resolution of 3 megabases or higher.

In another aspect, provided herein is a method of determining one or more cellular characteristics of one or more cells, the method comprising: (a) providing a fluidic device comprising (i) a channel comprising a first surface, the one or more cells, and one or more polymer precursors, wherein the one or more cells are disposed on or adjacent to the first surface, (ii) a spatial energy modulating element in optical communication with the first surface, and (iii) a detector; (b) identifying a position of the one or more cells in the channel with the detector; (c) using the spatial energy modulating element, projecting energy into the channel such that the projected energy causes the one or more polymer precursors to form polymer matrix walls of one or more chambers, wherein the one or more chambers at least partially enclose the one or more cells at the position identified by the detector; (d) loading the channel with one or more assay reagents; and (e) incubating the one or more cells under assay conditions to generate signals from the one or more chambers that are indicative of one or more cellular characteristics of cells enclosed thereby.

In some cases, (i) the one or more cellular characteristics comprise proliferation rate, (ii) the incubating under the assay conditions comprise incubating under growth conditions, and (iii) the method further comprises, after the incubating, determining a proliferation rate of the one or more cells at least partially enclosed by the one or more chambers. In some cases, the determining of the proliferation rate comprises counting the one or more cells at least partially enclosed by of the one or more chambers. In some cases, the one or more cellular characteristics further comprise a profile of cell membrane proteins, and the method further comprises incubating the one or more cells with antibodies each specific for a different cell surface protein whose relative expression permits identification of the one or more cells, and each of such antibodies has a distinct label. In some cases, the first surface comprises one or more capture elements for capturing one or more assay components or one or more components of the one or more cells. In some cases, each of the antibodies has an oligonucleotide label comprising an antibody-specific barcode capable of being captured by the one or more capture elements.

In some cases, the method further comprises: (i) providing the oligonucleotide labels, wherein the oligonucleotide labels are attached to the antibodies by a scissile linkage; (ii) loading the channel with a releasing reagent to cleave the scissile linkage so that the oligonucleotide labels are released and captured by the capture elements; (iii) copying the captured oligonucleotide labels to produce complementary DNAs thereof; and (iv) sequencing the complementary DNAs to identify the captured oligonucleotide labels.

In some cases, the first surface comprises one or more capture elements for capturing one or more assay components or components of the one or more cells, wherein the one or more cellular characteristics further includes cellular transcriptomes, and the method further comprises (i) loading the channel with a lysing reagent so that messenger RNAs of the one or more cells are released and captured by the one or more capture elements, (ii) loading the channel with reverse transcription reagents to copy the captured messenger RNAs to produce complementary DNAs, and (iii) sequencing the complementary DNAs.

In some cases, (i) the one or more cellular characteristics further include a profile of proteins secreted by the one or more cells, (ii) the channel further comprises a protein-capture surface comprising protein affinity reagents that bind the proteins secreted by the one or more cells, and (iii) the method further comprises using an amount of labeled protein detection antibodies to detect the proteins secreted by the one or more cells that are bound to the protein-capture surface adjacent to the one or more cells.

In some cases, (i) the one or more cellular characteristics comprises cytotoxicity, (ii) the first surface comprises target cells disposed thereon, (iii) the method further comprises loading the channel with effector cells so that the effector cells are disposed on or adjacent to the first surface, (iv) the step of incubating comprises incubating the effector cells and the target cells with a vital stain that generates an optical signal in dead cells but not living cells; and (v) counting dead cells in each of the one or more chambers to determine a cytotoxicity value of the effector cell enclosed thereby. In some cases, the first surface comprises one or more capture elements for capturing one or more assay components or one or more components of the one or more cells. In some cases, the one or more cellular characteristics further comprise a profile of cell membrane proteins, and the method further comprises incubating the one or more cells with antibodies each specific for a different cell surface protein whose relative expression permits identification of the cells, and each of such antibodies has a different label. In some cases, each of the antibodies has an oligonucleotide label comprising an antibody-specific barcode capable of being captured by the one or more capture elements. In some cases, the method further comprises (i) providing the oligonucleotide labels, wherein the oligonucleotide labels are attached to the antibodies by a scissile linkage; (ii) loading the channel with a releasing reagent to cleave the scissile linkage so that the oligonucleotide labels are released and captured by the capture elements; (iii) copying the captured oligonucleotide labels to produce complementary DNAs thereof; and (iv) sequencing the complementary DNAs to identify the captured oligonucleotide labels.

In some cases, the first surface comprises one or more capture elements for capturing one or more assay components or components of the one or more cells, wherein the one or more cellular characteristics further includes cellular transcriptomes, and the method further comprises (i) loading the channel with a lysing reagent so that messenger RNAs of the one or more cells are released and captured by the one or more capture elements, (ii) loading the channel with reverse transcription reagents to copy the captured messenger RNAs to produce complementary DNAs, and (iii) sequencing the complementary DNAs. In some cases, (i) the one or more cellular characteristics further include a profile of proteins secreted by the one or more cells, (ii) the channel further comprises a protein-capture surface comprising protein affinity reagents that bind the proteins secreted by the one or more cells, and (iii) the method further comprises using an amount of labeled protein detection antibodies to detect the proteins secreted by the one or more cells that are bound to the protein-capture surface adjacent to the one or more cells.

In some cases, the one or more cellular characteristics comprises copy numbers of one or more nucleotide sequences in genomic DNA of the one or more cells, and the method further comprises: (a) lysing the one or more cells to release the genomic DNA; (b) amplifying the one or more nucleotide sequences, thereby obtaining one or more amplified nucleotide sequences; (c) capturing the amplified one or more nucleotide sequences with one or more capture elements disposed on the channel; (d) copying the captured one or more amplified nucleotide sequences to produce complementary DNAs thereof; and (e) sequencing the complementary DNAs to identify the copy numbers of the one or more nucleotide sequences. In some cases, the one or more nucleotide sequences are each barcodes. In some cases, the barcodes each comprise a unique molecular identifier. In some cases, the unique molecular identifiers identify virus DNA integrated into the genomic DNA, and a number of different the unique molecular identifiers identified in a single cell indicates a viral copy number for such single cell.

In some cases, the one or more cellular characteristics comprises copy numbers of one or more nucleotide sequences in genomic DNA of the one or more cells, and the method further comprises: (a) lysing the one or more cells to release genomic DNA; (b) loading the channel with amplification reagents that generate a signal proportional to a copy number of the one or more nucleotide sequences; (c) amplifying the one or more nucleotide sequences to generate an optical signal proportional to the copy number of the one or more nucleotide sequences. In some cases, amplification reagents are quantitative PCR reagents, and the signal is an optical signal. In some cases, (i) the first surface comprises bridge PCR primers, (ii) the amplification reagents comprise bridge PCR reagents, and (iii) the signal is a number of clusters formed by bridge PCR. In some cases, the amplification reagents comprise rolling circle amplification reagents, and the signal is a number of DNA nanoballs.

In some cases, the one or more cells are randomly disposed on the first surfaces. In some cases, each of the one or more chambers encloses a single cell of the one or more cells. In some cases, the one or more cells comprise cells transduced by a vector, and the one or more cellular characteristics comprise vector integration sites of the cells transduced by the vector, and the method further comprises: (a) lysing the cells transduced by the vector to release genomic DNA of each cell into its respective chamber; (b) amplifying the released genomic DNA; (c) annealing a vector-specific primer to the amplified genomic DNA, (d) extending the vector-specific primer, thereby obtaining an extension product comprising a copy of a segment of the genomic DNA, and (e) identifying from the segment, one or more sites of integration of the vector-specific-primer with the genomic DNA.

In some cases, the one or more cells are mammalian cells and the one or more cellular characteristics comprise genomic copy number variation, and the method further comprises: (a) lysing the one or more cells to release genomic DNA of each cell into its respective chamber; (b) amplifying the released genomic DNA; (c) sequencing fragments of the amplified genomic DNA, thereby obtaining sequences of the genomic DNA fragments; and (d) determining the genomic copy number variation for each cell from the sequences of the genomic DNA fragments. In some cases, the sequencing comprises acquiring a sequence coverage of the genomic DNA fragments of 0.25× or greater, and the determination of the genomic copy number variation has a resolution of 3 megabases or higher.

In another aspect, provided herein is a system for measuring single cell characteristics of a population of cells, the system comprising: (a) one or more channels each comprising a surface, a plurality of cells disposed on the surface, and one or more polymer precursors; (b) at least one spatial energy modulating element in optical communication with the surface of each channel; (c) at least one detector in optical communication with the surface of each channel and in operable association with at least one spatial energy modulating element, wherein the detector is configured to detect each of the plurality of cells and determine a position thereof on the surface of at least one channel; and (d) a plurality of gel chambers in each channel, wherein each gel chamber encloses one or more cells of the plurality of cells, wherein the gel chambers are synthesized by projecting light into the channel with the at least one spatial energy modulating element such that the projected light causes the one or more polymer precursors to form polymer matrix walls of the gel chambers, and wherein the positions of the synthesized chambers are determined at partially by the positions of the cells enclosed thereby identified by the detector.

In some cases, the gel chambers are disposed randomly on at least one of the surfaces. In some cases, each of the gel chambers encloses a single cell. In some cases, the polymer matrix walls are permeable to molecules having a molecular weight less than 3×106 Daltons and are impermeable to molecules having a molecular weight greater than 3×106 Daltons. In some cases, the polymer matrix walls are permeable to molecules having a molecular weight less than 3×105 Daltons and are impermeable to molecules having a molecular weight greater than 3×105 Daltons. In some cases, the polymer matrix walls are permeable to molecules having a molecular weight less than 3×104 Daltons and are impermeable to molecules having a molecular weight greater than 3×104 Daltons. In some cases, the polymer matrix walls are permeable to molecules having a molecular weight less than 3×103 Daltons and are impermeable to molecules having a molecular weight greater than 3×103 Daltons.

In some cases, the gel chambers are degradable hydrogel chambers. In some cases, the gel chambers are hollow and enclose an area of the surface. In some cases, the surfaces comprise capture elements configured to capture nucleic acids.

In another aspect, provided herein is a method of determining one or more cellular characteristics of one or more cells, the method comprising: (a) providing a fluidic device comprising (i) a channel comprising a first surface, the one or more cells, and one or more polymer precursors, wherein the one or more cells are disposed on or adjacent to the first surface, (ii) a spatial energy modulating element in optical communication with the first surface, and (iii) a detector; (b) identifying a position of the one or more cells in the channel with the detector; (c) using the spatial energy modulating element, projecting energy into the channel such that the projected energy causes the one or more polymer precursors to form polymer matrix walls of one or more chambers, wherein the one or more chambers at least partially enclose the one or more cells at the position identified by the detector; and (d) performing one or more assays on the one or more cells in the channels to determine the one or more cellular characteristics, wherein the one or more cellular characteristics are selected from the group consisting of cytotoxicity, viability, proliferation rate, phenotype, vector copy number, vector integration sites, transcriptome, and genomic copy number variation. In some cases, the fluidic device further comprises a plurality of channels, and the performing one or more assays comprises performing a plurality of the assays, wherein each different assay of the one or more assays is performed in a different channel of the plurality of channels.

BRIEF DESCRIPTIONS OF THE DRAWINGS

FIG. 1A diagrammatically illustrates the processing steps in an exemplary cell-based therapy, such as, autologous CAR-T cell therapy.

FIG. 1B contains a table listing combinations of assays that may be performed in accordance with the invention.

Figure 5A:
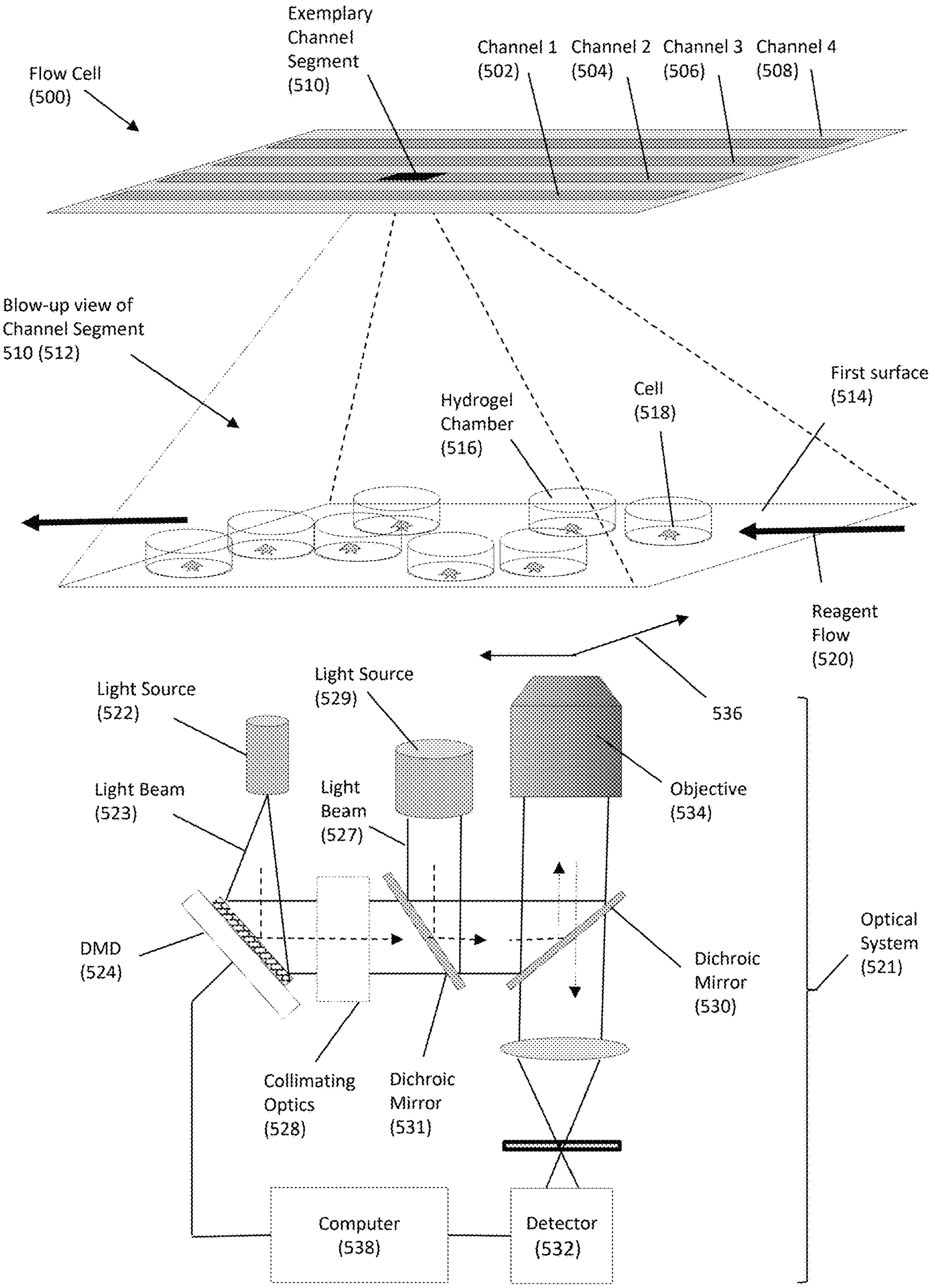
Figure 5B:
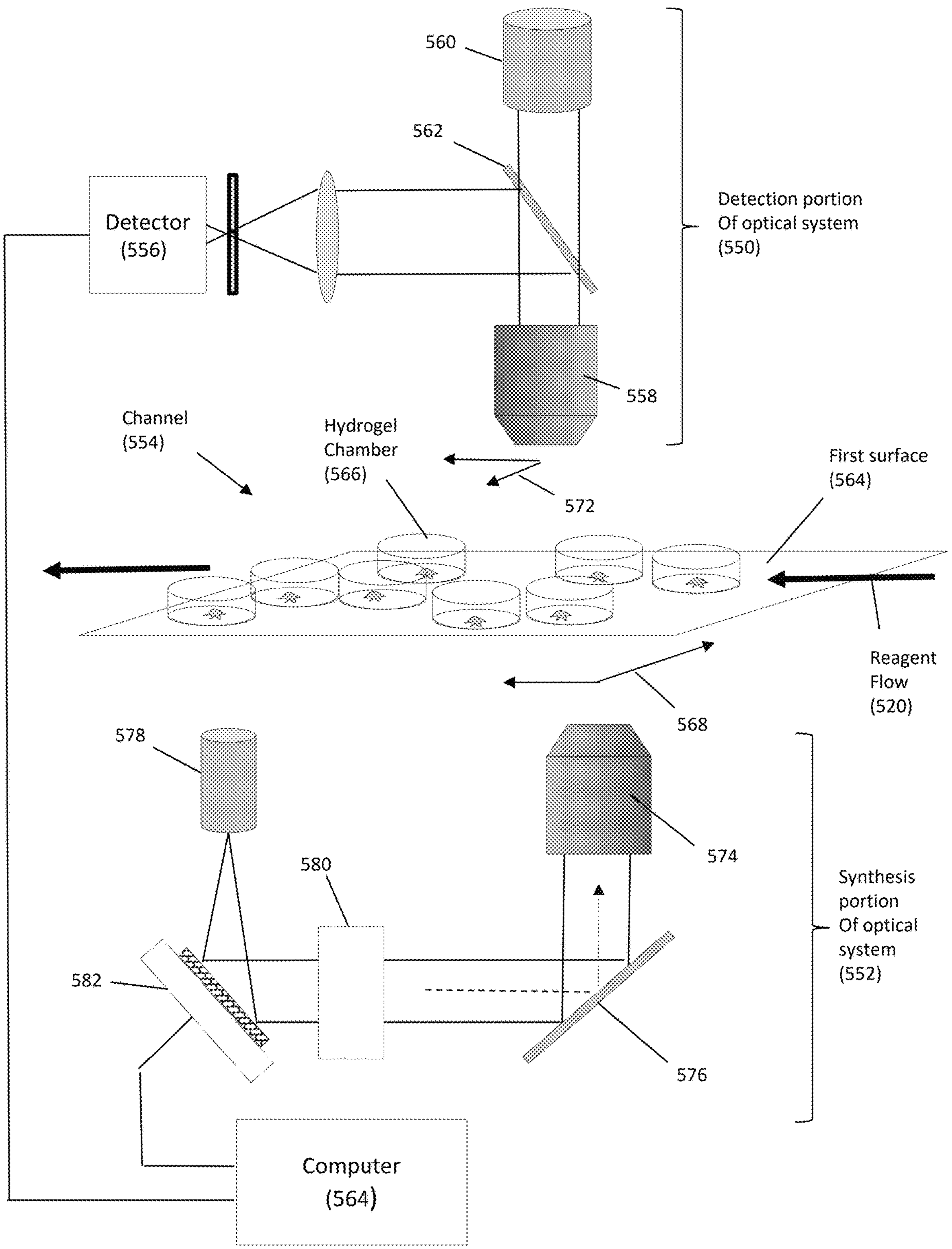

FIGS. 5A-5B diagrammatically illustrate embodiments of systems for carrying out methods of the invention.

Figure 6A:
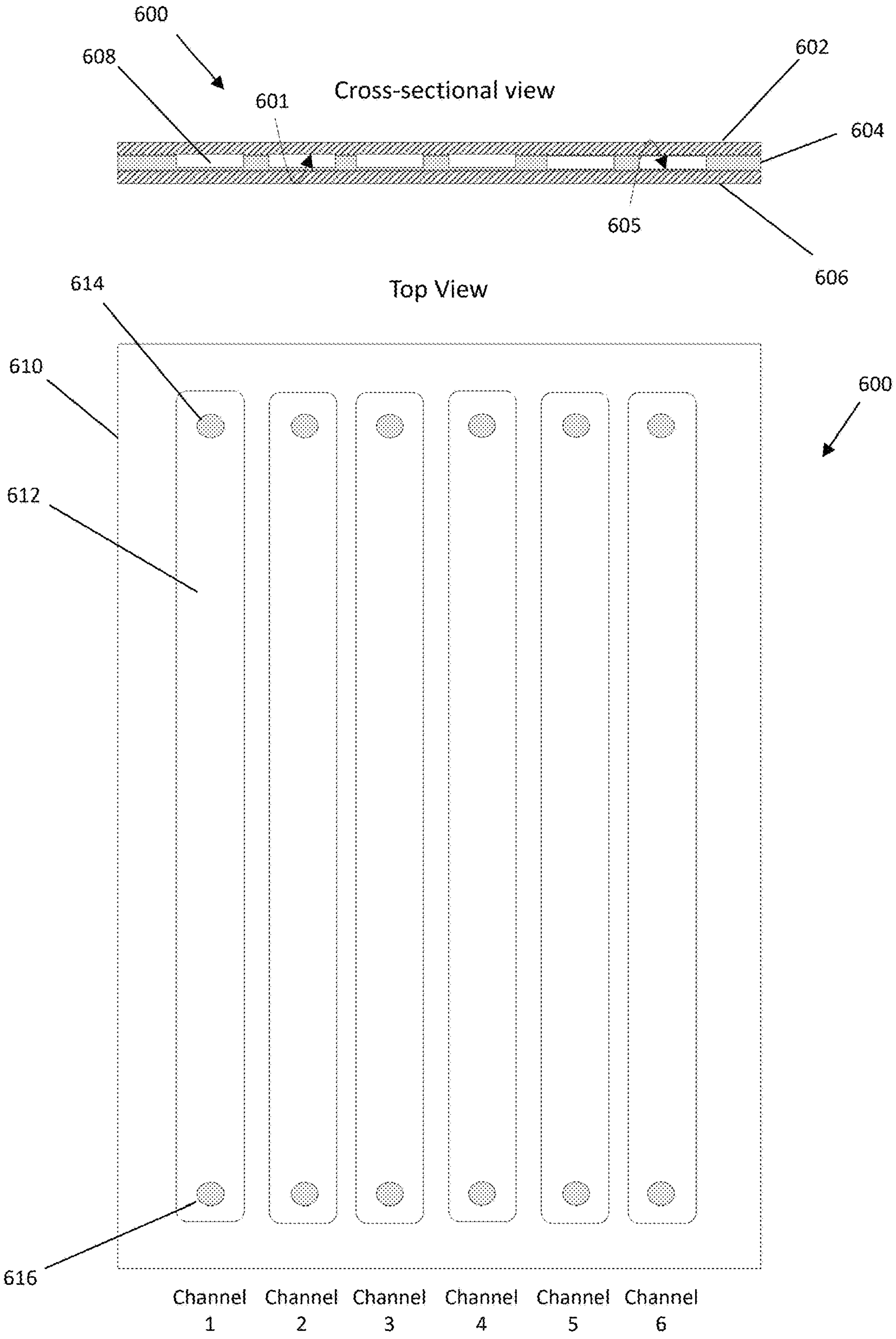
Figure 6B:
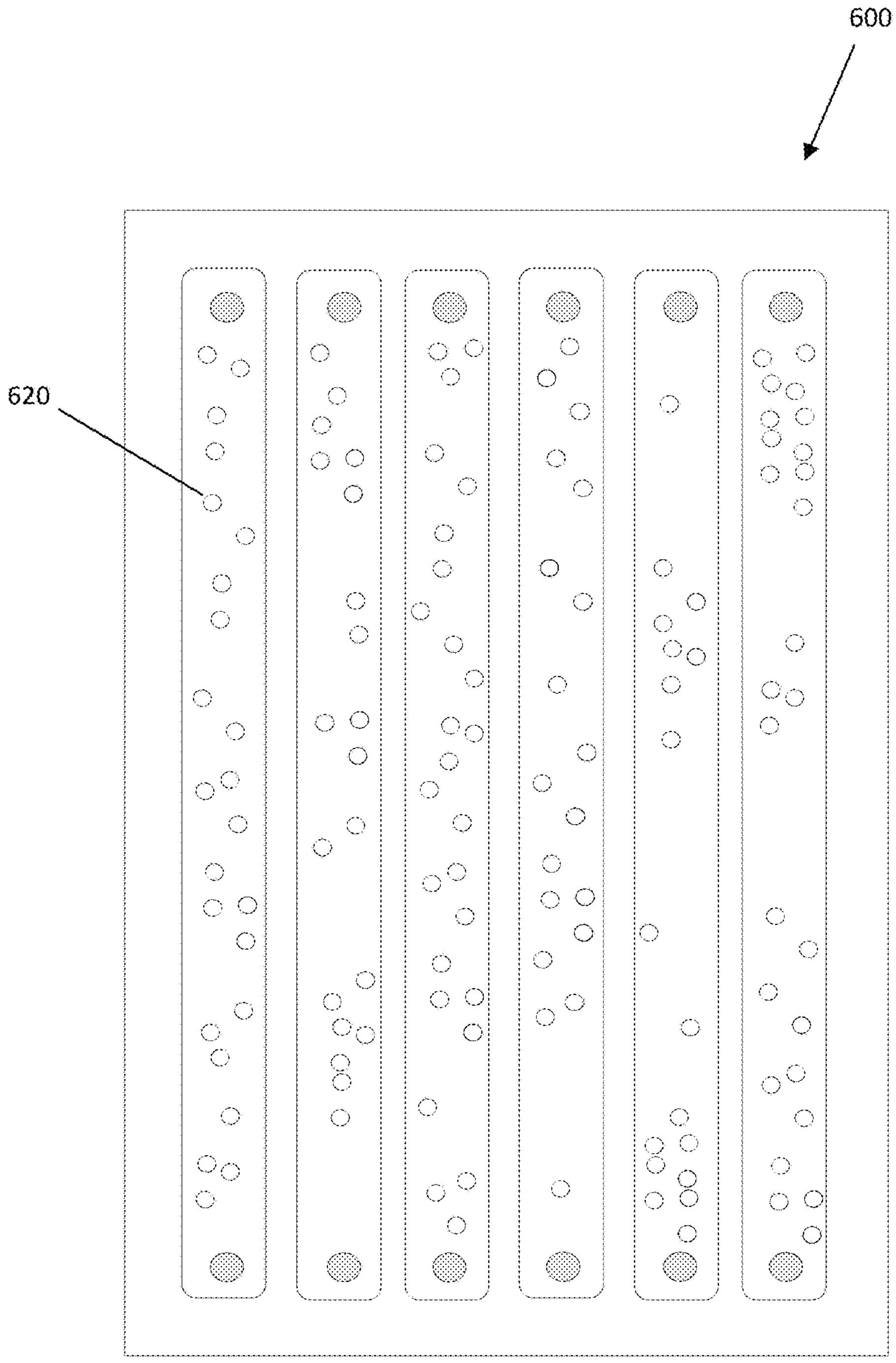

FIGS. 6A-6B illustrate one embodiment of a flow cell comprising a plurality of channels.

Figure 7A:
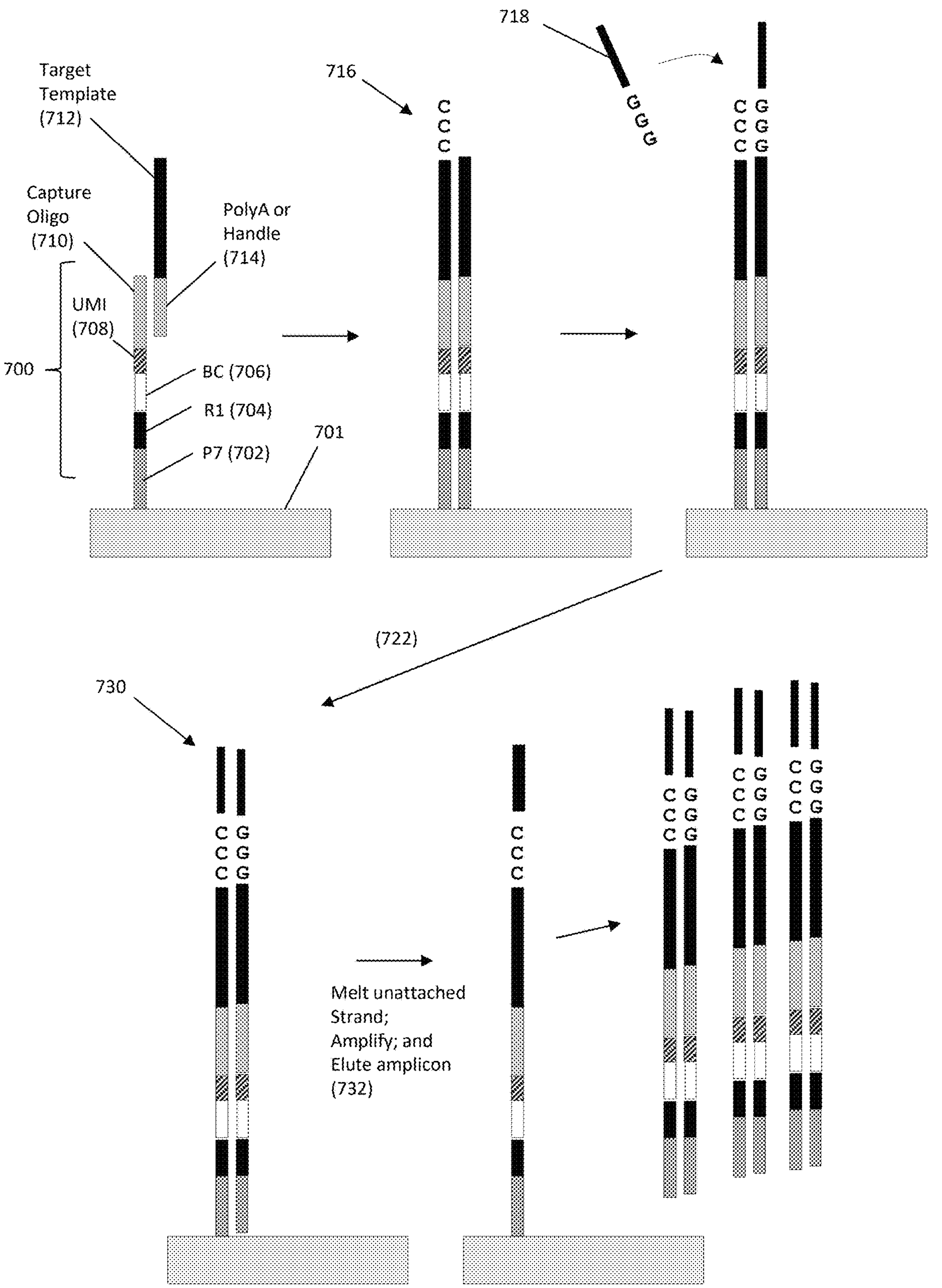
Figure 7B:
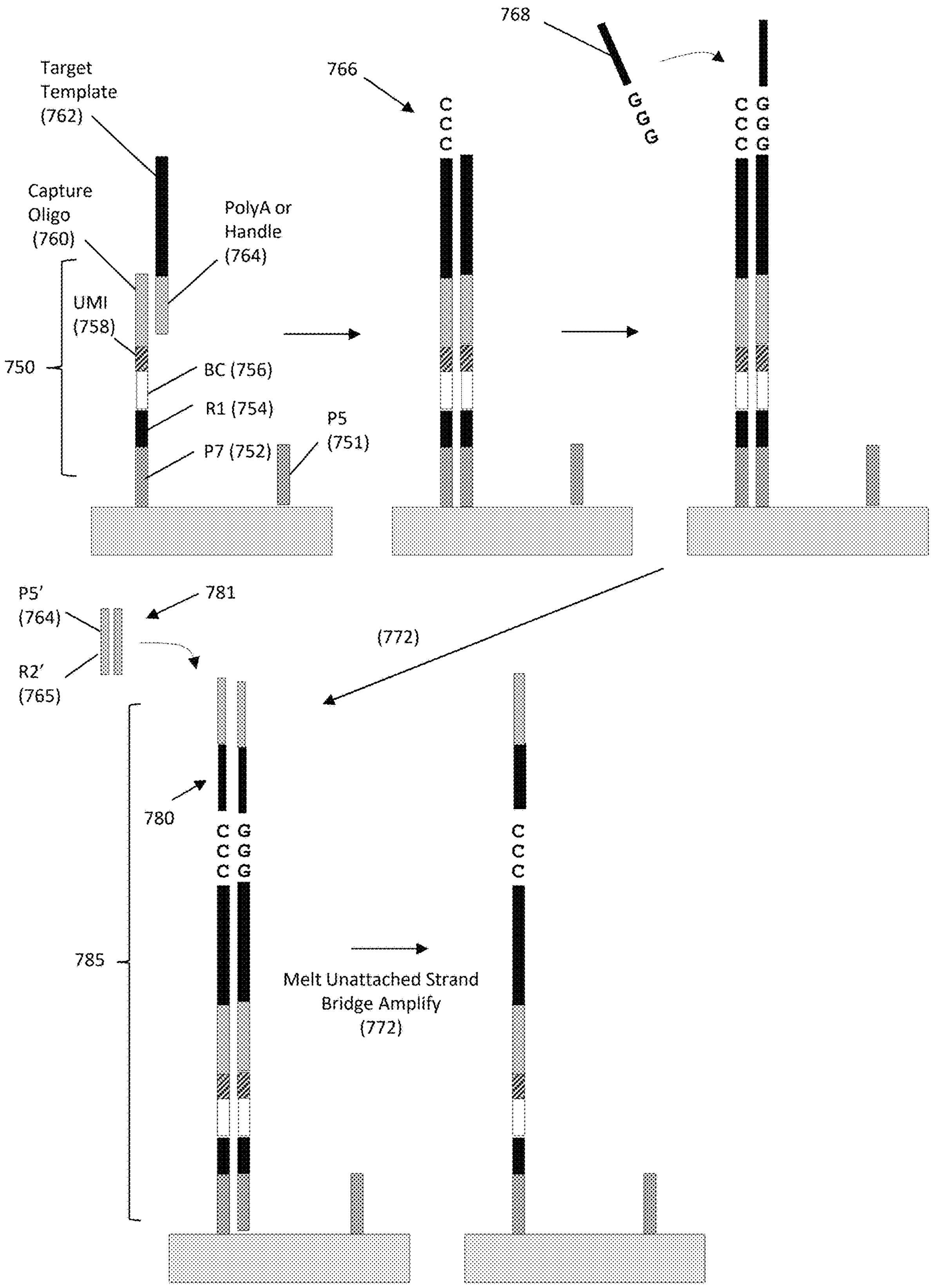

FIGS. 7A-7B illustrate exemplary steps for preparing cDNAs from single cell target templates, such as mRNA, and its sequencing either at the site of a hydrogel chamber ("in situ" or "internal" sequencing) or in an external sequencing instrument after elution from a channel.

DETAILED DESCRIPTION

The practice of the present invention may employ, unless otherwise indicated, conventional techniques and descriptions of organic chemistry, molecular biology (including recombinant techniques), cell biology, and biochemistry, which are within the skill of the art. Such conventional techniques include, but are not limited to, preparation of synthetic polynucleotides, monoclonal antibodies, antibody display systems, cell and tissue culture techniques, nucleic acid sequencing and analysis, and the like. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV); PCR Primer: A Laboratory Manual; Retroviruses; and Molecular Cloning: A Laboratory Manual (all from Cold Spring Harbor Laboratory Press); Renault and Duchateau, Editors, Site-directed Insertion of Transgenes (Springer, Heidelberg, 2013); Lutz and Bornscheuer, Editors, Protein Engineering Handbook (Wiley-VCH, 2009); and the like. Guidance for selecting materials and components to carry out particular functions may be found in available treatises and references on scientific instrumentation including, but not limited to, Moore et al, Building Scientific Apparatus, Third Edition (Perseus Books, Cambridge, MA); Hermanson, Bioconjugate Techniques, 3rd Edition (Academic Press, 2013); and like references.

The present invention is directed to methods and systems for carrying out one or more large-scale multiplexed assays that assess concurrently multiple characteristics of cells, especially for the purpose of developing, and assuring the quality of, cell-based therapeutics. In some embodiments, the invention comprises methods and a system for carrying out concurrently a plurality of assays to determine multiple cellular characteristics important for cell-based therapies including, but not limited to, cell-based therapies for treating cancers, e.g. using CAR-T cells, or cell-based therapies for treating other conditions, such as, spinal injury, stroke, diabetes, e.g. using induced pluripotent stem cells, mesenchymal stem cells, embryonic stem cells, or the like. In some embodiments, the invention is directed to systems for carrying out concurrently a plurality of single cell assays designed to detect or measure selected or predetermined cell characteristics of populations of cells. In some embodiments, one or more of such cellular assays depend on or utilize hydrogel chambers (sometimes referred to herein as "analysis chambers," or simply "chambers," or "hydrogel cages"). In some embodiments, such cellular assays are single cell assays so that one or more hydrogel chambers employed in such assays each enclose only a single cell. In some embodiments, such single cell assays may comprise a single engineered cell and one or more target cells, that is, one or more cells that may be acted on (e.g. killed) by the engineered cell.

"Cells" that may be assayed by methods and systems of the invention comprise any biological cells including, but not limited to, vertebrate, non-vertebrate, eukaryotic, mammalian, microbial, protozoan, prokaryotic, bacterial, insect, or fungal cells. In some embodiments, mammalian cells are assayed by methods and systems of the invention. In particular, any population of mammalian cells which may be, or have been, induced, treated, modified or genetically altered (i.e. genetically engineered) for use in a medical, industrial, environmental, or remedial process, may be analyzed by methods and systems of the invention. In some embodiments, "cells" as used herein comprise genetically modified mammalian cells. In some embodiments, "cells" comprise stem cells that have been induced to differentiate. In some embodiments, "cells" refer to cells modified by CRISPR Cas9 techniques. In some embodiments, "cells" refer to cells of the immune system including, but not limited to, cytotoxic T lymphocytes, regulatory T cells, CD4+ T cells, CD8+ T cells, natural killer cells, antigen-presenting cells, or dendritic cells. Of special interest are cytotoxic T lymphocytes engineered for therapeutic applications, such as cancer therapy.

As used herein, the term "assay" refers to a process for detecting or measuring a cellular characteristic or property of single cells or of a population of cells. Typically process steps of an assay comprise a chemical, biochemical or molecular reaction (such as a cleavage of a bond, specific binding of complementary components, enzyme reactions, dissolution of complementary components, or the like) or a change of physical state (such as an increase or decrease in temperature, change in energy level, or the like) and result in the generation of a signal (or signals) from which the presence, absence or magnitude of a quantity related to a cell may be inferred. The nature of the signal produced by an assay may vary widely and can include, but is not limited to, an electrical signal, an optical signal, a chemical signal, or a material signal. A material signal comprises the production of a material that comprises information that can be extracted. For example, a material signal may be the amplification of a polynucleotide whose length, quantity, composition, or nucleotide sequence is indicative of a cellular characteristic. For example, a barcode oligonucleotide may be a material signal. Characteristics or properties of cells that are detected or measured may vary widely and include, but are not limited to, cytotoxicity, viability, proliferation capacity under selected conditions, size, shape, motility, types and profiles of cell surface, or cell membrane proteins, types and profiles of secreted proteins, production of metabolites, transcriptome, gene copy numbers, gene or allele identity, chromatin accessibility profiles, vector copy numbers for engineered or infected cells, and the like. Assays of special interest for cell-based therapy include, but are not limited to, measurement of characteristics listed in Table 1.

TABLE 1

| Assay | Comments |
|---|---|
| Cytotoxicity | Ability to kill target cells |
| Viability | Fraction of dead cells |
| Proliferation rate | Rate of "expansion" or population growth, especially of desired cell type |
| Phenotype | For example, based on cell surface markers, secreted proteins, structural features (e.g. as determined from images), and the like |
| Cellular morphology | For example, as determined from images |
| Identity | Confirmation that cells are the from patient (autologous) or from the same donor (allogenic) |

TABLE 1-continued

| Assay | Comments |
|---|---|
| Purity | For example, fraction of total population of cells that consist of the desired type (e.g. CD8+ T cells); absence of contaminants, e.g. mycoplasma, fungus, bacteria, etc. |
| Activation | Proliferation and differentiation characteristic of an immune response, usually after specific treatment to stimulate such response |
| Transduction efficiency | For example, fraction of cells of the desired type that incorporate at least one vector (e.g. encoding a CAR or other feature, either epigenetically or by integration into the cell genome) |
| Vector copy number | Number of separate integrations of a vector into a therapeutic cell's genome |
| Integration site analysis | Positions in therapeutic cell's genome where vector has integrated |
| Chromatin accessibility profile | For example, to determine whether transposase-accessible chromatin falls within expected ranges, e.g. both in regard to magnitude and specific locations |
| Transcriptome | Gene expression profile |
| Epigenetic profile | For example, for transiently transfected cells |
| Suicide gene function | For example, to kill and eliminate therapeutic cells in the event of deleterious side effects |
| Genetic stability | Measurement of genomic copy number variation |
| Replicative competent retrovirus | Measure presence or absence of viral replication components in, for example, a transduced therapeutic cells |
| Dose | For example, for CAR T-cells, number of viable T cells expressing CAR (may be expressed as either a total number, a concentration or a number per kg of patient body weight) |

Figure 1A:
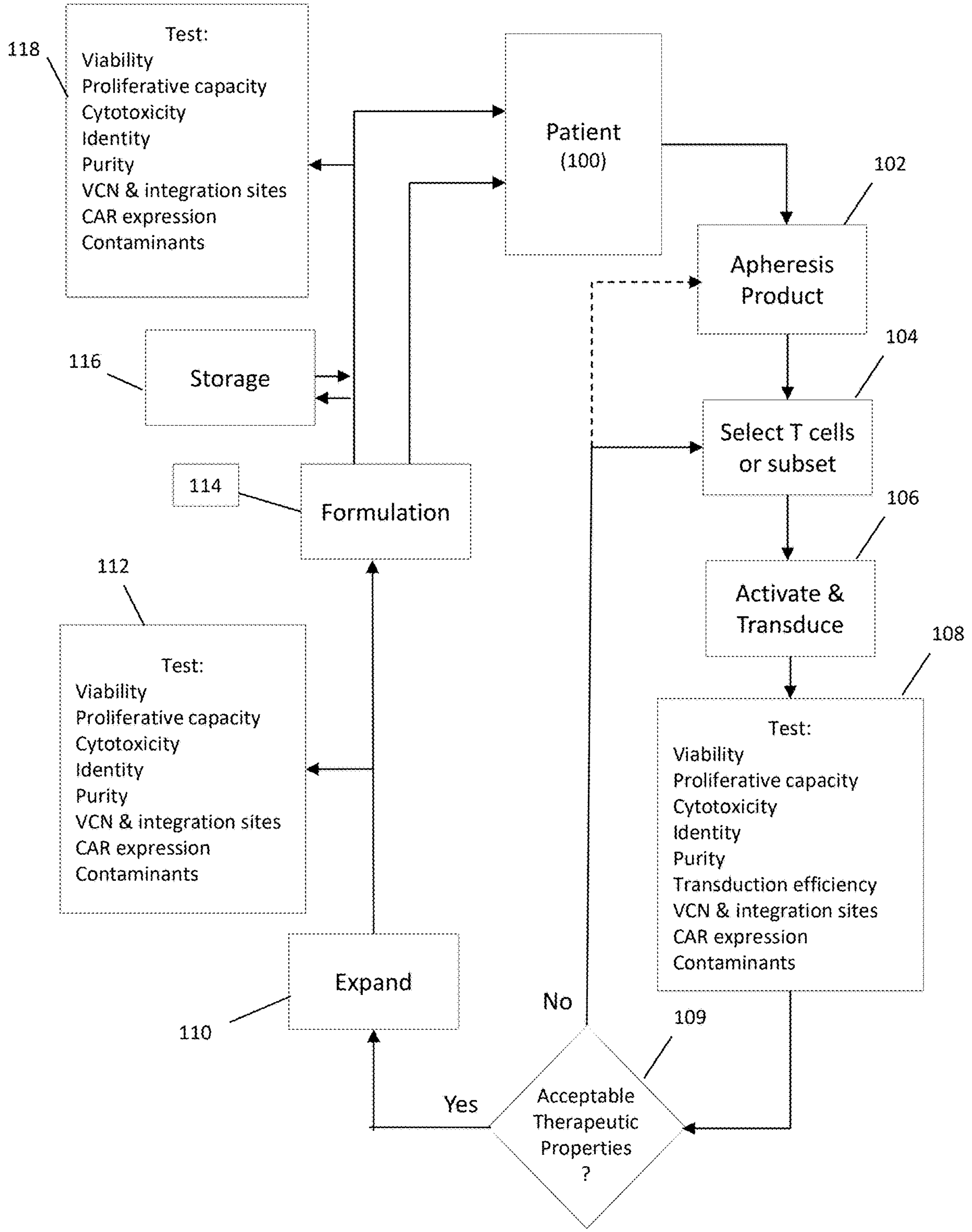
Figure 1B:
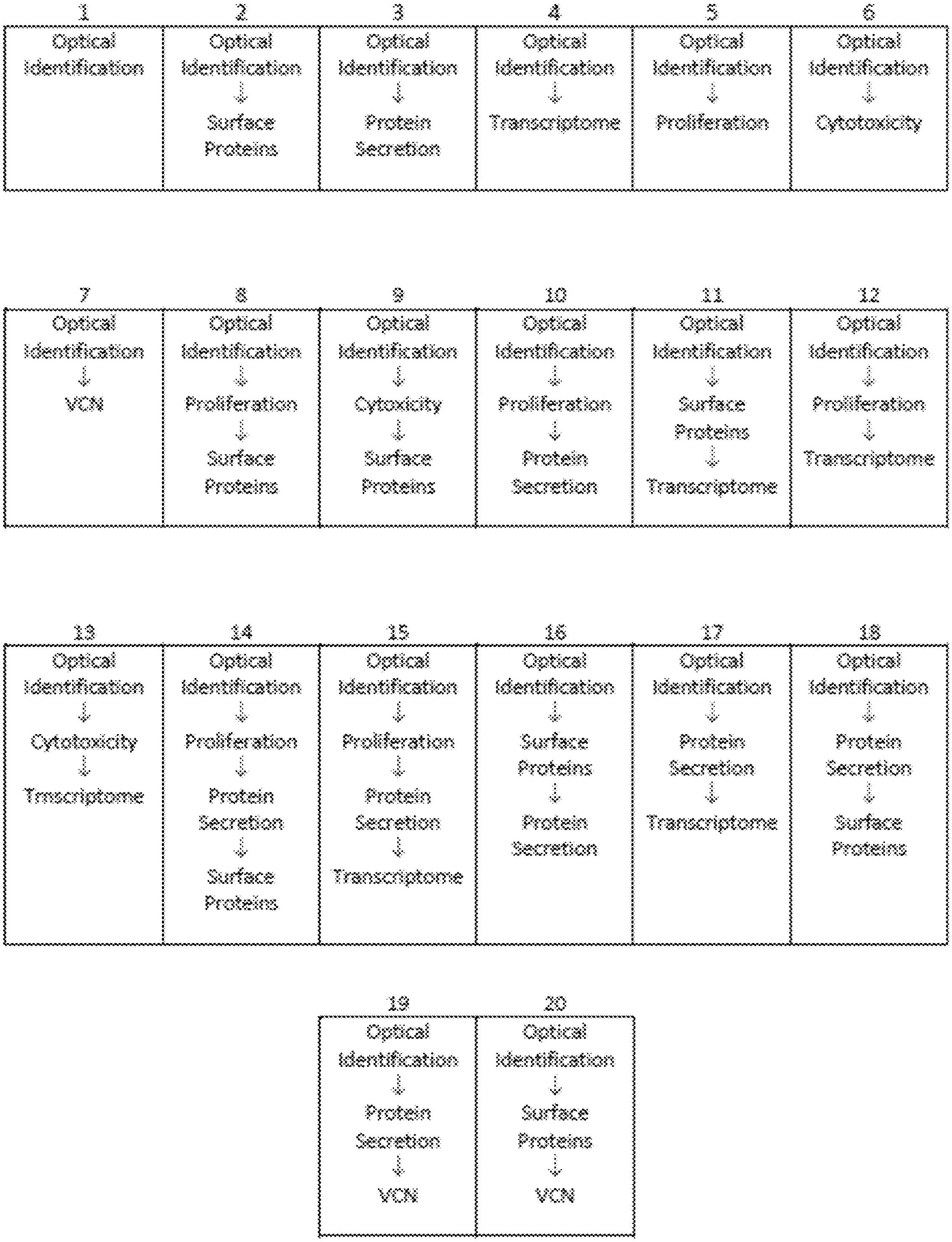

As mentioned above, CAR-T cell therapy, e.g. to treat cancers, is an exemplary application of the present invention. The major steps of autologous CAR-T cell production for therapy are illustrated in FIG. 1A, and are described in many publications, for example, Wang et al, Molecular Therapeutics—Oncolytics, 3: 16015 (2016); Barrett et al, Annu. Rev. Med., 65: 333-347 (2014). The figure illustrates where in the production process quality assurance testing may take place. White blood cells containing lymphocytes are separated from other blood components of patient (100) by apheresis (102), e.g. Allen et al, Transfusion, 57(5): 1133-1141 (2017). Further enrichment (104) of particular subsets of lymphocytes may be carried out by depleting undesired subsets or enriching desired subsets using magnetic beads, or other techniques, e.g. to remove T regulatory cells which may suppress desired activity of the CAR-T cells. After a suitable subset is selected, T cells are activated and transduced (106); that is, they are made competent to perform immune functions and to express CARs. Activation may be accomplished by a variety of treatments, e.g. exposure to anti-CD3/anti-CD28 beads. Transduction may also be accomplished by a variety of techniques, e.g. lentivirus transduction and integration into T cell genomes, e.g. Wang et al (cited above); Barrett et al (cited above). After such transformations, T cells are tested (108), for example, using the present invention, to determine whether desired properties for CAR-T cell therapy are present, such as, an adequate degree of cytotoxicity towards desired target cells, viability, proliferative capacity, identity, absence of contaminants, non-excessive virus copy number values, and so on. If the activated and transduced cells do not have acceptable therapeutic properties (109), then new cells must be prepared. If they have acceptable therapeutic properties, then the cells are expanded (110); that is, they are cultured to increase their numbers. As conditions for expansion may alter the cells, they are tested again for desirable properties after expansion (112). Successfully expanded cells may be formulated (114) for infusing into a patient (100) and/or storage (116) for subsequent infusions. If subsequence infusions are required, cells removed from storage are again tested to assure that they possess the desired therapeutic properties. Exemplary single cell assays that may be carried out with methods and systems of the invention are listed in Table 1 and FIG. 1B. In some embodiments, successive assays each acquiring additional information may be conducted on the same cell, or cells, in chambers of a channel.

CAR-T cell or therapeutic stem cell development and manufacture are an exemplary applications of the present invention. In some embodiments, methods of the invention for determining one or more cellular characteristics, such as those relevant to CAR-T cell or therapeutic stem cell development or production, may be performed by the following steps: (a) providing a fluidic device comprising (i) one or more channels each comprising a first surface and, optionally, assay components for detecting or measuring a cellular characteristic, (ii) a spatial energy modulating element in optical communication with each first surface, and (iii) a detector that identifies positions of cells in each channel based on one or more optical signals therefrom; (b) disposing cells on the first surface of the channel; (c) loading each channel with one or more polymer precursors; (d) synthesizing one or more chambers in the channels, each chamber enclosing a cell, by projecting light into each channel with the spatial energy modulating element such that the projected light causes cross-linking of the one or more polymer precursors to form polymer matrix walls of the chambers, wherein the positions of the synthesized chambers are determined in each channel by the positions of the cells enclosed or encased thereby identified by the detector; and (e) incubating the cells under assay conditions in each channel to generate signals from chambers of each channel indicative of cellular characteristics. In some embodiments, incubating the cells under assay conditions comprises performing one or more assays on the cells in the channels to determine one or more of the cellular characteristics selected from the group consisting of cytotoxicity, viability, proliferation rate, phenotype, vector copy number, vector integration sites, transcriptome, and genomic copy number variation. In some embodiments, polymer matrix walls of chambers comprise degradable hydrogels. In some embodiments, incubating comprises lysing the cells and capturing on the first surface one or more cellular components by capture agents. In some embodiments, incubating further comprises degrading the degradable polymer matrix walls after such one or more cellular components are captured. As used herein, the terms "capture element" and "capture agent" are used interchangeably. In some embodiments, capture agents (or capture elements) are covalently attached to a surface of a channel. In some embodiments, capture agents (or elements) comprise oligonucleotides having sequences capable of hybridizing to a cellular component, either directly, e.g. poly A tail of mRNA, or indirectly, e.g. an adaptor strand of an adaptored genomic DNA fragment produced by tagmentation. In some embodiments, capture agents (or elements) comprise one or more antibodies. In some embodiments, capture agents (or elements) comprise spatial barcodes. In some embodiments, capture agents (or elements) comprising oligonucleotides further comprise primers for solid phase amplification, such as, bridge PCR. In some embodiments, a fluidics device comprises a plurality of channels. In some embodiments, a plurality of cells is disposed on a surface of each channel. In some embodiments, such plurality of cells comprises 100 or more cells, or 1000 or more cells, or 10,000 or more cells, or a number of cells within the range of from 100 to $10^6$ cells.

In some embodiments, the steps of disposing cells and loading polymer precursors are performed by mixing the cells and polymer precursors outside of the fluidic device then loading the channel with the mixture of cells and polymer precursors. In some embodiments, cells are delivered to a first surface in a fluid where they are randomly dispersed over the first surface. In some embodiments, after cells are delivered to a surface of a channel they are randomly disposed on the surface. In some embodiments, the step of incubating under assay conditions may comprise only a single step of an assay comprising more than one step, such as, for example, a step of detecting a signal (or in the case of a material signal, generating a sequencing-ready nucleic acid), or such step of incubating under assay conditions may comprise a plurality of steps of a multi-step assay. In some embodiments, cells may be treated or subjected to assay steps prior to loading into a channel of a fluidic device, so that the step of incubating may comprise only a single step of a multi-step assay, such as signal generation and/or signal collection. In other embodiments, the step of incubating may comprise the implementation of an assay step or part of an assay, such as, cDNA synthesis, second strand synthesis, capture of an assay component or a cellular component, or the like. In some embodiments, assay conditions may comprise a series of steps each with different conditions (e.g. temperature, pH, presence or absence of particular reagents, such as, primers or an enzyme, e.g., a ligase, a polymerase, a transposase, or the like). For example, such steps may comprise loading primers so that they diffuse across chamber walls and anneal to target sites on a template strand in a sample in the chamber, extending the annealed primers, heating the channel so that the extended primers melt from its template strand, capturing the melted extended primers by capture agents attached to the first surface, and so on.

In some embodiments, cells are adherent with respect to a first surface so that upon settling and contact the cells remain on the surface, even in the presence of fluid movement. In other embodiments, cells are non-adherent with respect to a first surface so that although they may settle on the first surface they may move or return to a suspension in the presence of fluid movement. One of ordinary skill in the art would recognize that a first surface may be treated (for example, by the attachment of appropriate capture elements) to retain non-adherent cells, either over the entire first surface (or polymer matrix walls or second surface) or selected portions thereof. In some embodiments, assay components that may be provided with or as part of a channel include, but are not limited to, capture elements, such as, capture oligonucleotides, primers for surface amplification, antibodies, functional groups that may react with hydrogel components, beads, and the like. In some embodiments, such assay components may be attached to any one of a first surface, a second surface or a polymer matrix wall exclusively, or on combinations of such surfaces, either exclusively, or in combination with other reagents. In some embodiments, assay components that may be provided after synthesizing gel chambers include, but are not limited to, lysing reagents, transcription reagents, reverse transcription reagents, antibodies, polymerases, primers, beads, and the like. As used herein, "channel" means a container capable of holding fluid (which may be static or flowing) and having at least one surface on which cellular assays may be conducted. In some embodiments, a channel may have a first surface and/or a second surface on which chambers may be synthesized and/or on which cellular or assay components may be attached. In addition, in some embodiments, cellular or assay components may be attached or capture by capture elements on a polymer matrix wall. As used herein, reference to a "first surface" (for example, as a surface comprising capture elements) may comprise a second surface, or as appropriate, a polymer matrix wall. As used herein, reference to a "surface" without reference to "first" or "second" is intended to comprise a first surface or a second surface. In some embodiments, a channel may constrain a flow of fluid therethrough from an inlet to an outlet. In other embodiments, a channel may comprise a non-flowing volume of fluid that may be removed, replaced or added to by way of an opening or inlet; that is, in some embodiments, a channel of the invention may be a well or a well-like structure, such as a trough. In some embodiments, hydrogel chambers are synthesized in methods of the invention; and in other embodiments degradable hydrogel chambers are synthesized in method of the invention. In some embodiments, particularly for CAR-T cells, a plurality of cellular characteristics may be selected from the following characteristics: cytotoxicity, proliferative capacity or proliferation rate, activation status, cellular identity, purity, gene expression profile or transcriptome, epigenetic profile, sequence copy number (e.g., integrated viral copy number for transduced cells, plasmid copy number for transiently transfected cells, gene copy number, or the like). Additional assays may include culture contamination assays including, but not limited to, viral, bacterial, yeast, mold, or mycoplasma assays, endotoxin assays, and cellular morphology assays.

Another exemplary application of the invention includes screening CRISPR/Cas9-based modified cell populations. For example, Shifrut et al (Cell, 175(7): 1958-1971 (2018)) screened populations of T cells transduced by lentivirus producing single guide RNAs of a library targeting known T cells genes. The objective was to identify genes which when knocked out enhanced the T cell response, which was measured by growth rate. The present invention is perfectly suited to provide single cell proliferation rates on a large scale such as required by such studies.

An exemplary system for carrying out the above method is illustrated in FIG. 5A. Flow cell (500) is a component of a fluidic device that provides channels for carrying out a variety of assays and liquid handling components under programmable control for delivering samples and reagents to the channels. In this illustration, four channels (502, 504, 506, and 508) are shown, with blow-up view (512) of segment (510) of channel 2 (504) shown below. In the abstracted view of flow cell (500) of FIG. 5A, inlets, outlets and other features of the channels are not shown. On first surface (514) of channel 2 (504) a plurality of cells, e.g. (518), are each enclosed by a hydrogel chamber, e.g. (516). In some embodiments, the porosity of polymer matrix walls of the hydrogel chambers is selected to be impermeable to the cells, but permeable to assay reagents. Thus, reagents may be introduced to, and removed from, the interiors of the hydrogel chambers by flowing (520) them through the channels, but cell are retained in. Below blow-up (512) of channel segment (510) is shown exemplary optical system (521) for photosynthesizing hydrogel chambers at the locations of cells in the channels and for collecting optical signals including images, in some embodiments. One of ordinary skill in the art would recognize that optical systems with different configurations than those of FIGS. 5A and 5B may be employed for carrying out these functions. In some embodiments, a plurality of DMD-objective subsystems for synthesizing hydrogel structures may be employed to increase the speed of synthesis by synthesizing multiple structures simultaneously.

Returning to FIG. 5A, for photosynthesizing the hydrogel chambers, light source (522) generates light beam (523) of appropriate wavelength light (e.g. UV light) that passes through an appropriate photo-mask or beam-shaping or beam steering (Galvo) system for shaping a beam to synthesize a desired structure or structures in a channel. In some embodiments, a digital micromirror device (DMD) (524) is employed, in other embodiments, a physical photo-mask may be employed. Chamber position, shape and polymer matrix wall thickness is determined at least in part from cell position information determined from images collected by detector (532). Reflected light from DMD (524) is shaped using conventional optics, e.g. collimating optics (528), and is directed through objective lens system (534) into channel 2 segment (510). Objective (534) and flow cell (500) move relative to one another in the xy-directions (536) to photosynthesize chambers at any position in any of the channels. In some embodiments, flow cell (500) moves and optical system (521) is stationary. In some embodiment, objective (534) may also direct light beam (527) from light source (529) to targets, such as cells, on first surface (514) and collect optical signals, such as fluorescent signals, from assays taking place on first surface (514). Alternatively, optical signal collection may be carried out with a separate objective as shown if FIG. 5B. Information collected by detector (532), or its counterpart in the embodiment of FIG. 5B, particularly cellular positions in their respective channels, is employed by computer (538) and/or subsidiary controllers to direct DMD (524) and translation devices controlling the relative positions of objective (534) and flow cell (500) to synthesize hydrogel chambers of the appropriate shape and size at the appropriate locations.

FIG. 5B illustrate an alternative optical system in which the detection portion (550) of the optical system moves (572) independently from the movement (568) of the synthesis portion (552) of the optical system. Detection portion (550) of the optical system comprises detector (556), objective (558), light source (560) and interconnecting optical elements, such as dichroic mirror (562). As with the embodiment of FIG. 5A, detector (556) is operationally associated with computer (564) and the synthesis portion (552) of the optic system to provide synthesis portion (552) with cellular position information. Computer (564) and (538) are also in operationally associated with stages and/or motors controlling the relative positions of the objectives of the optical systems and the position of the flow cell. In this embodiment, synthesis portion (552) of the optical system is located on the other side of first surface (564) from detection portion (550). As with the embodiment of FIG. 5A, it comprises the conventional components objective (574), mirror (576), collimating optics (580), DMD (582) and light source (578).

In some embodiments, cells, e.g. (518) in FIG. 5A, are disposed randomly on first surface (514). In alternative embodiments, first surface (514) may comprise regularly spaced sites or features for capturing cells so that they are disposed substantially only on such sites or features on the first surface. For example, in some embodiments, such sites or features may be a rectilinear or a hexagonal array of spots. In some embodiments, such sites or features may comprise capture elements, such as antibodies specific for cell surface proteins, for capturing or immobilizing cells at the sites or features. In some embodiments, first surface (514) may comprise capture elements designed to immobilize particular cell types. For example, lymphocytes are non-adherent on most surfaces; however, such cells may be allowed to settle on first surface by gravity or may be immobilized on surfaces using capture elements comprising antibodies specific to lymphocyte cell surface proteins, e.g. CD3, CD4, CD8 or the like, e.g. Sekine et al, J. Immunol. Meth., 313(1-2): 96-109 (2006); Zhu et al, Anal. Chim. Acta, 608: 186-196 (2008). For adherent cells, in some embodiments, patterning of fibronectin protein or polylysine on surfaces may be employed to capture such cells at defined locations. In some embodiments, such methods may be used to separate different cellular subsets in different regions within the same channel.

Cell Proliferation Assays

FIGS. 2A-2F illustrate exemplary assays for determining proliferation rates of cells followed by their identification based either on cell surface proteins, protein secretion profile, or the like. Cells may also be identified or characterized by their transcriptomes determined as described below or by like techniques. It is understood that the term "proliferation rate" may include a measure of a lack of proliferation. For example, chambers enclosing one or more cells may be exposed to an agent, e.g. a drug candidate, after which such cells may be returned to normal growth conditions. In some cases, the agent may kill or retard the growth of the cells, e.g. in comparison to controls not exposed to the agent. Thus, in the case of the treated cells, a negative "proliferation reate" may be possible because the final numbers of cells counted in the chambers may be less than the original numbers; or a signal monotonically related to cell number may decline in value.

Figure 2A:
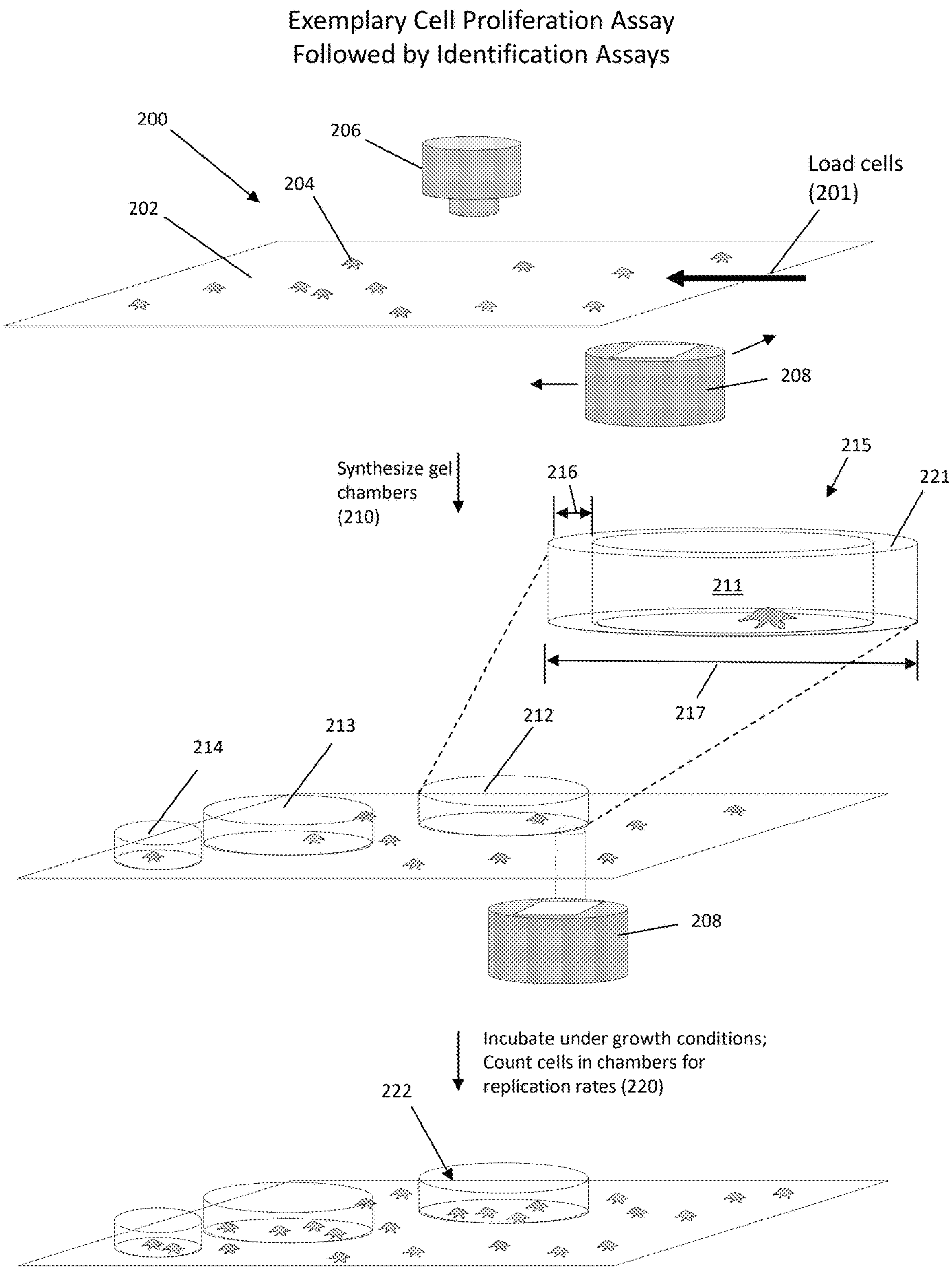
FIGS. 2A-2F illustrate steps of exemplary assays for determining proliferative capacity of cells in a population followed by their identification by cell surface protein expression and protein secretion.

FIG. 2A shows steps of a proliferation assay carried out by a system of the invention. Cells and polymer precursors are loaded into channel (200) and disposed on first surface (202), e.g. cell (204). Positions of cells are determined by detector (206) which are used by a control system to generate instructions for spatial energy modulating element (208) to produce light beams to synthesize (210) hydrogel chambers in channel (200) around single cells, as illustrated by hydrogel chambers (212, 213 and 214). Blow-up (215) illustrates that the solid appearing structures (212, 213 and 214) have interiors (211) and walls (221) with predetermine thickness (216). Likewise, hydrogel chambers have a predetermined shape (e.g. circular with diameter (217)) and enclose predetermined areas. In the figures, for convenience, chambers are illustrated as standing in isolation without connection with adjacent chambers and as having a cylindrical or annular-like shapes; however, a spatial energy modulating element may synthesize chambers of different shapes and sizes, as is useful for particular applications. In some embodiments of the proliferation assay, each hydrogel chamber synthesized has the same shape and area, for example, annular-like with an interior area selected from the range of 0.001 to 0.01 $mm^2$, or in the range of 001 to 1.0 $mm^2$. In some embodiments, each hydrogel chamber synthesized has the same shape and area for each different type of cell being assayed, for example, cytotoxic T lymphocytes may be confined in chambers having one area whereas helper T lymphocytes may be confined in chambers having another area. After a desired number of hydrogel chambers are synthesized, cells are incubated for a period under growth conditions, after which (for example) cells in each chamber are counted (220) to give a measure of proliferative capacity for each cell. In some embodiments, after synthesizing chambers to enclose selected cells, non-selected cells may be removed by a washing step or by other changes of reagents in the channel. In some embodiments, cells may be stained with a membrane or intracellular dye for determining proliferation by dye dilution so that an independent measure of cell proliferation may be obtained. Exemplary intracellular dyes for dye dilution include, but are not limited to, Hoechst 33342, carboxyfluorescein succinimidyl ester (CFSE), and the like. The desired number of single cells enclosed by chambers depends on statistical confidence desired in the measured values. If a subpopulation of interest is present as only a small fraction of a total population then a larger number chambers is required. In some embodiments in which mammalian cells are assayed the number of hydrogel chambers synthesized around single cells may be greater than 100; or greater than 1000; or greater than 10,000; or the number may be in the range of from 100 to 100,000; or in the range of from 1000 to 100,000. After counts are recorded for each chamber, further assays may be conducted on the clonal populations within the chambers to identify the cell types, for example, by an assessment of cell surface proteins, cell protein secretions, transcriptome, or the like. This approach is particularly useful for assessing populations of immune cells, especially engineered immune cells. In some embodiments, a cell proliferation assay may be carried out by the following steps: (a) providing a fluidic device comprising (i) a channel comprising a first surface, cells disposed on or adjacent to the first surface, and one or more polymer precursors, (ii) a spatial energy modulating element in optical communication with the first surface, and (iii) a detector that identifies positions of cells in the channel based on one or more optical signals therefrom; (b) synthesizing one or more chambers in the channel enclosing each of one or more cells by projecting light into the channel with the spatial energy modulating element such that the projected light causes cross-linking of the one or more polymer precursors to form polymer matrix walls of the chambers, wherein the positions of the synthesized chambers are determined by the positions of cells enclosed thereby identified by the detector; (c) incubating the cells under proliferation conditions; and (d) determining a proliferation rate of the cells. In some embodiments, determining a proliferation rate comprises counting the cells in each chamber.

Figure 2B:
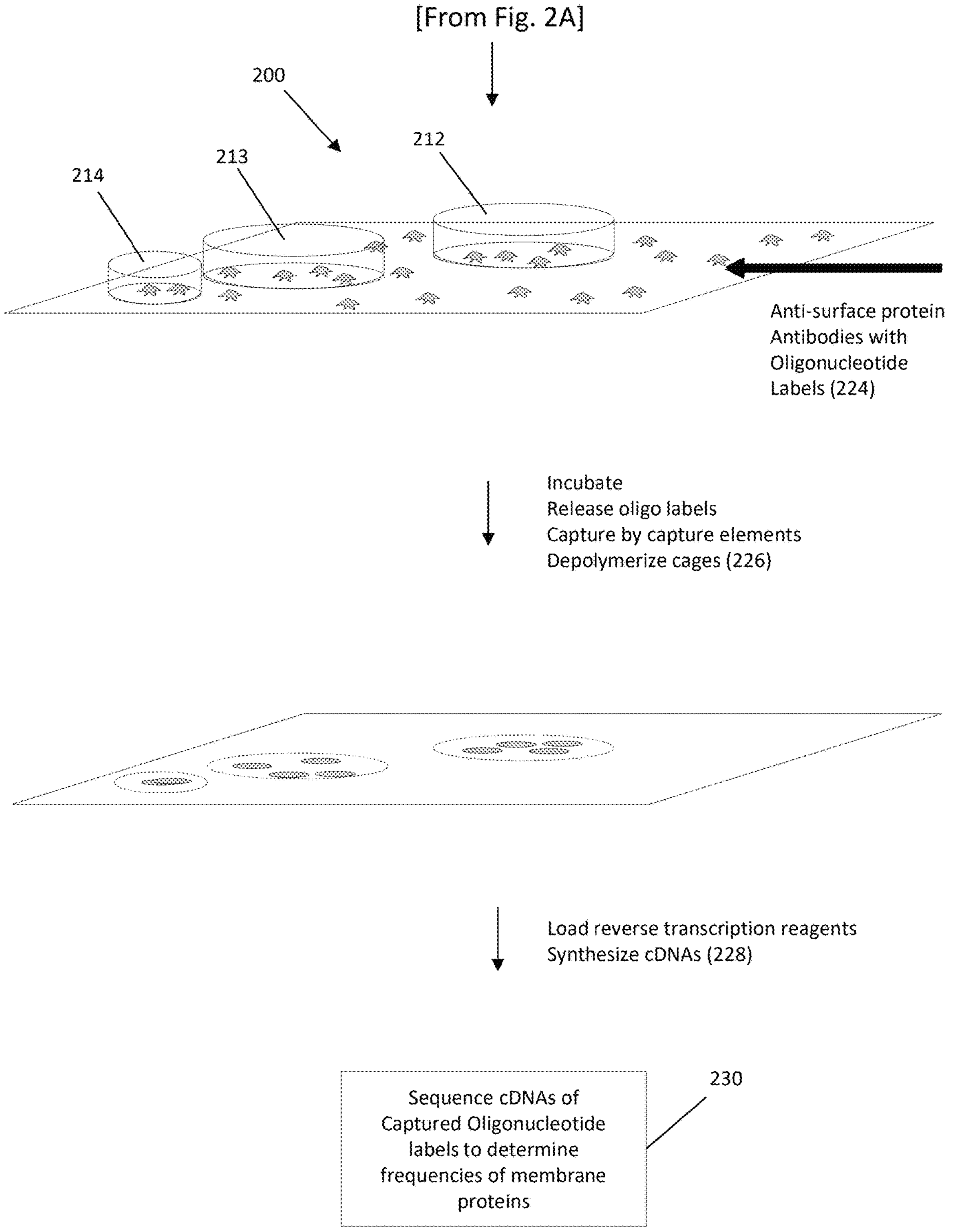

FIG. 2B illustrates a follow-on assay to identify cells by cell surface markers. It is noted that if cell surface markers are to be measured directly (without first measuring cell proliferation), then prior to introduction to a channel, cells may be incubated with labeled antibodies, wherein the labels may vary widely including, but not limited to, fluorescent labels, oligonucleotide labels, colorimetric labels, enzymatic labels, or the like. Also, it is understood that binding compounds other than antibodies or fragments thereof may be employed in the invention, such as, for example, aptamers. After determining proliferation rates for each chamber, channel (200) is loaded with a mixture of different labeled antibodies each specific for a different cell surface protein. Such antibodies may be prepared for any cell surface protein, but surface proteins of special interest are those that characterize immune cells and their binding specificities (e.g. CARs). In some embodiments, antibodies are specific for surface proteins that include, but are not limited to, cluster of differentiation (CD) markers, such as, CD3, CD4, CD5, CD6, CD7, CD8, CD11, CD19, CD20, CD21, CD22, CD23, CD24, CD25, or the like. In some embodiments, the labels of the antibodies are oligonucleotides. In some embodiments, such oligonucleotides may be attached to the antibodies by a scissile bond which, for example, may be cleavable by conventional methods, such as, chemical cleavage by reducing conditions, acid conditions, or base conditions, or photo cleavage by exposure to an appropriate wavelength and intensity of light. In some embodiments, exposing antibody-labeled cells to a lysing reagent is sufficient to release the antibody-oligonucleotide conjugates for capture by capture elements, whether or not a scissile linkage is present. The oligonucleotide labels may comprise a barcode sequence that uniquely identifies the protein for which the antibody is specific. The oligonucleotide labels may also include a sequence complementary to oligonucleotides attached to the first surface as capture elements. In some embodiments, either such complementary sequences, or those of the capture oligonucleotides, may be blocked by hybridization of a mismatch or shorter oligonucleotide (e.g. less stable than the oligonucleotide label-capture oligonucleotide duplex) to prevent spurious capture of the antibody-oligonucleotide conjugates by capture oligonucleotides on the first surface when loaded into a channel. Such blocking oligonucleotides are then removed in a wash step prior to releasing the oligonucleotide labels of the cell surface bound antibodies. Alternatively, oligonucleotide labels may be configured to be ligated to capture oligonucleotides by way of a splice oligonucleotide. The splice oligonucleotide would block spurious hybridization of the oligonucleotide labels prior to release from the antibody-surface protein complexes. After such release and introduction of a ligase, oligonucleotide labels would be captured by the free end of the splice oligonucleotide and the oligonucleotide label would be ligated to the end of the capture oligonucleotide.

In the embodiment of FIGS. 2A-2B, after a period of incubation (226) to permit binding of antibodies to their target proteins, the oligonucleotide labels are released and captured by the complementary sequences of the capture elements. For example, oligonucleotide labels may be attached by a disulfide linker which may be released by a reducing agent, e.g. Hermanson (cited above). In some embodiments, after incubating, unbound antibodies may be removed, for example, by a washing step. In some embodiments, channel (200) may be loaded (228) with a reaction mixture comprising a polymerase, dNTPs and other components, necessary for extending the complementary oligonucleotides of the capture elements with the captured antibody oligonucleotides as templates. In some embodiments, the polymer matrix walls of the chambers may be degraded, or depolymerized (226), after which channel (200) may be loaded (228) with such extension reagents. As explained more fully below, the DNA copies may be sequenced (230) in situ or they may be released from the first surface (perhaps after amplification), eluted, and sequenced externally. In the latter process, the complementary oligonucleotides of the capture elements include spatial barcodes for identifying the chamber from which antibody barcode sequences originate. In either case, the numbers of each kind of antibody oligonucleotides calculated from the sequence data provide profiles (e.g. relative frequencies of each cell surface protein) of the cell surface proteins of the cells enclosed by each of the hydrogel chambers. Moreover, this data can be correlated to the proliferative capacity of such cells.

Figure 2C:
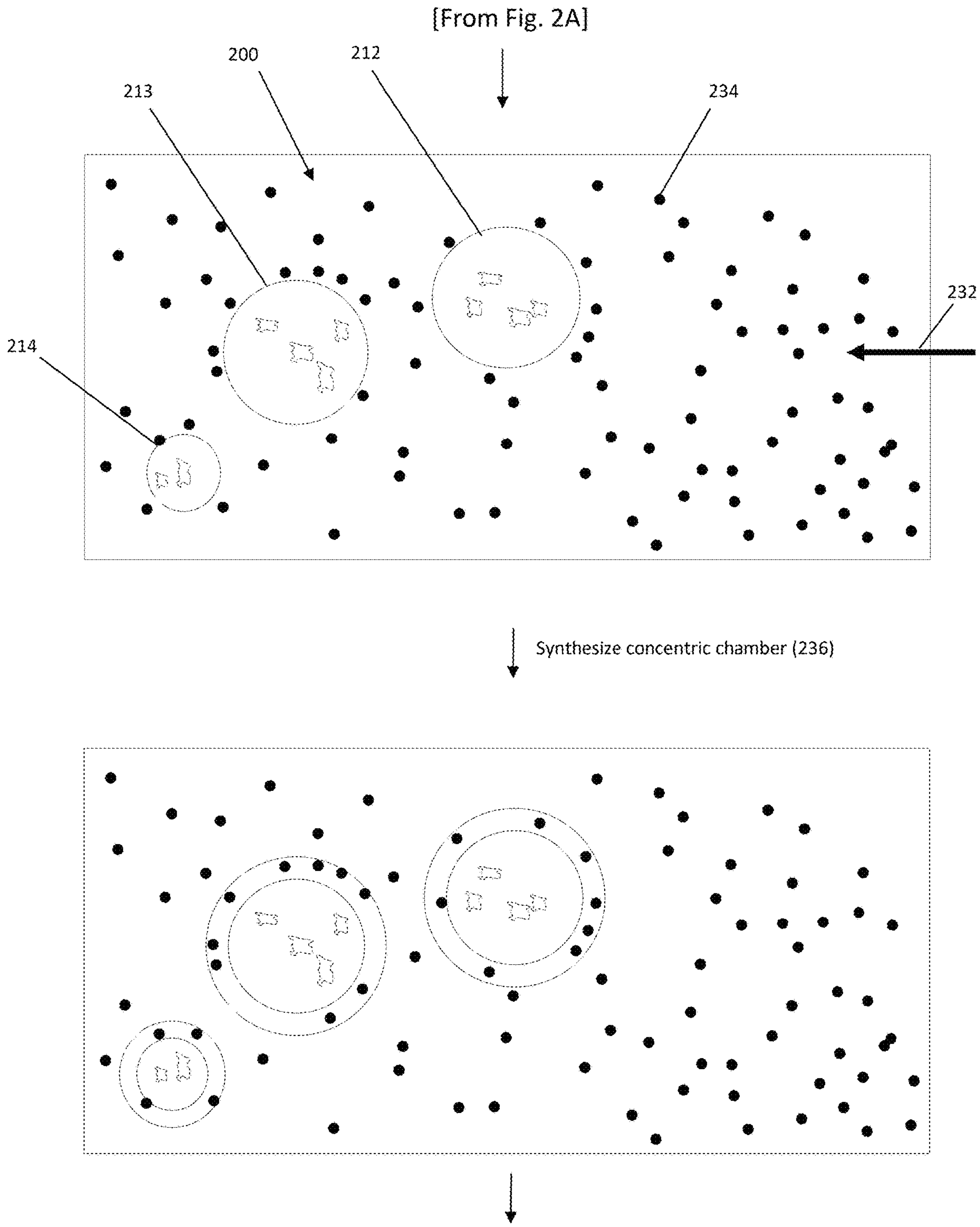
Figure 2D:
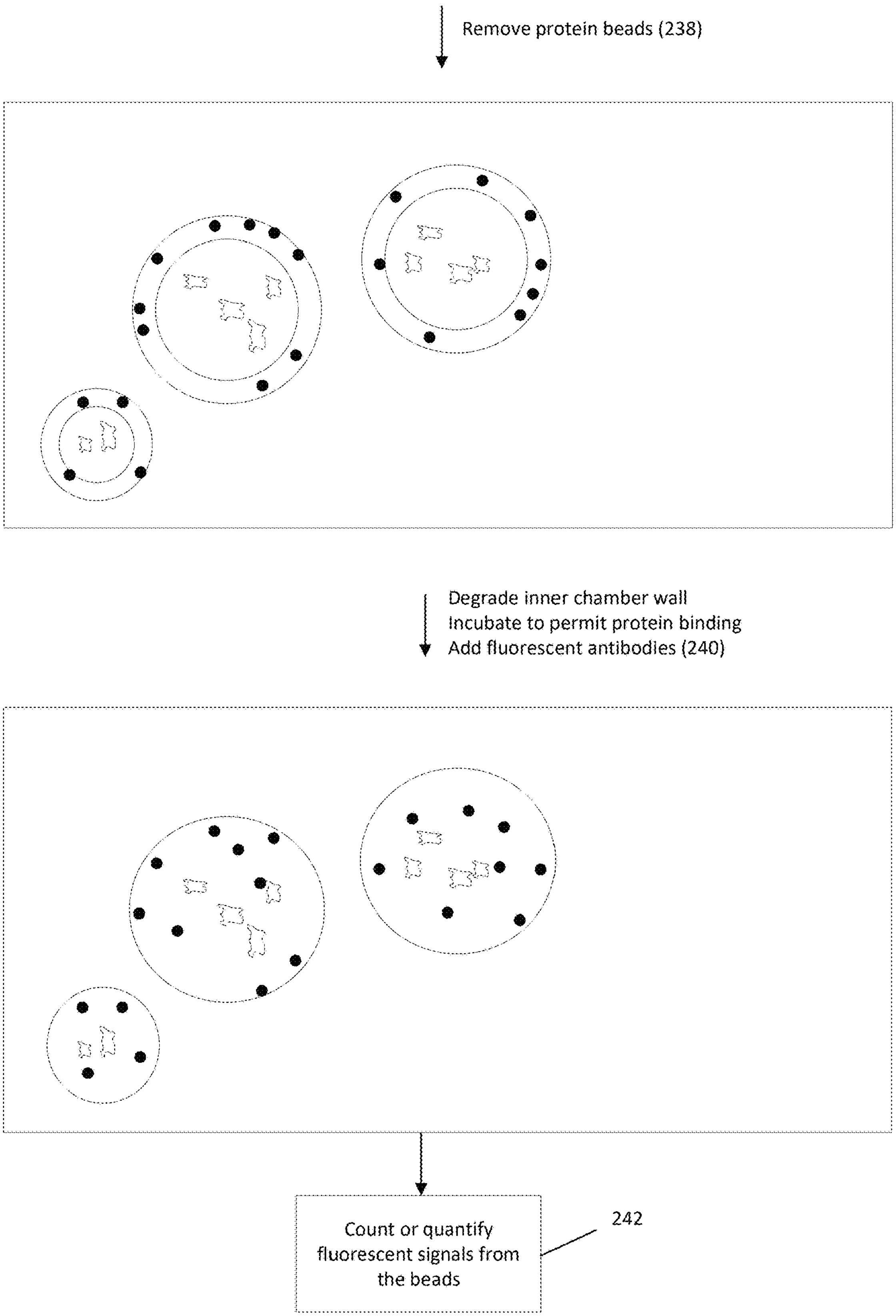

FIGS. 2C-2D illustrate one embodiment of a protein secretion assay employing commercially available protein-capture beads, e.g. Biolegend (San Diego, CA). One of ordinary skill in the art would recognize that other surfaces beside (or in addition to) bead surfaces may be employed for localized capture of secreted proteins, such as cytokines. The upper and lower panels of FIG. 2C are top views of a section of channel (200) containing chambers (212, 213 and 214). (Thus, FIGS. 2C-2D illustrate an alternative assay of cells after counting (to that of FIG. 2B), or in some embodiments, the assay of 2B could be performed after the assay of FIGS. 2C-2D, so that protein secretion profiles would be determined and afterward surface protein profiles would be determined) After cell counting, channel (200) is loaded (232) with protein-capture beads (e.g. 234) which are beads (usually impermeable to the polymer matrix walls of the chambers) which have covalently attached antibodies specific for predetermined proteins that may be secreted by the cells enclosed by the chambers. Such beads may be prepared for any secreted protein, but proteins of special interest are cytokines and immune active proteins including, but not limited to, interferons, such as interferon-γ (IFN-γ) and interferon-α (IFN-α), interleukins, such as, interleukin-1 (IL-1), interleukin-2 (IL-2), interleukin-4 (IL-4), interleukin-5 (IL-5), interleukin-6 (IL-6), interleukin-7 (IL-7), interleukin-10 (IL-10), interleukin-13 (IL-13), interleukin-15 (IL-15), and interleukin-21 (IL-21), interleukin-23 (IL-23), colony stimulating factors (CSFs), such as, granulocyte-macrophage colony stimulating factor (GM-CSF), granulocyte colony stimulating factor (G-CSF), tumor necrosis factors (TNFs), such as, TNF-α and TNF-β, and effector molecules, such as, granzyme B. After such beads are loaded, a concentric chamber is synthesized (236) around each of the chambers containing cells, after which beads outside of the concentric chambers are removed (238). In some embodiments, the size of the larger concentric chamber is sufficient to enclose a number of protein-capture beads so that there is a high probability (e.g. greater than 90 percent, or greater than 95 percent, or greater than 99 percent) that at least one bead is present for each different cytokine to be measured. One of ordinary skill would recognize that such size determination depends on the concentration of beads loaded into channel (200). After synthesis of concentric chambers, the polymer matrix walls of the inner chambers are depolymerized (240) so that cells and bead may freely mix so that secreted proteins may be capture by the beads, after which label antibodies ("detection antibodies") are loaded into the channel to bind to another epitope of the captured proteins (as in a sandwich assay). In some embodiments, porosity of the inner chambers is selected to prevent or inhibit passage of secreted proteins through its polymer matrix walls. In some embodiments, porosities of both the inner chambers and the outer concentric chambers are selected to prevent or inhibit the passage of secreted proteins, and before loading detection antibodies, the polymer matrix walls of the outer chambers are depolymerized to remove the barriers to the detection antibodies binding to captured proteins. Alternatively, in some embodiments, the porosity of the polymer matrix walls of the inner chamber may be selected to allow passage of secreted proteins into the annular area containing the beads. Relative amounts of secreted proteins may be estimated by counting each bead type generating a characteristic fluorescent signal or by integrating each different fluorescent signal across all bead adjacent to the cells of the chamber. This embodiment may be implement by the following steps after cells are disposed on a first surface, either initially or after another assay not destructive of the cells: (a) loading the channel with a second reaction mixture comprising second polymer precursors and protein capture beads comprising protein-capture antibodies that bind proteins secreted by said cells; (b) synthesizing second chambers enclosing each of the one or more chambers by projecting light into the channel with the spatial energy modulating element such that the projected light causes cross-linking of the one or more polymer precursors to form polymer matrix walls of second chambers, wherein the positions of the synthesized second chambers are determined by the positions of the chambers enclosed thereby identified by the detector; and (c) depolymerizing the chambers so that the protein capture beads in each second chambers mix with the cells enclosed by the depolymerized chamber therein. In some embodiments, the (first) polymer precursors may include precursors that form gel linkages degradable by reducing conditions, e.g. structure 2 of Table 2B, whereas the second polymer precursors do not include such precursors. In some embodiments, the above method further includes incubating the cells with the protein capture beads; and detecting protein secreted by the cells by an amount of labeled protein detection antibodies for each protein bound to protein-capture beads adjacent to the cells.

One of ordinary skill recognizes that the function of protein-capture antibodies may be carried out by other affinity reagents that have specific binding capacity, such as aptamers. As used herein, the term "affinity reagent" means a compound capable of specifically binding to a target molecule, such as a protein. Affinity reagents include, but are not limited to, antibodies, antibody fragments, aptamers and like compounds.

Figure 2E:
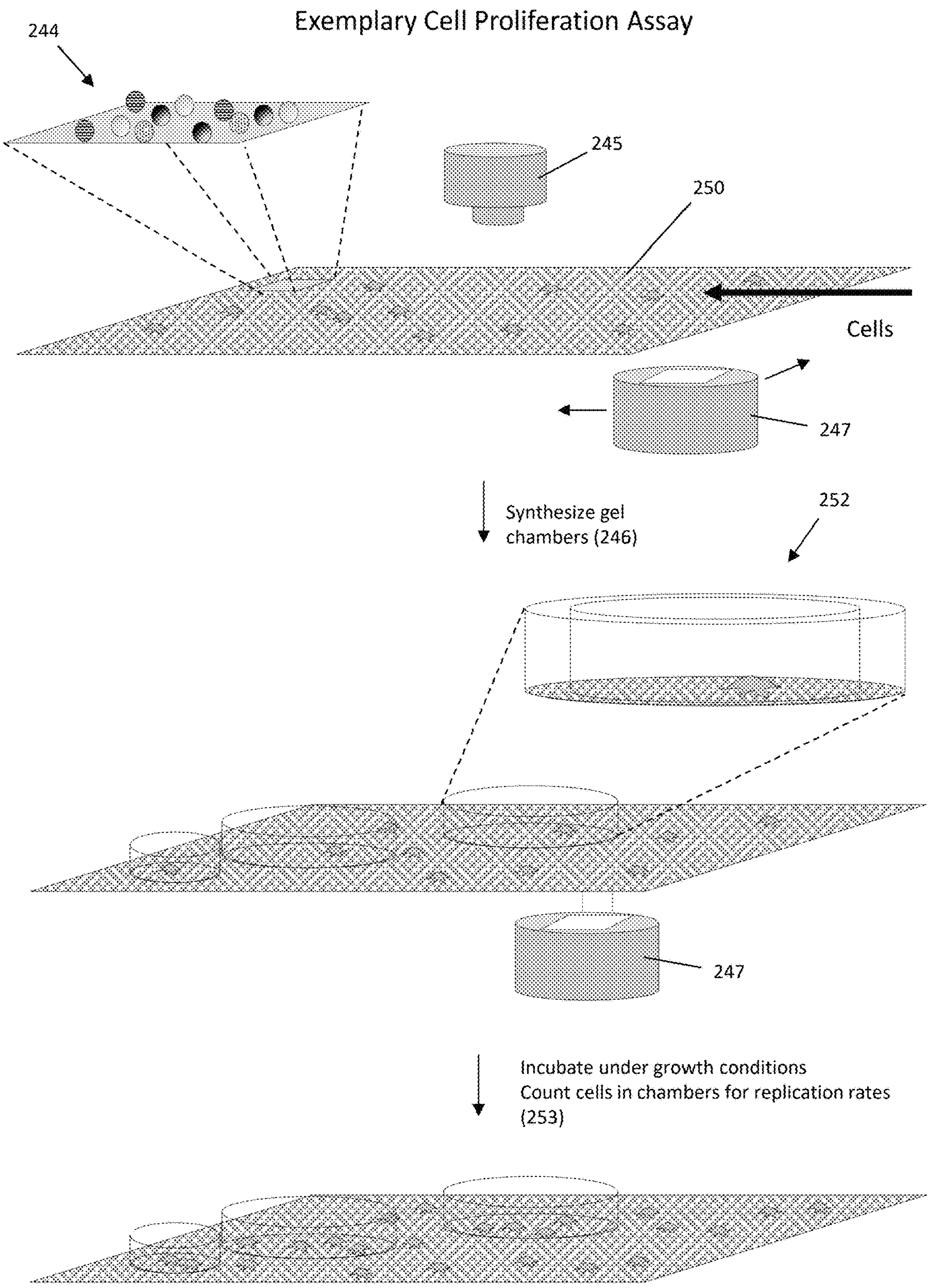
Figure 2F:
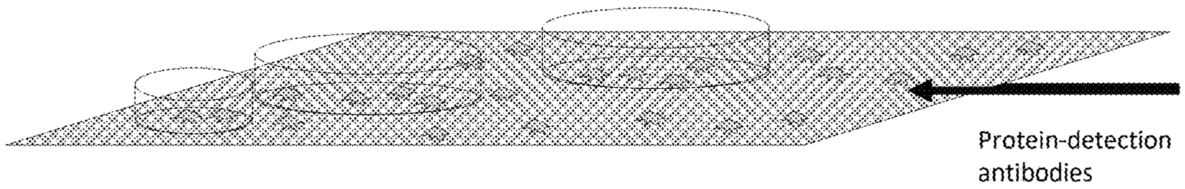
Figure 2F:
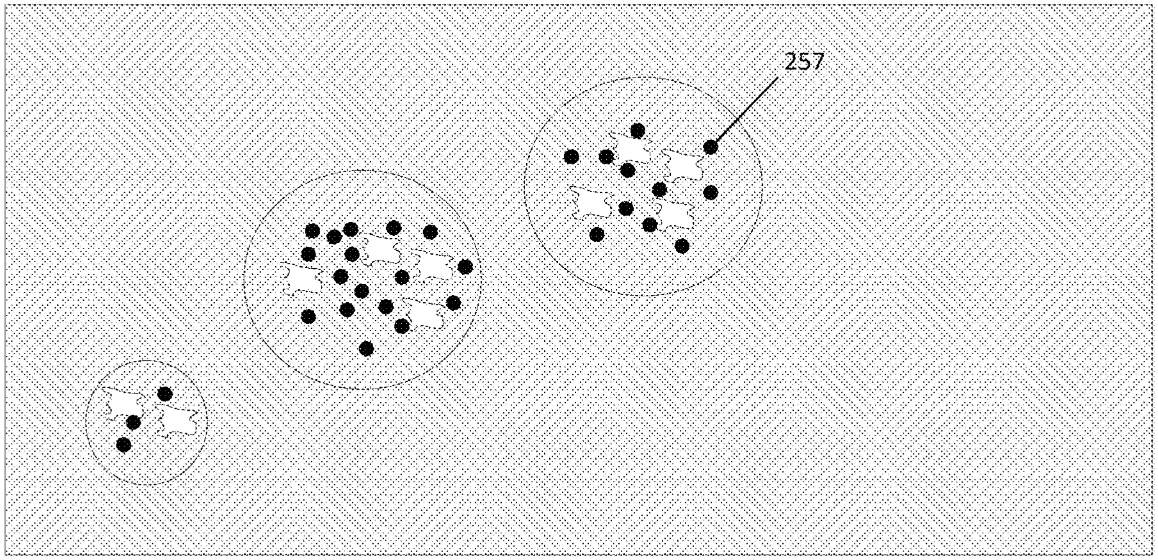

An alternative embodiment for measuring protein secretion profiles is illustrated in FIGS. 2E-2F. In this embodiment, a uniform distribution of protein-capture beads is attached to first surface (250) prior to loading cells. As illustrated in blow-up (244), the uniform distribution may include beads with antibodies specific for different proteins. After deposition of cells on surface (250), cells are located by detector (245) and hydrogel chambers are synthesized (246) by spatial energy modulating element (247). Cells are incubated under growth conditions, after which cells in each chamber are counted to determine a proliferation rate (253). As above, secreted proteins are detected by being captured by protein-capture beads and then labeled with detection antibodies (255). In some embodiments, porosity of the polymer matrix walls of the chambers is selected to prevent passage of cells but to allow the free passage of proteins. In other embodiments, such porosity is selected to prevent to passage of both cells and proteins. In the latter embodiment, an added step of depolymerizing the polymer matrix walls is included. Relative amounts of secreted proteins are determined (256) by either counting labeled beads of the different types adjacent to, or in the proximity of (257), the cells of each chamber, or by integrating the different fluorescent signals from the beads adjacent to, or in the proximity of, the cells of each chamber. As mentioned above, in addition to beads carrying protein-capture antibodies, other surfaces capable of carrying secreted protein capture antibodies include, but are not limited to, the first surface, the polymer matrix walls of a chamber, or a second surface. These surfaces capable of attaching secreted protein-capture antibodies are referred to herein as "protein capture surfaces."

In some embodiments, the above methods for correlating cellular characteristics with proliferation rate may comprise the steps: (a) providing a fluidic device comprising (i) a channel comprising a first surface, cells disposed on or adjacent to the first surface, and one or more polymer precursors, (ii) a spatial energy modulating element in optical communication with the first surface, and (iii) a detector that identifies positions of cells in the channel based on one or more optical signals therefrom; (b) synthesizing one or more chambers in the channel enclosing each of one or more cells by projecting light into the channel with the spatial energy modulating element such that the projected light causes cross-linking of the one or more polymer precursors to form polymer matrix walls of the chambers, wherein the positions of the synthesized chambers are determined by the positions of cells enclosed thereby identified by the detector; (c) incubating the cells under proliferation conditions; and (d) counting cells in each chamber to determine a proliferation rate thereof. In some embodiments, the first surface may comprise one or more capture elements for capturing one or more biological components of said cells, such as, secreted proteins, messenger RNAs, genomic DNA, or the like. In some embodiments, the step of synthesizing may be followed by a washing step to remove unreacted polymer precursors. In some embodiments, after such washing step (or as part of such washing step) cell culture medium may be loaded in the channel. In some embodiments, the above method further comprises: (i) incubating the cells with antibodies specific for surface proteins whose relative expression permits identification of the cells, wherein each of such antibodies has an oligonucleotide label comprising an antibody-specific barcode capable of being captured by the capture element; (ii) optionally loading into the channel a releasing reagent so that oligonucleotide labels of antibodies attached to the one or more cells are released and captured by the capture elements (if the oligonucleotide labels are attached by a scissile linkage); (iii) optionally depolymerizing the polymer matrix walls of the chambers; (iv) loading said channel with reagents to copy said captured oligonucleotide labels to produce complementary DNAs thereof; and (v) sequencing the complementary DNAs to identify the captured oligonucleotide labels. In some embodiments, cDNAs of captured labels may be sequenced at or near their capture locations by the steps of (a) amplifying said complementary DNAs, (b) sequencing the amplified complementary DNAs, and (c) determining relative expression of the surface proteins for said cells of each of said chambers. Oligonucleotide labels may be attached to antibodies (or other binding moieties) with cleavable linkages well-known in the art. Such oligonucleotide labels attached to antibodies by cleavable linkages may be cleaved, or released from the antibody, by cleavage reagents or agents, or (equivalently) releasing reagents or agents, which may be chemical, physical, or electrical in nature. Reagents to copy captured oligonucleotide labels include a DNA polymerase, dNTPs, and associated buffer and salt solution to extend a capture oligonucleotide using an oligonucleotide label as a template. In some embodiments, cDNAs of captured labels may be sequenced on an external sequencing instrument after (optional amplification and) elution from the channel. For the latter sequencing, the capture elements on the first surface comprise spatial barcodes and cDNAs of the captured oligonucleotide labels each comprise a spatial barcode. After sequencing the cDNA-spatial barcode conjugates, the cDNA may be assigned to a chamber based on the spatial barcode.

In other embodiments, cell proliferation may be correlated to protein secretion by the following steps: (a) providing a channel comprising a protein capture surface comprising protein-capture antibodies that bind proteins secreted by the cells; and (b) detecting protein secreted by the cells by an amount of labeled protein detection antibodies for each protein bound to the protein capture surface adjacent to the cells. In some embodiments, protein capture surfaces comprise protein-capture beads.

In some embodiments, cell proliferation rates may be correlated with cellular transcriptomes following the steps described below for converting mRNA from cells to cDNAs and sequencing the resulting cDNAS. Briefly, after the counting step, the following further steps may be implemented: (a) loading the channel with a lysing reagent so that mRNAs of the cells are released and captured by the capture elements; and (b) loading the channel with reverse transcription reagents to copy the captured oligonucleotide labels to produce complementary DNAs thereof; and (c) sequencing the complementary DNAs. It is understood that a sequencing step may comprise additional steps in particular embodiments including, but not limited to, tagmentation, adding adaptors, cleaving the cDNA to form appropriate lengths for sequencing, and the like. In some embodiments, an additional step may be implemented for depolymerizing or degrading the polymer matrix walls of the chambers after mRNA capture. Reverse transcription reagents comprise conventional reagents for reverse transcription; namely, a reverse transcriptase (such as, a Moloney murine leukemia virus (MMLV)), dNTPs, optional RNase inhibitor, buffer. The sequencing step may be carried out at the sites of the captured mRNAs (in situ) or cDNAs may include a spatial barcode and be eluted and sequenced on a separate sequencing instrument ("external" sequencing). For in situ sequencing, further steps may include (i) amplifying the complementary DNAs, e.g. by bridge amplification, or like method, (ii) sequencing the amplified complementary DNAs, e.g. by a sequencing-by-synthesis technique, and (iii) determining relative expression of the mRNAs for the cells of each of the chambers. For external sequencing, further steps may include (i) providing capture elements comprising spatial barcodes, (ii) synthesizing cDNAs comprising spatial barcodes, and (iii) eluting and sequencing the cDNAs and correlating each cDNA with a chamber location by its spatial barcode.

Cytotoxicity Assays

Figure 3A:
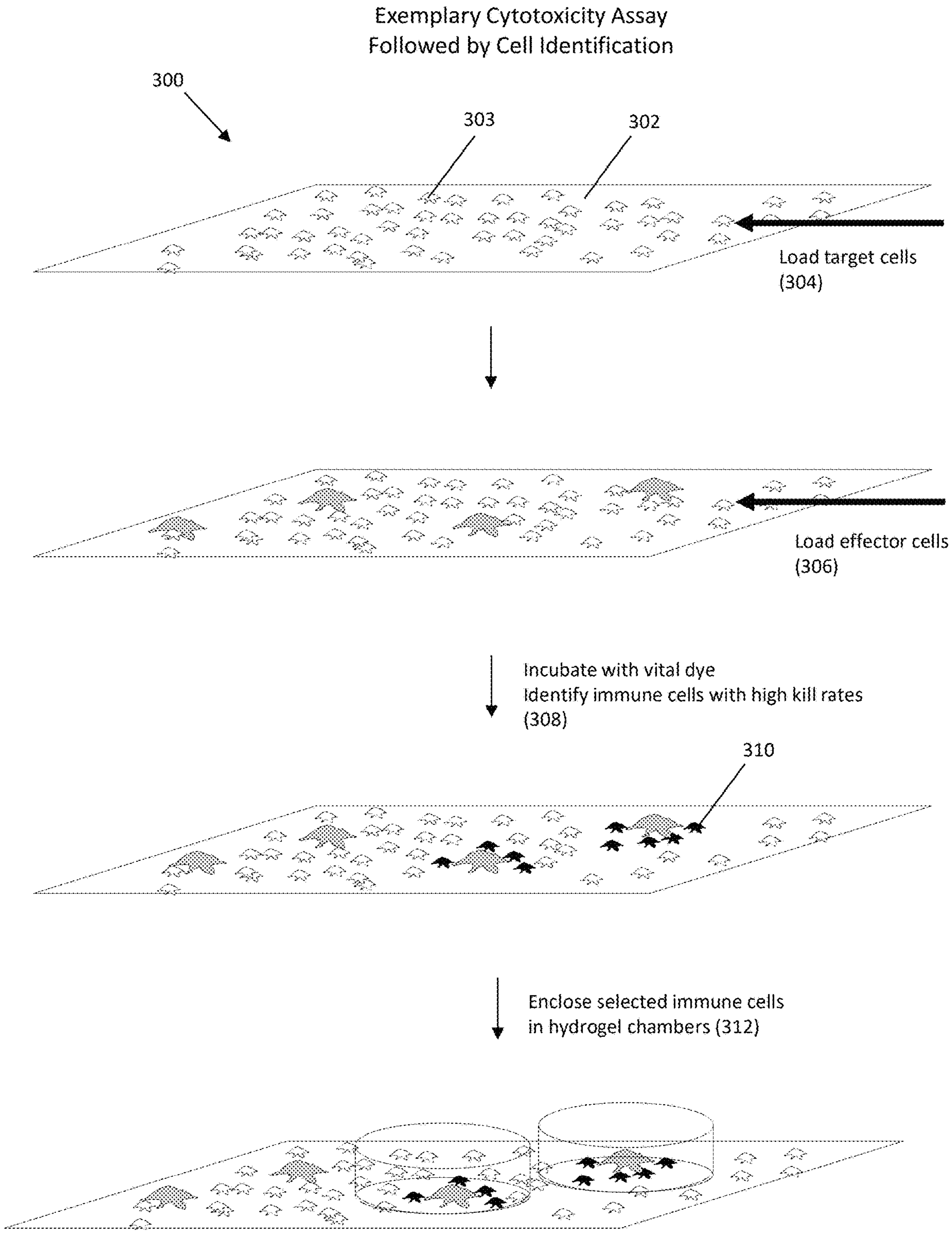
FIGS. 3A-3B illustrate steps of an assay for determining cytotoxicity of cells of a population. Subsequent assays to identify cells having desirable cytotoxicity values can be carried out as shown in FIGS. 2B-2G.
Figure 3B:
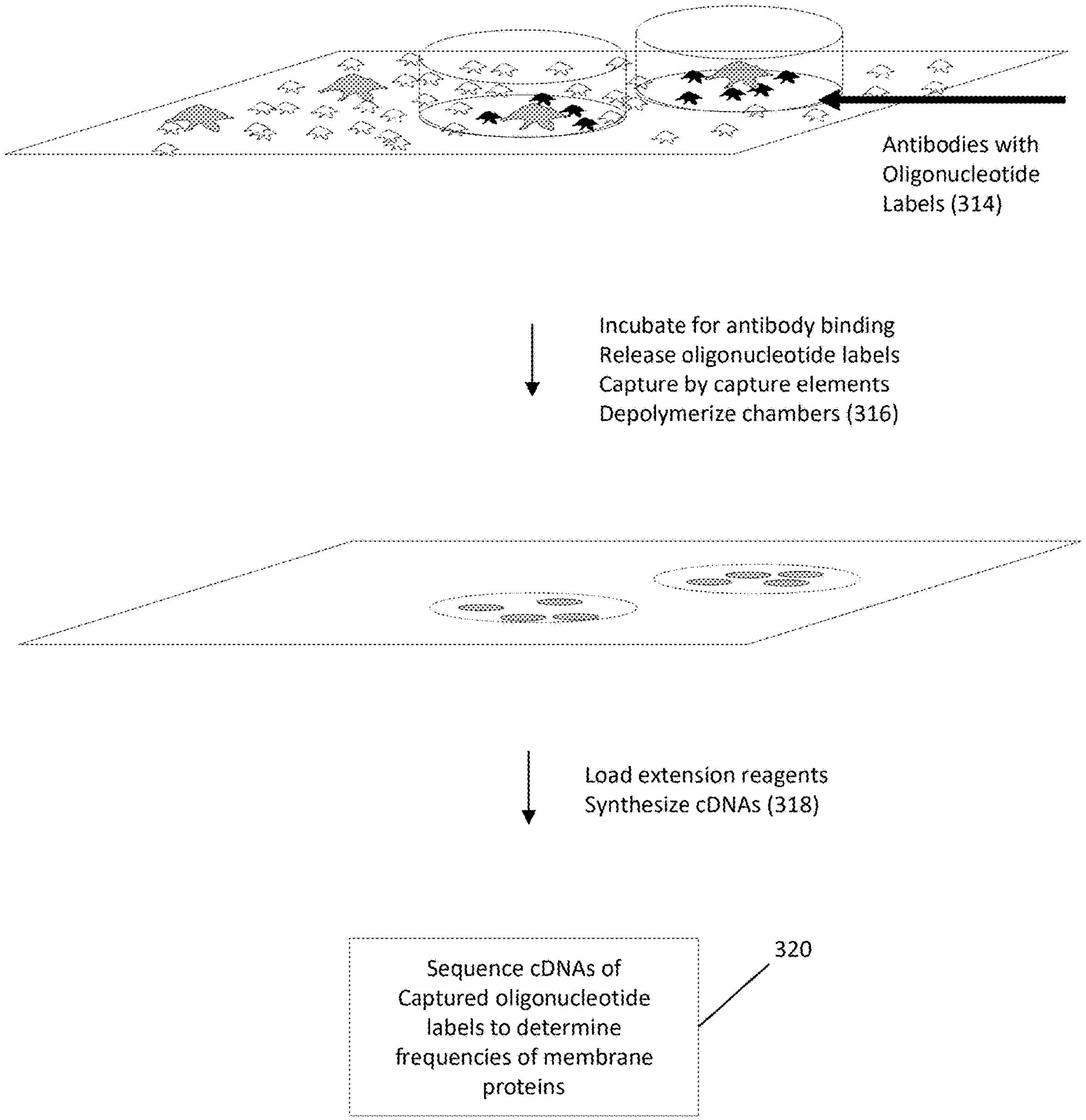

As with cell proliferation, a measure of cell cytotoxicity against a target cells population may be correlated to other cellular characteristics including, but not limited to, cell membrane protein expression, cell protein secretion profile, transcriptome and the like. Target cells may comprise a sample of tumor cells of a patient, or target cells may be from a cell line, e.g. tumor cell line, such as, hepatic tumor cell line, SK-HEP-1, Chava et al, J. Vis. Exp., 2020 Feb. 22: (156): 10.3791/60714. Steps of an exemplary cytotoxicity assay are illustrated in FIGS. 3A-3B. Target cells (303) are loaded (304) into channel (300) so that they are disposed on first surface (302), after which effector cells are loaded (306) and are disposed on first surface (302) along with target cells. "Effector cells" means cells whose cytotoxic capacity is being measured. In some embodiments, effector cells are cells engineered for a therapeutic purpose, such as, treatment of a cancer. Target cells and effector cells are incubated (308) together with a vital dye that generates an optical signal in response to a characteristic of viable cells or dead cells, which permits dead cells to be enumerated. An exemplary vital dye for live cells includes, but is not limited to, Hoechst 33342. An exemplary vital dye for dead cells includes, but is not limited to, 7-AAD, e.g. Schmid et al, Cytometry, 15:12-20 (1994); Bradford et al, poster entitled "Dead cell stains in flow cytometry: a comprehensive analysis," Molecular Probes (Eugene, OR). After such incubation, a measure of cytotoxicity may be determined by counting dead target cells (310) adjacent to, or in the proximity of, each effector cell. In some embodiments, individual effector cells may be enclosed by chambers immediately after loading to ensure that the only dead target cells counted are those killed by the enclosed single effector cell. In other embodiments, effector cells may be enclosed by chambers at a later time if dead target cells are readily associated with dead target cells, e.g. by proximity. Effector cells may then be identified by (for example) cell surface markers, protein secretions, transcriptome, or the like. For identification by cell surface markers, effector cells may be enclosed by hydrogel chambers (312) (if not already enclosed), and antibodies with oligonucleotide labels may be loaded into the channel (314). In some embodiments, non-enclosed cells may be removed by a washing step or other change of reagents in the channel. After incubation (316) for antibody binding to target surface proteins, oligonucleotide labels are released and captured by capture elements. After such capture, chambers are optionally depolymerized and extension reagent are loaded for copying the captured oligonucleotides by extending capture element oligonucleotides with the captured oligonucleotide as a template (318). The resulting cDNAs are amplified and sequenced (320) as described above for the cell proliferation assays.

Likewise, the cells from different channels enclosed as shown in step (312), which have been measured for cytotoxicity, may be subjected in those different channels to different assays to determine different cellular characteristics from cell surface markers. Such different assays include, but are not limited to, protein secretions, vector copy number, transcriptome, and the like.

In some embodiments, additional steps may be implemented to reduce or eliminate spurious signals generated by proteins or mRNAs of target cells. For example, after incubation for killing and after labeled antibodies are bound to cell surface proteins, effector cells in the chambers may be encapsulated or encased in a gel (or a second chamber may be synthesized) separating it from target cells in the first chamber. After counting, the target cells in the first chamber may then be lysed and removed by washing. After such removal, the gel encasing the effector cells may then be depolymerized to permit antibody labels or mRNAs to be released and captured by capture elements of the first surface. In some embodiments, the gel encasing the effector cells is degradable, e.g. by a reducing agent, and has an average pore size sufficiently small to prevent passage of most mRNA of interest (for example, mRNA of 300 nucleotides or greater) until depolymerization.

In some embodiments, a method of correlating cellular characteristics with cytotoxicity may comprise the steps of: (a) providing a fluidic device comprising (i) a channel comprising a first surface and a population of target cells disposed thereon, (ii) a spatial energy modulating element in optical communication with the first surface, and (iii) a detector that identifies positions of cells in the channel based on one or more optical signals therefrom; (b) loading each channel with effector cells and one or more polymer precursors so that the effector cells are disposed on or adjacent to the first surfaces; (d) synthesizing one or more chambers in the channels each enclosing an effector cell by projecting light into the channel with the spatial energy modulating element such that the projected light causes cross-linking of the one or more polymer precursors to form polymer matrix walls of the chambers, wherein the positions of the synthesized chambers are determined by the positions of effector cells enclosed thereby identified by the detector; (e) incubating the target cells and the effector cells with a vital stain that identifies dead cells; and (f) counting dead cells in each chamber to determine a measure of cytotoxicity of the effector cell enclosed thereby. In some embodiments, the vital stain generates an optical signal in dead cells but not living cells. In some embodiments, the step of synthesizing may be followed by a washing step to remove unreacted polymer precursors. In some embodiments, after such washing step (or as part of such washing step) cell culture medium may be loaded in the channel.

In some embodiments, after an effector cell's cytotoxic capacity is measured, e.g. by counting adjacent, or in-chamber, dead cells, the effector cell may be identified by other assays that measure characteristics such as surface proteins, protein secretion, and the like. Assays for the identification of effector cells by their cell surface proteins may include the following steps: (i) incubating the cells with antibodies specific for surface proteins whose relative expression permits identification of the cells, wherein each of such antibodies has an oligonucleotide label comprising an antibody-specific barcode capable of being captured by the capture element; (ii) loading into the channel a releasing reagent so that oligonucleotide labels of antibodies attached to the one or more cells are released and captured by the capture elements; (iii) optionally depolymerizing the polymer matrix walls of the chambers; (iv) loading the channel with reagents to copy the captured oligonucleotide labels to produce complementary DNAs thereof; and (v) sequencing the complementary DNAs to identify the captured oligonucleotide labels, and thereby determine a cell surface protein profile of each effector cell. As noted above, in some embodiments, before the loading of a releasing reagent, the following steps may be performed: (a) encasing the effector cell of each chamber in a degradable encasing gel that prevents the escape of bound oligonucleotide labeled antibodies or mRNAs, (b) lysing target cells by loading a lysing reagent into the channel, and (c) a washing step to remove target cell bound oligonucleotide-labeled antibodies and mRNAs.

In some embodiments, such cDNAs may be sequenced in situ with the following steps: (a) amplifying the complementary DNAs, (b) sequencing the amplified complementary DNAs, and (c) determining relative expression of the surface proteins for the cells of each of the chambers. In alternative embodiments, such cDNAs may be sequenced externally as follows: providing capture elements with spatial barcodes so that the cDNAs synthesized from the captured oligonucleotide labels include spatial barcodes, amplifying the cDNAs, releasing (or de-hybridizing) and eluting the amplified cDNA (or their complements), sequencing the cDNAs, wherein the spatial barcode permit the identification of the chambers from which the cDNAs originated.

Cytotoxicity of cells may be correlated to protein secretion profiles using the additional steps as described for cell proliferation. In one embodiment, such steps may comprise: (i) loading the channel with a second reaction mixture comprising second polymer precursors and protein capture beads comprising protein-capture antibodies that bind proteins secreted by the cells; (ii) synthesizing second chambers enclosing each of the one or more chambers by projecting light into said channel with said spatial energy modulating element such that the projected light causes cross-linking of the one or more polymer precursors to form polymer matrix walls of second chambers, wherein the positions of the synthesized second chambers are determined by the positions of the (initial) chambers enclosed thereby identified by the detector; and (iii) depolymerizing the chambers so that the protein capture beads in each second chambers mix with the cells enclosed by the depolymerized chamber therein. The above method may further include: incubating the cells with the protein capture beads; and detecting protein secreted by the cells by an amount of labeled protein detection antibodies for each protein bound to protein-capture beads adjacent to said cells.

In alternative embodiments, the channel further comprises disposed thereon protein capture beads comprising protein-capture antibodies that bind proteins secreted by the cells; and the method further comprises detecting protein secreted by the cells by an amount of labeled protein detection antibodies for each protein bound to protein-capture beads adjacent to said cells.

Vector Copy Number Assays

Figure 4A:
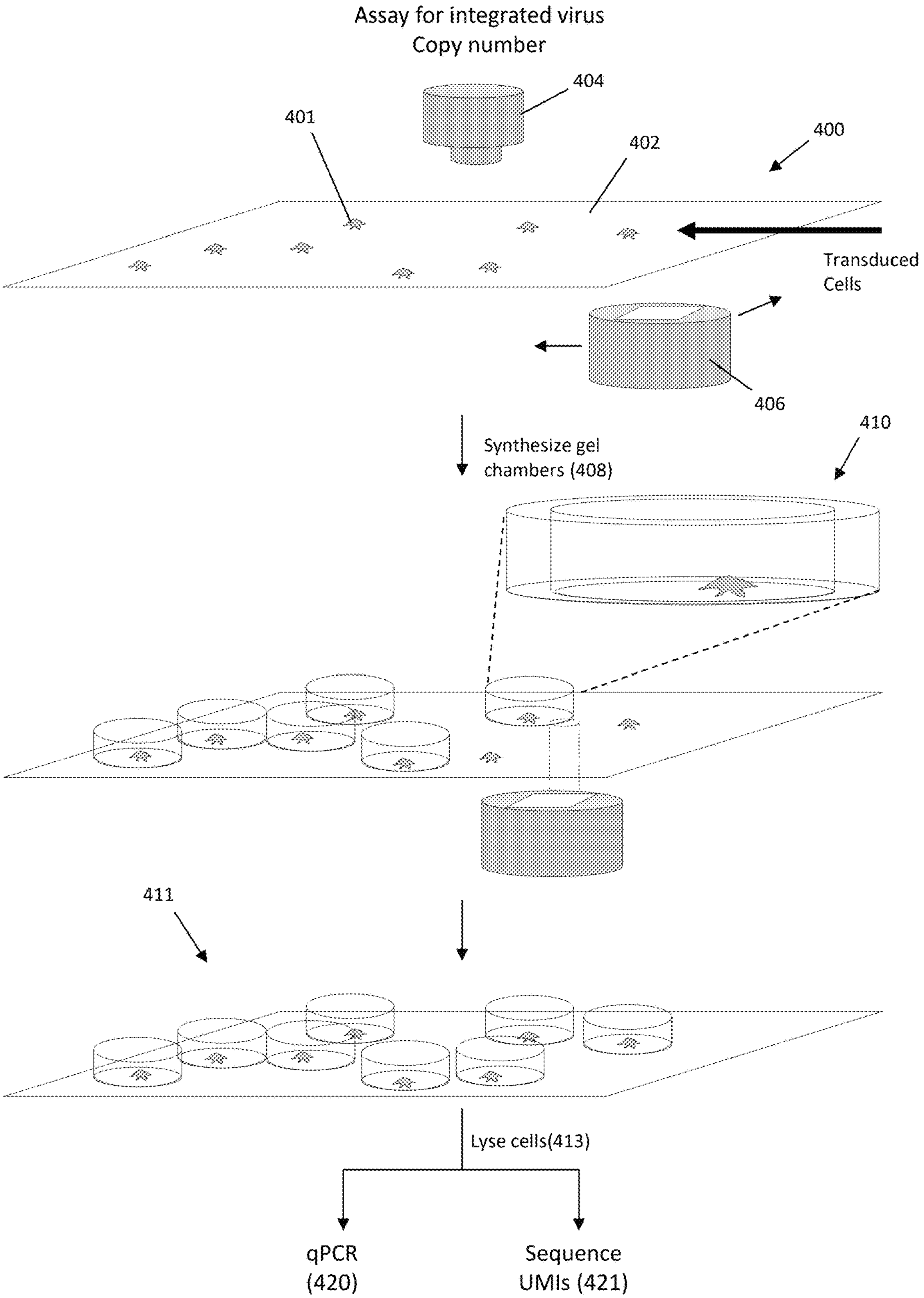
FIGS. 4A-4B illustrate an assay for determining integrated vector copy number in transduced cells.
Figure 4B:
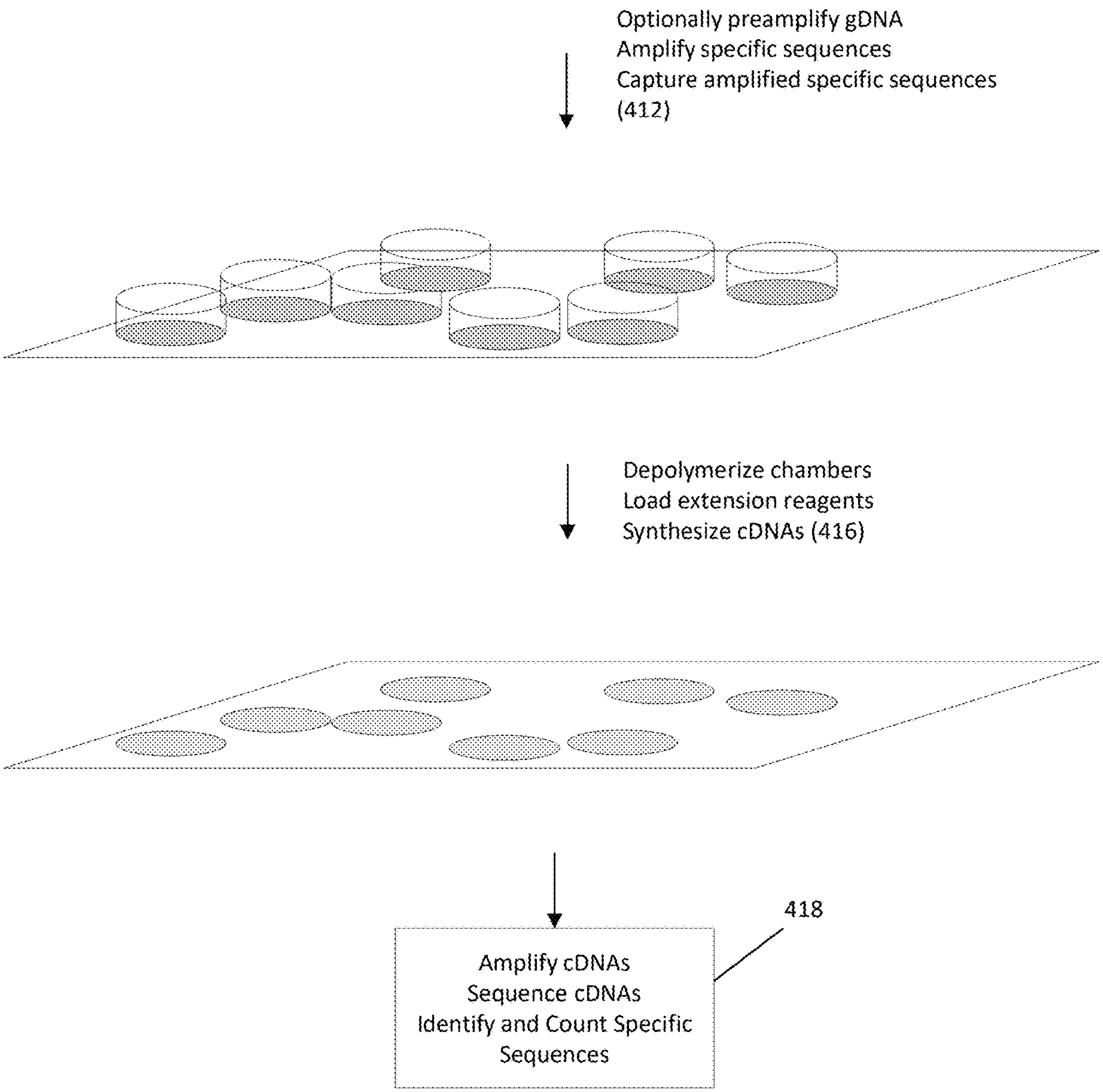

Vector copy number in cells engineered for therapy is important because of the increased risk of oncogenesis if copy number is too high, such as, higher than about five copies per cell, e.g. Chen et al, Cytotherapy, 22(5), supplement, S142 (2020); Paugh et al, Scientific Reports, 11: 389 (2021). In accordance with the invention, vector copy number may be measured by single cell quantitative PCR in chambers or by counting unique molecular identifiers (UMIs) amplified and sequenced from single cells in chambers or like measure. For either assay, cells may be prepared as illustrated in FIG. 4A. Namely, engineered or transduced cells may be loaded into channel (400) so that cells (e.g. 401) are disposed onto first surface (402), after which detector (404) records the locations of cells on first surface (402) and spatial energy modulating element (406) synthesizes (408) chambers (411) separately enclosing single cells. Polymer precursors and conditions may be selected so that the porosity of the polymer matrix walls of the chambers permit the transit of proteins, lysis reagents, mRNAs, and the like, but retain genomic DNA, for example, using formulations as described in Spencer et al, ISME Journal, 10: 427436 (2016); and Tamminen et al, Frontiers Microbiology: Methods, 6:195 (2015). Cells may be lysed (413) as described in Tamminen et al (protease K followed by lysozyme) or as described by Zhang et al, Proc. Natl. Acad. Sci., 89: 847-5851 (1992) (alkaline lysis: 200 mM KOH/50 mM dithiothreitol followed by neutralization with 900 mM Tris-HCL, pH 8.3/300 mM KCl/200 mM HCl); or like methods. After such treatment, genomic DNA retained in the chambers may be further analyzed by qPCR (420), such as described by Vaninsberghe et al, PlosOne, 13(1): e0191601 (2018), or by sequencing (421) as outlined in FIG. 4B, if the vectors comprise UMIs, e.g. Porter et al, Genome Biology, 15: R75 (2014).

For qPCR (420), in some embodiments, channel (400) is loaded with a PCR reaction mixture including polymerase, primers, taqman probe, buffers and salts. In some embodiments, to run the PCR, the flow cell is moved to a temperature cycling station. As the PCRs progress in the various chambers, detector (404) records the accumulation of signal from the taqman probes at each chamber, which can be converted into copy numbers. In some embodiments, the channel containing chambers in which qPCR reactions are occurring may be loaded with a blocking agent to prevent diffusion of labeled taqman fragments from the chambers. Such blocking agent may include polymer precursors which may be polymerized in the spaces surrounding the chambers.

For sequencing (412), optionally, the retained genomic DNA may be pre-amplified by a whole genome amplification technique, e.g. as described by Zhang et al (cited above), after which desired sequences, e.g. those containing the virus UMIs, are specifically amplified (e.g. by PCR or a linear amplification technique) and captured by capture elements (412). In some embodiments, the UMI along with a "handle" segment (an oligonucleotide segment complementary to a capture oligonucleotide) is amplified to facilitate the capture by a capture element of the first surface. As describe above, chambers may be depolymerized, extension reagents loaded, and cDNAs synthesized (416) which contains a copies of the UMIs. After amplification, cDNAs may be sequenced either in situ or externally and the number of UMIs with different sequences are determined to give a virus copy number for the cells of each chamber.

The above methods may be implemented by first enclosing the engineered cells in hydrogel chambers in accordance with the invention, namely, by the steps of (a) providing a fluidic device comprising (i) one or more channels each comprising a first surface, (ii) a spatial energy modulating element in optical communication with each first surface, and (iii) a detector that identifies positions of cells in each channel based on one or more optical signals therefrom; (b) loading each channel with cells and one or more polymer precursors so that the cells are disposed on or adjacent to the first surfaces; (c) synthesizing one or more chambers in each channel, each chamber enclosing a cell by projecting light into each channel with the spatial energy modulating element such that the projected light causes cross-linking of the one or more polymer precursors to form polymer matrix walls of the chambers, wherein the positions of the synthesized chambers are determined in each channel by the positions of the cells enclosed thereby identified by the detector; (d) loading one or more channels with assay reagents (such as, for example, lysing reagents, followed by amplification reagents, followed by cDNA synthesis reagents, and so on); and (e) incubating the cells in each channel under assay conditions, which include PCR conditions, rolling circle amplification conditions and/or sequencing conditions, to generate signals from chambers of each channel indicative of a sequence copy number, such as, a vector copy number (VCN). For enumerating copy numbers of specific (or predetermined) nucleotide sequences, such as UMIs, in some embodiments, the following steps may be implemented: (i) lysing the cells to release genomic DNA; (ii) amplifying the one or more nucleotide sequences; (iii) capturing the amplified one or more nucleotide sequences by the capture elements; (iv) loading the channels with reagents to copy captured one or more nucleotide sequences to produce complementary DNAs thereof; and (v) sequencing the complementary DNAs to identify the copy numbers of the one or more nucleotide sequences. Embodiments of special interest comprise predetermined nucleotide sequences that are barcodes, especially barcodes that are or comprise UMIs. The amplified nucleotide sequences typically comprise one or two primer binding sites, a barcode and a sequence complementary to the capture oligonucleotides of the capture elements. The amplified nucleotides may include additional segments for increasing the molecular weight of the amplified products to prevent or inhibit passage through the polymer matrix walls of the hydrogel chamber. From the sequencing data the number of different UMIs may be identified which gives the viral copy number for the cell.

For enumerating copy numbers by quantitative PCR or other amplification methods, in some embodiments, the following steps may be implemented: (i) lysing the cells to release genomic DNA; (ii) loading said channels with amplification reagents that generate a signal proportional to a copy number of the one or more nucleotide sequences of the genomic DNA; (iii) amplifying the one or more nucleotide sequences to generate signals monotonically related to the copy numbers of the one or more nucleotide sequences. In some embodiments, the amplification reagents may be quantitative PCR reagents, bridge PCR reagents, or rolling circle amplification reagents. In some embodiments, quantitative PCR reagents comprise an amplification buffer, a polymerase with 5'→3' exonuclease activity, primers, dNTPs, and a taqman probe In further embodiments, copy numbers may be determined by copying the selected genomic sequences, capturing them with capture elements, synthesizing cDNAs from the selected genomic sequences, then either forming clusters of the cDNAs by bridge PCR or DNA nanoballs by rolling circle amplification, after which the clusters or DNA nanoballs may be counted for a measure of copy number. When quantitative PCR is employed, a signal related to copy number may be an optical signal or a cycle number. When bridge PCR is employed, the first surface may comprise bridge PCR primers and a signal related to copy number may be the number of clusters formed. When rolling circle amplification is employed, a signal related to copy number may be a number of DNA nanoballs formed. Clusters and DNA nanoballs may be detected by a wide variety of techniques including, but not limited to, use of fluorescently labeled dNTPs, double stranded DNA dyes, and the like.

Integration Site Analysis

Figure 4C:
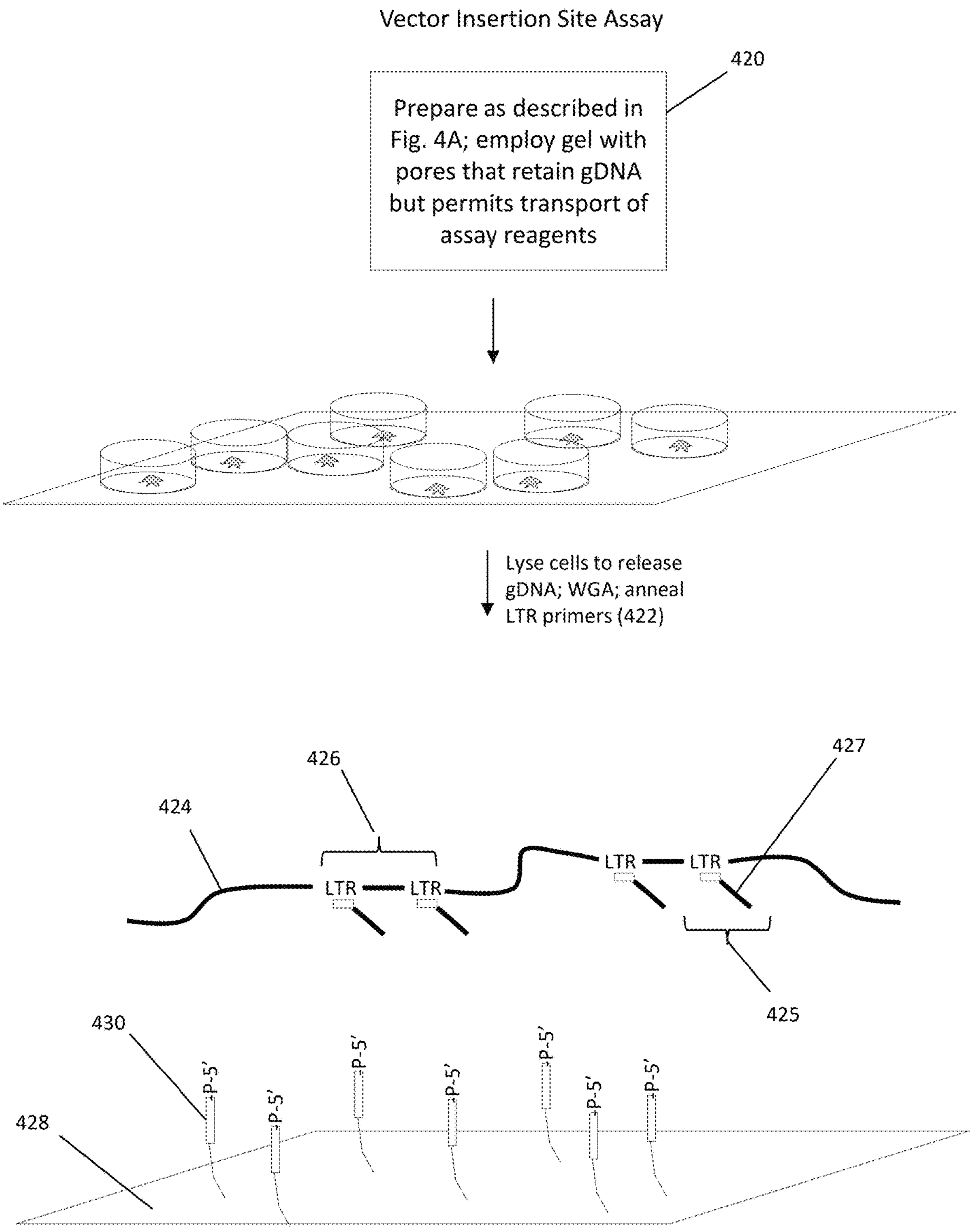
FIGS. 4C-4F illustrate an assay for determining integrated vector copy number and insertion site of transduced cells.
Figure 4D:
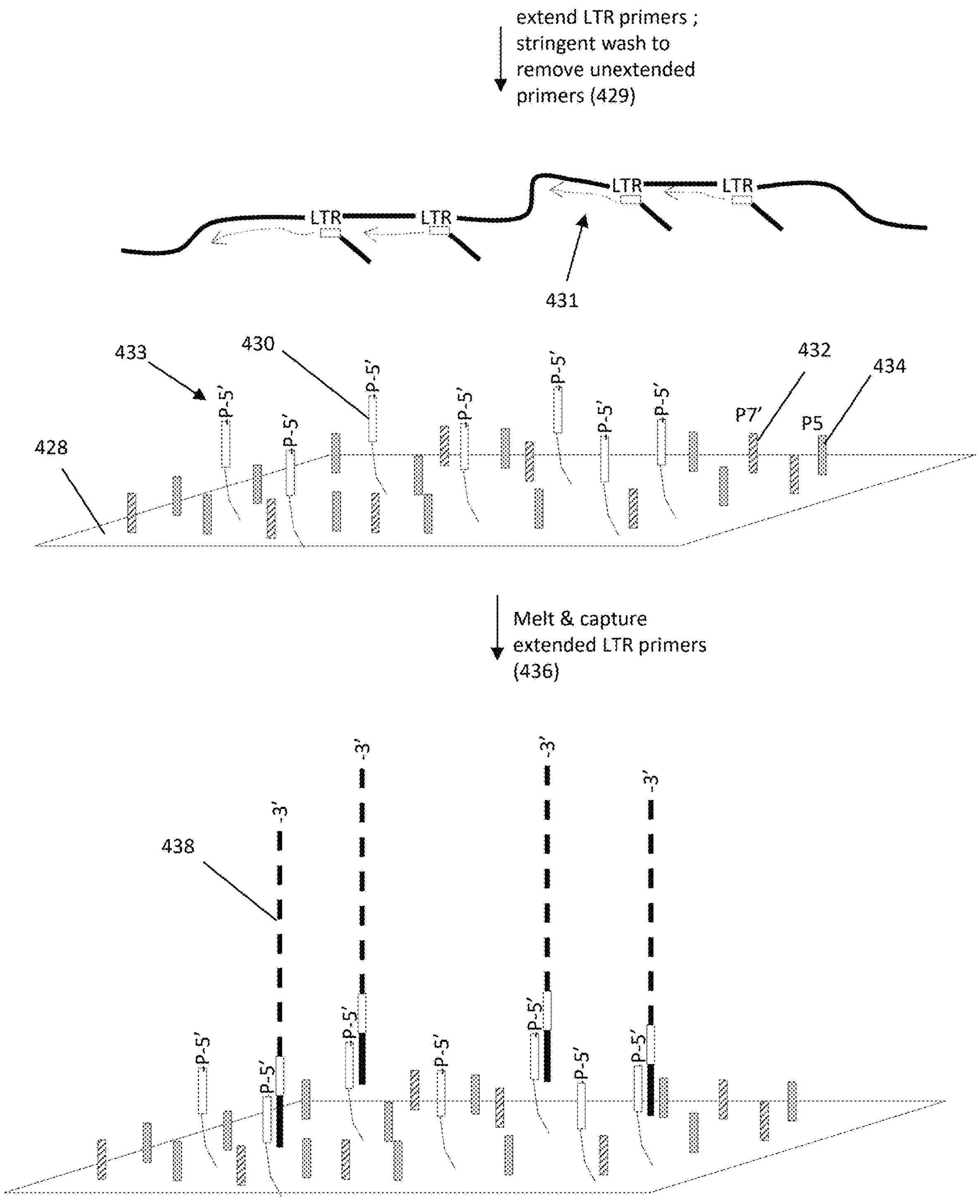
Figure 4E:
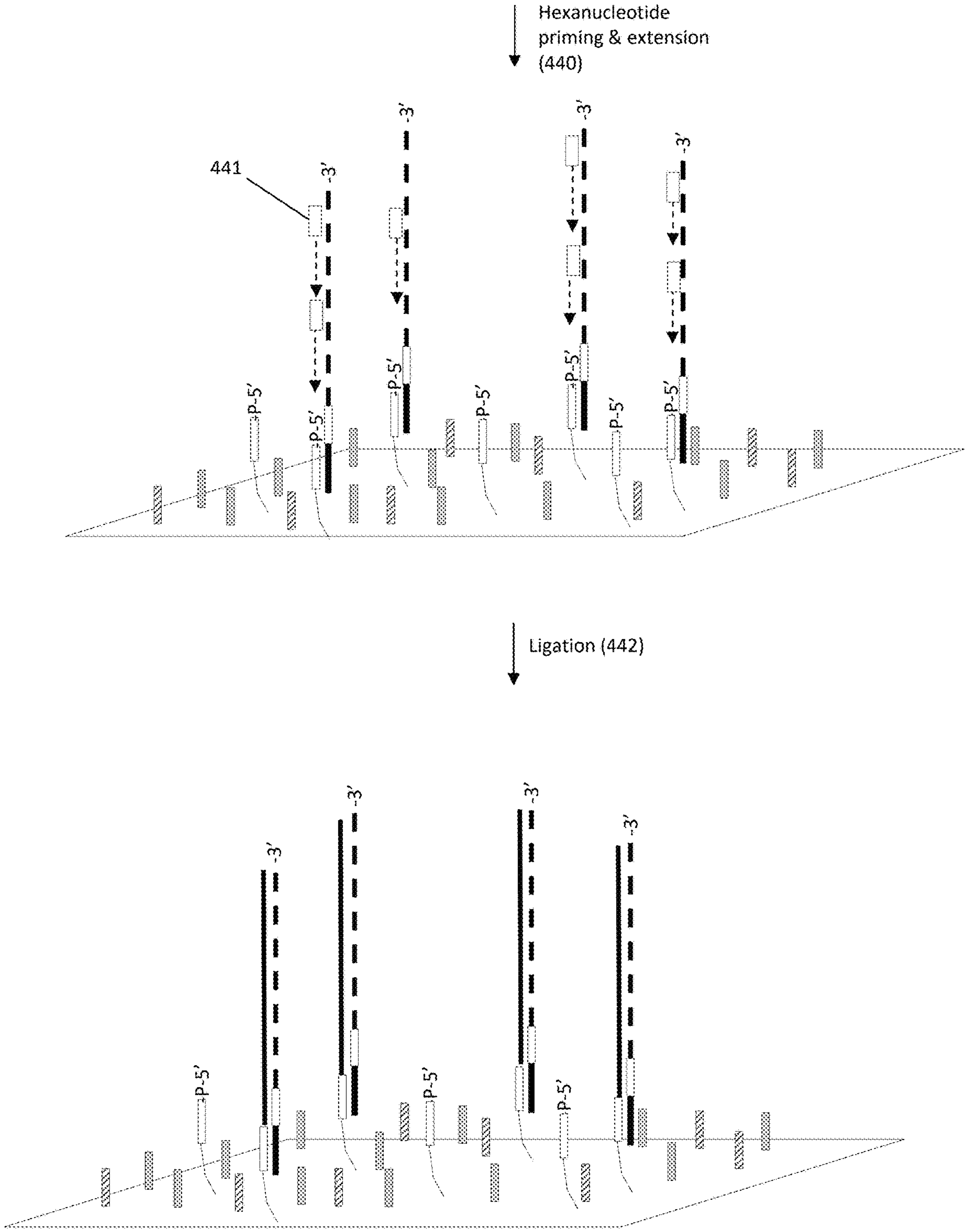
Figure 4F:
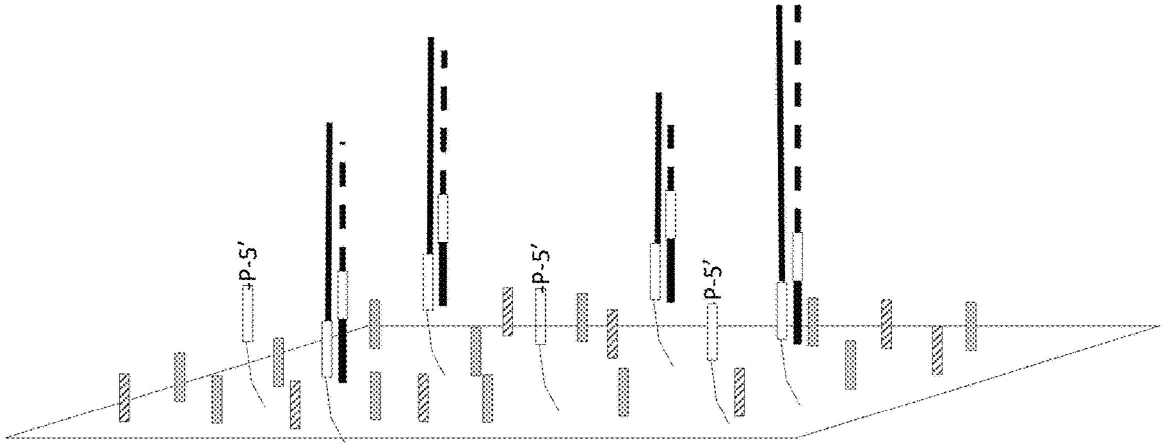
Figure 4F:
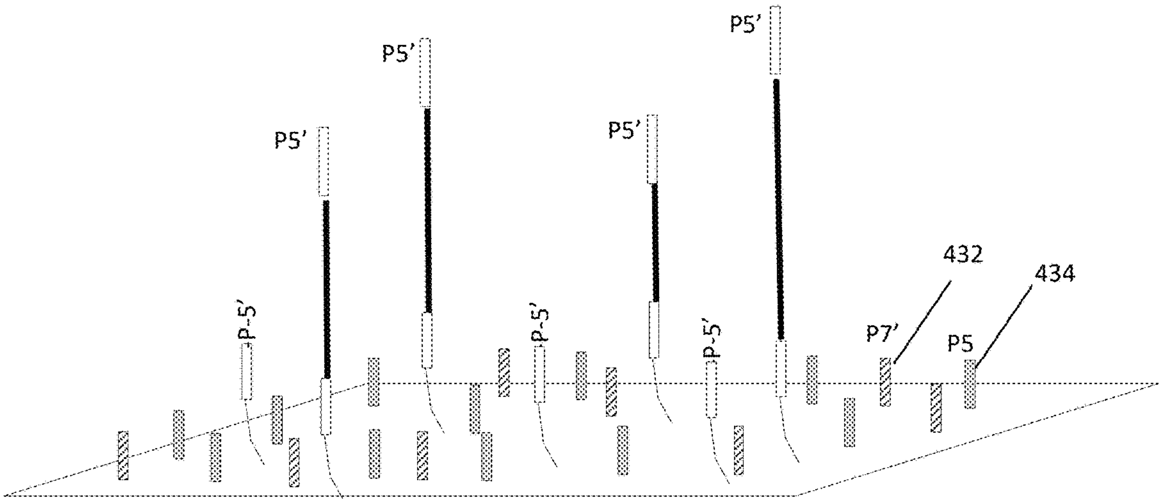

The site or sites of integration of viral vectors in the genomes of therapeutic cells is of vital interest because of possible disabling or altering of the expression of one or more important genes, which is sometimes referred to as genotoxicity or insertional mutagenesis, e.g. Biasco et al, Molecular Therapy: Methods & Clinical Development, 8: 21-30 (2018); Cornetta et al, Molecular Therapy: Methods & Clinical Development, 28: 28-39 (2023); Desfarges et al, Viruses, 2: 111-130 (2010); and the like. Insertion sites may be detected in populations of cells in accordance with the invention, as exemplified in FIGS. 4C-4F. The general concept of the measurement approaches is to anneal primers to known sequences of vectors integrated into the genome, extend the primers into the genomic DNA of the host, then identify the host gDNA and the site of integration. Individual cells are enclosed in hydrogel chambers as described in FIG. 4A, wherein hydrogel porosity is selected (420) so that the walls of the chamber prevent the passage of genomic DNA, but permit the passage of reagents, such as deoxynucleoside triphosphates (dNTPs), DNA polymerase, primers, and the like, for example, as disclosed by Spencer et al, ISME J., 10: 427-436 (2010). Cells are lysed (422) to release genomic DNA (gDNA) (424), after which the released gDNA is amplified, denatured and combined with vector-specific primers (e.g., 425). Such lysing may be carried out with a variety of methods known in the art by loading lysing reagent into channels, e.g. Spencer (cited above); Cui et al, Proc. Natl. Acad. Sci., 86: 9389-9393 (1989); Deleye et al, Scientific Reports, 5: 11711 (2015); and the like. After lysing, whole genome amplification (WGA) may be performed using techniques known in the art, e.g. primer extension preamplification PCR (PEP-PCR), degenerate oligonucleotide primer PCR (DOP-PCR), multiple displacement amplification (MDA), multiple annealing and looping based amplification cycles (MALBAC), or the like, disclosed in the following references, Volozonoka et al, Int. J. Mol. Sci., 23: 4819 (2022); Hou et al, GigaScience, 4: 37 (2015); Yu et al, Anal. Chem., 86: 9386-9390 (2014); or the like. FIG. 4C shows integrated vectors (426) as linear segments of DNA flanked by long terminal repeat (LTR) sequences. In some embodiments, other vector regions may be used as primer binding sites. LTR primers (425) have 5' oligonucleotide tails (427) that have sequences complementary to capture oligonucleotides (430) on first surface (428) within the chamber. LTR primers are extended by a DNA polymerase in the presence of dNTPs (e.g. 431), after which the chambers are washed at a stringency (e.g. salt, heat, etc.) high enough to destabilize and remove non-extended LTR primers but not so high as to remove extended LTR primers (429). Extended LTR primers are then melted from the gDNA and are captured (436) by capture oligonucleotides (430) by hybridizing to the 5' tails (427) of the extended LTR primers. The capture oligonucleotides (430) are attached to surface (428) by their 3' ends and their 5' ends have attached 5'-phosphate groups. Capture oligonucleotides may have additional features depending of embodiment. For example, if sequences of the extension regions of the extended LTR primers are to be determined in situ, capture oligonucleotides may include primers for bridge amplification. On the other hand, if sequences of the extension regions are to be determined off-instrument, capture oligonucleotides may include spatial barcodes for identifying sequences associated with the same cell. In FIG. 4D, surface (428) is illustrated with so-called P7' (432) and P5 (434) sequences for bridge PCR; thus, capture oligonucleotides (430) would include P7 sequences for initiating bridge PCR after LTR primer extensions are copied and removed. The actual sequences of the P5 and P7' regions is a matter of design choice for one of ordinary skill in the art.

After capture of extended LTR primers (436), random-sequence hexanucleotide primers (441) are annealed to extension regions (438) and are themselves extended (440), after which the synthesized strand is ligated to the 5' end of the capture oligonucleotides, e.g. using protocols described by Schmidt et al, Nature Methods, 4(12): 1051-1057 (2007); Kalle et al, U.S. Pat. No. 6,514,706; which are incorporated herein by reference. Alternatively, the 3' ends of extension regions (438) may be extended by a terminal deoxynucleotidyltransferase (TdT) to generate a homopolymer tail to which a complementary primer may be annealed and extended to the 5' end of capture oligonucleotide (430). The copied sequence is then ligated to capture oligonucleotide (430), after which the resulting construct is treated with a restriction endonuclease to produce a known sequence end distal to surface (428). The restriction endonuclease is selected to maximize the probability of retaining enough extension region for uniquely identifying its location in the engineered cell's genome (e.g. about 18 nucleotide for human). In some embodiments, a restriction endonuclease is selected which has a 4-nucleotide recognition site and leaves a 4-nucleotide overhang after cleavage. After such cleavage, double stranded adaptors are ligated to the ends of the double stranded fragments attached to surface (428). As noted in FIG. 4F (446), the sequences of the adaptored strands may be determined in situ by conducting a surface amplification followed by sequencing reactions, or they may be determined off surface (428) by amplifying by PCR and eluting the amplicon. In the former case, capture oligonucleotides (430) include P7 sequences at their ends proximal to surface (428). In the latter case, capture oligonucleotides (430) include spatial barcodes at their ends proximal to surface (428).

In some embodiments, the above method for vector integration site determination for a population of cells may be implemented by (a) synthesizing one or more hydrogel chambers enclosing each of one or more cells disposed on a surface of a channel; (b) lysing the cells so that genomic DNA of each cell is released into its hydrogel chamber; (c) amplifying the genomic DNA of each cell; (d) annealing a vector-specific-primer to the amplified genomic DNA, (e) extending the vector-specific primer so that an extension product is formed that includes a copy of a segment of said genomic DNA, and (f) identifying from the segment a site of each vector integrated into said genomic DNA of each said cell. In some embodiments, a vector-specific primer comprises a primer complementary to a vector sequence but not to a genomic sequence of the cell. In some embodiments, whenever a vector is a retrovirus, a vector-specific primer may be complementary to a sequence of a long terminal repeat (LTR) element. Such vector-specific primers are sometimes referred to herein as "LTR primers." One of ordinary skill would recognize that the degree, or length, of the extension of a vector-specific primer into an adjacent region of genomic DNA must be of a magnitude sufficient for identifying uniquely the position of the integrated vector in a cellular genome. For human genomes, in some embodiments, the length of such extension comprises at least 18 nucleotides of cellular genomic DNA.

Genomic Copy Number Variation

Figure 4G:
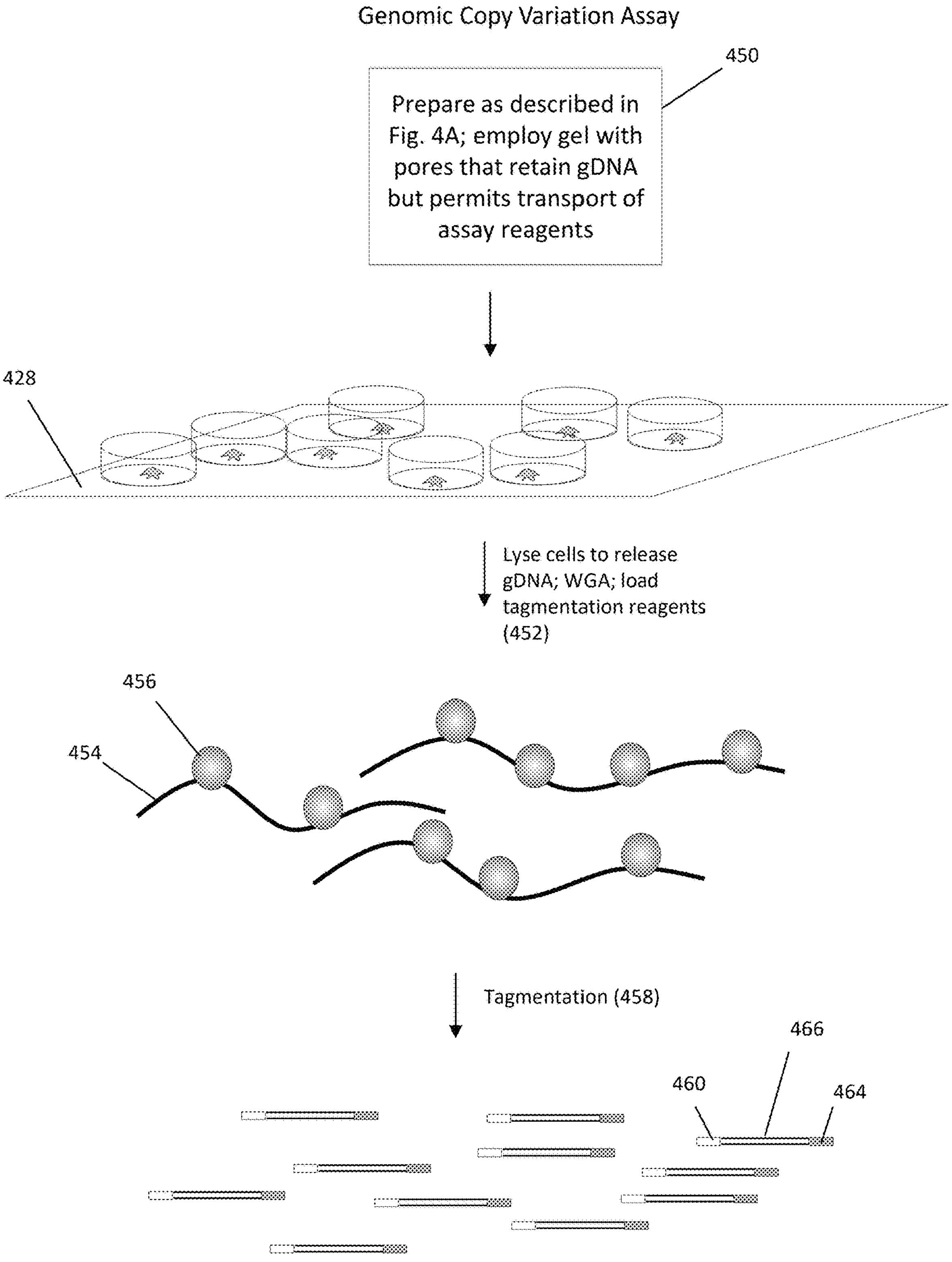
FIGS. 4G-4H illustrate an assay for determining single cell genomic copy number variation.
Figure 4H:
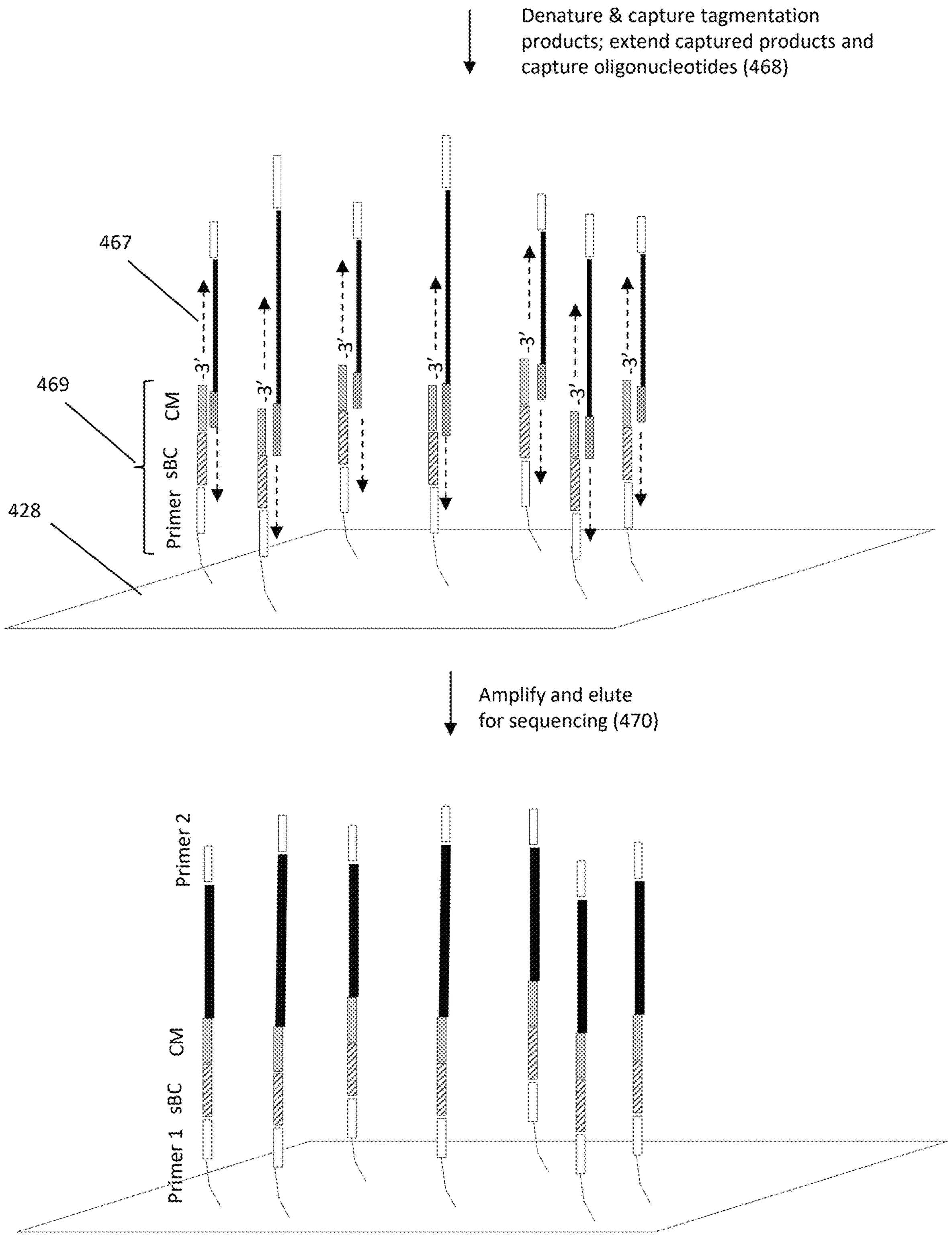

An important concern with stem cell therapy is the genetic stability of the stem cells, as they can display aneuploidy and genomic copy number variability, common features of tumorigenic cells e.g. Goldring et al, Cell Stem Cell, 8: 618-628 (2011). Single cell genomic copy number variation may be detected in populations of cells in accordance with the invention, as exemplified in FIGS. 4G-4H. In some embodiments, the method described herein comprises steps described in Example 3 of Khurana et al, U.S. patent publication US2022/0219170, which is incorporated herein by reference. As above, individual cells may be enclosed in hydrogel chambers as described in FIG. 4A (450), wherein hydrogel porosity is selected so that the walls of the chamber prevent the passage of genomic DNA, but permit the passage of reagents, such as deoxynucleoside triphosphates (dNTPs), DNA polymerase, primers, WGA reagents, tagmentation reagents, and the like, for example, gel porosity as disclosed by Spencer et al, ISME J., 10: 427-436 (2010). As shown in FIG. 4G, after cells are enclosed in hydrogel chambers, they are lysed to release genomic DNA, after which WGA reagents are loaded for increasing the amounts of gDNA in the chambers, so that after fragmentation, the fragments sequenced will provide enough coverage for the copy number variation (CNV) to be determined at an acceptable resolution. In some embodiments, a sequencing depth of 0.3× results in 3 megabase (Mb) resolution for CNV determination, e.g. Deleye et al, Scientific Reports, 7: 3422 (2017). For 0.3× coverage in human cells about 1 billion nucleotides of sequence reads are required. One of ordinary skill would recognize that the degree of amplification from WGA, surface area enclosed by chambers, and capture oligonucleotide density may be adjusted to achieve a desired CNV resolution. In some embodiments, for CNV measurement the surface area enclosed by chambers is at least $10^3$ $\mu m^2$, or at least $10^4$ $\mu m^2$, or at least $10^5$ $\mu m^2$, or at least $10^6$ $\mu m^2$, and the density of capture oligonucleotides is at least $1\times10^{12}$ capture oligonucleotides/$cm^2$. In some embodiments, WGA increases the amount of genomic DNA in each chamber by a factor of at least 100. From such genomic sequence data one can estimate genomic copy number variation by known methods, e.g. Mallory et al, Genome Biology, 21: 208 (2020); Wang et al, Briefings in Bioinformatics, 19(5); 731-736 (2018); or the like. In some embodiments, the resolution of CNV measurement is 3 megabases (Mb) or higher, or 2 Mb or higher, or 1 Mb or higher (where a higher resolution corresponds to a smaller unit of genomic length, e.g. smaller Mb value).

Returning to FIG. 4G, the amplified gDNA (454) is treated with tagmentation reagents, e.g. Tn5 transposase (456), which generates gDNA fragments (466) having upstream (460) and downstream (464) adaptors of predetermined sequences that may include amplification primer binding sites, sequencing primer binding sites, and the like.

The adaptored tagmentation fragments at then denatured so that strands may be captured by capture oligonucleotides (469) and extended (467). Capture oligonucleotide (469) comprises capture moiety ("CM"), spatial barcode ("sBC") and amplification primer ("Primer 1"). The capture oligonucleotides (469) depicted are on a subregion of surface (428) enclosed by a chamber. Of course, the entire surface (428) may have such capture oligonucleotides attached, whether or not enclosed by a chamber. A second amplification primer (Primer 2") is provided by the captured tagmentation fragment. These sequences may be amplified by a conventional PCR and the amplicon eluted (470) from the channel for sequencing. One of ordinary skill would recognize that such elution and/or amplification may be preceded by degrading the hydrogel of the chamber.

In some embodiments, the above method for genomic copy number determination for a population of cells may be implemented by (a) synthesizing one or more hydrogel chambers enclosing each of one or more cells disposed on a surface of a channel; (b) lysing the cells so that genomic DNA of each cell is released into its hydrogel chamber; (c) amplifying the genomic DNA of each cell; (d) sequencing fragments of said amplified genomic DNA; and (e) determining genomic copy number variation for each said cell from the sequences of the genomic DNA fragments. In some embodiments, the step of sequencing comprises fragmenting genomic DNA and attaching adaptors to genomic DNA fragments by tagmentation. In some embodiments, such adaptors comprise strands that are complementary to oligonucleotides of capture elements. In some embodiments, the step of sequencing comprises acquiring a sequence coverage of 0.25× of the cellular genomic DNA or greater. In some embodiments, the step of sequencing comprises acquiring a sequence coverage of the cellular genomic DNA of about 0.25× to about 100×. In some embodiments, the step of sequencing comprises acquiring a sequence coverage of the cellular genomic DNA of about 0.25× to about 0.5×, about 0.25× to about 1×, about 0.25× to about 10×, about 0.25× to about 30×, about 0.25× to about 100×, about 0.5× to about 1×, about 0.5× to about 1×, about 0.5× to about 30×, about 0.5× to about 100×, about 1× to about 10×, about 1× to about 30×, about 1× to about 100×, about 10× to about 30×, about 10× to about 100×, or about 30× to about 100×. In some embodiments, the step of sequencing comprises acquiring a sequence coverage of the cellular genomic DNA of about 0.25×, about 0.5×, about 1×, about 10×, about 30×, or about 100×. In some embodiments, the step of sequencing comprises acquiring a sequence coverage of the cellular genomic DNA of at least about 0.25×, about 0.5×, about 1×, about 10×, or about 30×. In some embodiments, the step of sequencing comprises acquiring a sequence coverage of the cellular genomic DNA of at most about 0.5×, about 1×, about 10×, about 30×, or about 100×.

In some embodiments, the genomic copy number variation is determined to a resolution of 3 megabases or higher. In some embodiments, the genomic copy number variation is determined to a resolution of about 1 megabase to about 6 megabases. In some embodiments, the genomic copy number variation is determined to a resolution of about 1 megabase to about 2 megabases, about 1 megabase to about 3 megabases, about 1 megabase to about 4 megabases, about 1 megabase to about 5 megabases, about 1 megabase to about 6 megabases, about 2 megabases to about 3 megabases, about 2 megabases to about 4 megabases, about 2 megabases to about 5 megabases, about 2 megabases to about 6 megabases, about 3 megabases to about 4 megabases, about 3 megabases to about 5 megabases, about 3 megabases to about 6 megabases, about 4 megabases to about 5 megabases, about 4 megabases to about 6 megabases, or about 5 megabases to about 6 megabases. In some embodiments, the genomic copy number variation is determined to a resolution of about 1 megabase, about 2 megabases, about 3 megabases, about 4 megabases, about 5 megabases, or about 6 megabases. In some embodiments, the genomic copy number variation is determined to a resolution of at least about 1 megabase, about 2 megabases, about 3 megabases, about 4 megabases, or about 5 megabases. In some embodiments, the genomic copy number variation is determined to a resolution of at most about 2 megabases, about 3 megabases, about 4 megabases, about 5 megabases, or about 6 megabases.

Sequencing Barcodes, Genomic Fragments and Transcriptomes

Oligonucleotide labels, barcodes, genomic fragments, messenger RNAs and similar polynucleotide targets may be sequenced by methods and systems of the invention. In some embodiments, capture elements for this purpose include oligonucleotides attached to a surface in the channel, wherein such oligonucleotides comprise a sequence segment that is complementary to that of the nucleic acids to be captured, which may be a poly A segment of mRNAs or an arbitrary sequence "handle" sequence region adjacent to a barcode or oligonucleotide label. When sequencing operations are to be performed channels are provided with such capture elements. Such capture oligonucleotides may be attached to a first surface by many chemistries known in the art, e.g. Integrated DNA Technologies brochure entitled "Strategies for attaching oligonucleotides to solid supports," (2014). The sequencing step may be performed on the surface of a channel ("in situ" sequencing) or templates may be optionally amplified, released and eluted from the channel and sequenced on an external sequencing instrument ("external" sequencing). In the latter approach, capture elements may include a spatial barcode that provides channel position information, and permits externally determined sequences to be associated with individual chambers. In some embodiments, spatial barcodes are present in sufficiently high density such that each chamber covers an area of the first surface that is uniquely associated with one or more spatial barcodes, and usually a single spatial barcode. In some embodiments, the preparation of polynucleotides for a sequencing operation takes place after the target templates (e.g. oligonucleotide label, mRNAs, genomic fragments) are released and captured by complementary sequences in the capture elements. A releasing step depends on the nature of the target templates. For example, oligonucleotide labels attached to antibodies by a disulfide linkage may be released by a reducing agent (which may be the same as a lysing reagent). mRNAs may be release by treating cells with conventional lysing agents. Releasing genomic fragments may require lysing and pre-amplification steps. Lysing conditions may vary widely and may be based on the action of heat, detergent, protease, alkaline, or combinations of such factors. The following references provide guidance for selection of lysing reagents, or lysing buffers, for single-cell lysing conditions for mRNA and/or genomic DNA: Thronhill et al, Prenatal Diagnosis, 21: 490-497 (2001); Kim et al, Fertility and Sterility, 92: 814-818 (2009); Spencer et al, ISME Journal, 10: 427-436 (2016); Tamminen et al, Frontiers Microbiol. Methods, 6: article 195 (2015); and the like. Exemplary lysis conditions include the following: 1) cells in $H_2O$ at 96° C. for 15 min, followed by 15 min at 10° C.; 2) 200 mM KOH, 50 mM dithiotheitol, heat to 65° C. for 10 min; 3) for 4 μL protease-based lysis buffer: 1 μL of 17 μM SDS combined with 3 μL of 125 μg/mL proteinase K, followed by incubation at 37° C. for 60 min, then 95° C. for 15 min (to inactivate the proteinase K); 4) for 10 μL of a detergent-based lysis buffer: 2 μL $H_2O$, 2 μL 10 mM EDTA, 2 μL 250 mM dithiothreitol, 2 μL 0.5% N-laurylsarcosin salt solution; 5) 200 mM Tris pH7.5, 20 mM EDTA, 2% sarcoyl, 6% Ficoll.

FIGS. 7A-7B illustrate exemplary capture and cDNA synthesis methods for carrying out sequencing operations. FIG. 7A illustrates one process from capturing a target template and preparing cDNAs for external sequencing. One skilled in the art would recognize that the details of the following examples of target template capture and cDNA synthesis may vary widely depending on the sequencing system employed. In some embodiments, preparation of cDNAs includes a tagmentation step. Guidance for particular embodiments may be found in Picelli et al, Genome Research, 24: 2033-2040 (2014); Bose et al, Genome Biology, 16: 120 (2015); Hashimshony et al, Genome Biology, 17: 77 (2016); Yuan et al, Scientific Reports, 6: 33883 (2016); and like references. Attached to surface (701) by their 5' ends are oligonucleotides with the following components: primer binding site P7 (for Illumina sequencers) (702), optional primer binding site R1 (for Illumina paired end sequencing), barcode oligonucleotide (706) (which may be or include a spatial barcode), optional unique molecular identifier (708), and capture oligonucleotide (710), which may be a polyT segment whenever mRNA is to be captured. Target template (712) is captured by the hybridization of poly A segment or sequence handle (714) to capture oligonucleotide (710). After capture, capture oligonucleotide (710) and poly A segment (714) are extended by a polymerase (e.g. Moloney murine leukemia virus (MMLV) reverse transcriptase) that leaves a single stranded polyC tail (716). In some embodiments, template switching oligonucleotide (718) is hybridized thereto and the polyC tail is further extended, as show in (730), e.g. Zhu et al, Biotechniques, 30: 892-897 (2001). The unattached strand is melted, the attached strand is amplified, e.g. by a PCR, and eluted for external sequencing (732). For in situ sequencing, surface (753) comprises attached P5 primers (Illumina) and capture oligonucleotides (750) that may have the same structure as for external sequencing: primer binding site P7 (for Illumina sequencers) (752), optional primer binding site R1 (for Illumina paired end sequencing), barcode oligonucleotide (756) (which may be or include a spatial barcode), optional unique molecular identifier (758), and capture oligonucleotide (760), which may be a polyT segment whenever mRNA is to be captured. Target template (762) is captured by the hybridization of poly A segment or sequence handle (764) to capture oligonucleotide (710). After capture, capture oligonucleotide (710) and poly A segment (764) are extended by a polymerase that leaves a single stranded polyC tail (766). In some embodiments, template switching oligonucleotide (768) is hybridized thereto and the polyC tail is further extended, as show in (780), after which double stranded segment (781) is ligated thereto. Segment (781) comprises complement R2' (765) to primer binding site R2 and complement P5' to primer binding site P5. The unattached strand of resulting polynucleotide (785) melted and the attached strand of (785) is bridge amplified. In some embodiments, the DNA of the resulting clusters may be sequenced using a sequencing-by-synthesis technique that generates sequences of fluorescent signals for nucleotide identification. It is understood that there are many alternatives to above process steps that may be substituted for or added to by other process steps while still being within the purview of the present invention.

In embodiments employing spatial barcodes on a surface, a wide variety of methods may be used to generated spatial barcodes including, but not limited to, the methods described in the following references which are incorporated by reference: Horgan et al, International patent publication WO2022/013094; Fan et al, U.S. patent publication US2019/0360121; Chen et al, bioRxiv (https://doi.org/10.1101/2021.01.17.427004); Cho et al, bioRxiv (https://doi.org/10.1101/2021.01.25.427807); Quan et al, Nature Biotechnology, 29(5): 449-453 (2011); Singh-Gasson et al, Nature Biotechnology, 17: 974-(1999); and the like.

In some embodiments, hydrogel chambers may be synthesized for single cells on a first surface by the following steps: (a) providing a fluidic device having (i) a channel comprising a first surface, a biological sample comprising biological cells disposed on or adjacent to the first surface, (ii) a spatial energy modulating element in optical communication with the first surface, and (iii) a detector that identifies positions of the one or more biological components in the channel based on one or more optical signals therefrom; and (b) synthesizing one or more chambers in the channel enclosing each of biological cells by projecting light into the channel with the spatial energy modulating element such that the projected light causes cross-linking of the one or more polymer precursors to form polymer matrix walls of the chambers, wherein the position of each of the synthesized chambers is determined by the position of a biological cell enclosed thereby identified by the detector. In some embodiments, the first surface comprises capture elements, such as, capture oligonucleotides covalently attached to the first surface. Exemplary capture oligonucleotides are described in FIGS. 7A-7B. Transcriptome sequencing may be carried out with the following additional steps: (i) loading into the channel a lysing reagent that ruptures cell membranes so that messenger RNA (mRNA) is released and captured by the capture elements; (ii) loading the channel with transcription reagents to copy the captured mRNAs to produce complementary DNAs thereof; and (iii) sequencing the complementary DNAs to identify said captured mRNAs. In some embodiments, wash steps may be included, for example, to remove lysing reagents prior to loading transcription reagents, or to remove transcription reagents prior to loading amplification reagents, or to remove amplification reagents prior to loading sequencing reagents, and so on. In some embodiments, reverse transcription reagents include a reverse transcriptase. In some embodiments such reverse transcriptase is an MMLV reverse transcriptase. As mentioned above, cDNA sequencing may be carried out "in situ" or external to the system. In situ sequencing may be carried out by the following additional steps: (a) amplifying the complementary DNAs, (b) sequencing the amplified complementary DNAs, for example, using a sequencing-by-synthesis technique. After sequencing, relative expression levels of the mRNAs may be determined, thereby providing a transcriptome. In some embodiments, external, or off-channel sequencing requires that the capture elements comprise spatial barcodes as described in the above example. cDNAs may be optionally amplified after which they are eluted and sequenced by an external sequencing instrument.

Hydrogel Chambers

Function. A wide variety of photosynthesizable gels may be used in connection with the invention. In some embodiments, hydrogels are used with the invention in particular because of their compatibility with living cells and the versatility of formulating gels with desired properties including, but not limited to, porosity (which in large part determines what is contained and what is passed by a gel (or polymer matrix) wall, degradability, mechanical strength, ease and speed of synthesis, and the like.

Porosity. In some embodiments, hydrogel porosity is selected to permit passage of selected reagents while at the same time preventing the passage of other reagents or objects, such as, a cell. In some embodiments, hydrogel porosity is selected to prevent the passage of biological cells but to permit the passage of reagents, including proteins, such as polymerases. In some embodiments, such reagents permeable to a polymer matrix wall comprise lysozyme, proteinase K, random hexamers, polymerases, transposases, ligases, deoxynucleotide triphosphates, buffers, cell culture media, or divalent cations. In some embodiments, the at least one polymer matrix comprises pores that are sized to allow diffusion of a reagent through the at least one polymer matrix but are too small to allow DNA or RNA for analysis to traverse the pores (having a size of greater than 100 nucleotides or basepairs, or greater than 300 nucleotides or basepairs). In some embodiments, crosslinking the polymer chains of the hydrogel structure forms a hydrogel matrix having pores (i.e., a porous hydrogel matrix). In some versions, the size of the pores in the hydrogel structures may be regulated or tuned and may be formulated to encapsulate sufficiently large genetic material, such as cells or nucleic acids (e.g., of greater than about 300 base pairs), but to allow smaller materials, such as reagents, or smaller sized nucleic acids (e.g., of less than about 50 base pairs), such as primers, to pass through the pores, thereby passing in and out of the hydrogel structures. In some embodiments, the hydrogels can have any pore size having a diameter sufficient to allow diffusion of the above-listed reagents through the structure while retaining the nucleic acid molecules greater than 500 nucleotides or basepairs in length. In some embodiments, the hydrogel structure can be swollen when the hydrogel is hydrated. The sizes of the pores can then change depending on the water content in the hydrogel of the hydrogel structure. In some embodiments, the pores have a diameter of from about 10 nm to about 100 nm. In some embodiments, the pore size of the hydrogel structures is tuned by varying the ratio of the concentrations of polymer precursors to the concentration of crosslinkers, varying pH, salt concentrations, temperature, light intensity, and the like, by routine experimentation. In some embodiments, the average diameter of pores of a polymer matrix wall prevent passage of molecules having a molecular weight of 25 kiloDaltons (kDa) or greater; or having a molecular weight of 50 kDa or greater; or having a molecular weight of 75 kDa or greater; or having a molecular weight of 100 kDa or greater; or having a molecular weight of 150 kDa or greater.

In some embodiments, DNA or RNA retained have lengths that are sequenceable using conventional sequencing-by-synthesis techniques. For example, such DNA or RNA comprise at least 50 nucleotides, or in some embodiments, at least 100 nucleotides. In some embodiments, the pores may have an average diameter from 5 nm to 100 nm. In some embodiments, the pores may have an average diameter from 5 nm to 10 nm, 10 nm to 20 nm, 20 nm to 30 nm, 30 nm to 40 nm, 50 nm to 60 nm, 60 nm to 70 nm, 70 nm to 80 nm, 80 nm to 90 nm, 90 nm to 100 nm. In some embodiments, the pores may have an average diameter larger than 100 nm. In some embodiments, the pores may have an average diameter smaller than 5 nm. The reagent may comprise an enzyme or a primer having a size of less than 50 base pairs (bp). A primer may comprise a single-stranded DNA (ssDNA). In some embodiments, a primer may have a size from 5 bp to 50 bp. In some embodiments, a primer may have a size from 5 bp to 10 bp, 10 bp to 20 bp, from 20 bp to 30 bp, 30 bp to 40 bp, or 40 bp to 50 bp. In some embodiments, a primer may have a size of more than 50 bp. In certain cases, a primer may have a size of less than 5 bp. In some embodiments, the pores may have a diameter from 5 nm to 100 nm. In some embodiments, the pores may have a diameter from 5 nm to 10 nm, 10 nm to 20 nm, 20 nm to 30 nm, 30 nm to 40 nm, 50 nm to 60 nm, 60 nm to 70 nm, 70 nm to 80 nm, 80 nm to 90 nm, 90 nm to 100 nm. In some embodiments, the pores may have a diameter larger than 100 nm. In some embodiments, the pores may have an average diameter smaller than 5 nm. The polymer matrix may have a pore size of about 5 nanometers (nm) to about 100 nm. The polymer matrix may have a pore size of about 5 nm to about 10 nm, about 5 nm to about 20 nm, about 5 nm to about 30 nm, about 5 nm to about 40 nm, about 5 nm to about 50 nm, about 5 nm to about 60 nm, about 5 nm to about 70 nm, about 5 nm to about 80 nm, about 5 nm to about 90 nm, about 5 nm to about 100 nm, about 5 nm to about 110 nm, about 10 nm to about 20 nm, about 10 nm to about 30 nm, about 10 nm to about 40 nm, about 10 nm to about 50 nm, about 10 nm to about 60 nm, about 10 nm to about 70 nm, about 10 nm to about 80 nm, about 10 nm to about 90 nm, about 10 nm to about 100 nm, about 10 nm to about 110 nm, about 20 nm to about 30 nm, about 20 nm to about 40 nm, about 20 nm to about 50 nm, about 20 nm to about 60 nm, about 20 nm to about 70 nm, about 20 nm to about 80 nm, about 20 nm to about 90 nm, about 20 nm to about 100 nm, about 20 nm to about 110 nm, about 30 nm to about 40 nm, about 30 nm to about 50 nm, about 30 nm to about 60 nm, about 30 nm to about 70 nm, about 30 nm to about 80 nm, about 30 nm to about 90 nm, about 30 nm to about 100 nm, about 30 nm to about 110 nm, about 40 nm to about 50 nm, about 40 nm to about 60 nm, about 40 nm to about 70 nm, about 40 nm to about 80 nm, about 40 nm to about 90 nm, about 40 nm to about 100 nm, about 40 nm to about 110 nm, about 50 nm to about 60 nm, about 50 nm to about 70 nm, about 50 nm to about 80 nm, about 50 nm to about 90 nm, about 50 nm to about 100 nm, about 50 nm to about 110 nm, about 60 nm to about 70 nm, about 60 nm to about 80 nm, about 60 nm to about 90 nm, about 60 nm to about 100 nm, about 60 nm to about 110 nm, about 70 nm to about 80 nm, about 70 nm to about 90 nm, about 70 nm to about 100 nm, about 70 nm to about 110 nm, about 80 nm to about 90 nm, about 80 nm to about 100 nm, about 80 nm to about 110 nm, about 90 nm to about 100 nm, about 90 nm to about 110 nm, or about 100 nm to about 110 nm. The polymer matrix may have a pore size of about 5 nm, about 10 nm, about 20 nm, about 30 nm, about 40 nm, about 50 nm, about 60 nm, about 70 nm, about 80 nm, about 90 nm, about 100 nm, or about 110 nm. The polymer matrix may have a pore size of at least about 5 nm, about 10 nm, about 20 nm, about 30 nm, about 40 nm, about 50 nm, about 60 nm, about 70 nm, about 80 nm, about 90 nm, about 100 nm, or less. The polymer matrix may have a pore size of at most about 10 nm, about 20 nm, about 30 nm, about 40 nm, about 50 nm, about 60 nm, about 70 nm, about 80 nm, about 90 nm, about 100 nm, about 110 nm, or more.

Modulation of Porosity. The pore size in the polymer matrix may be modulated using a chemical reagent, or by applying heat, electrical field, light, or another suitable stimulus. In other words, the polymer matrix may comprise tunable properties (e.g., the pore size) In some cases, the polymer matrix may comprise a thermoresponsive or temperature-responsive polymer. A thermoresponsive polymer (e.g., poly(N-isopropylacrylamide) (NIPAAM)) may phase separate from a solution upon heating or upon cooling (e.g., polymer showing lower critical solution temperature (LCST) or upper critical solution temperature (UCST). The polymer matrix may comprise polymer which may collapse at high temperature in order to, for example, control the pore size of the hydrogel or polymer matrix. Non-limiting examples of thermoresponsive polymers that may be used to form hydrogel/polymer matrix with tunable properties may include Poly(N-vinyl caprolactam), Poly(N-ethyl oxazoline), Poly(methyl vinyl ether), Poly(acrylic acid-coacrylamide), or a combination thereof. A change in temperature may enlarge or contract average pore size in the polymer matrix to allow selected molecules, such as a nucleic acid molecule, a protein, or any biomolecule or molecule smaller than the adjusted pore size to be released from a hydrogel chamber.

Size and Shape of Hydrogel Chambers. In some embodiments, a polymer matrix wall of a chamber inhibits passage of a predetermined component, such as a mammalian cell, genomic DNA, larger polynucleotides (e.g. mRNA greater than 200 ribonucleotides, or greater than 300 ribonucleotides, or 500 ribonucleotides), or the like. In some embodiments, a polymer matrix wall extends from the first surface to a second surface (parallel to the first surface) to form a chamber within a channel. In some embodiments, a chamber has polymer matrix walls and an interior. In some embodiments, the interior of a chamber is sized for enclosing a cell. For example, such chamber may comprise a cylindrical shell or a polygon shell, comprising an inner space, or interior and a polymer matrix wall. In some embodiments, such chambers have annular-like cross-sections. As used herein, the term "annular-like cross-section" means a cross-section topologically equivalent to an annulus. In some embodiments, the inner space, or interior, of a chamber has an inner diameter from 1 μm to 500 μm and a volume in the range of from 1 pico liter to 200 nano liters, or from 100 pico liters to 100 nano liters, or from 100 picoliters to 10 nano liters. In some embodiments, the polymer matrix wall has a thickness of at least 1 μm (micrometer). In some embodiments, the height of a chamber with an annular-like cross section have a value in the range of from 10 μm to 500 μm, or in the range of from 50 μm to 250 μm. In some embodiments, a polymer matrix wall having an annular-like cross-section has an aspect ratio (i.e., height/width) of 1 or less. In some embodiments, aspect ratio and polymer matrix wall thickness are selected to maximize chamber stability against forces, such as reagent flow through the channel, washings, and the like. In some embodiments, the at least one polymer matrix wall is a hydrogel wall. In some embodiments, the at least one polymer matrix is degradable. In some embodiments, the degradation of the at least one polymer matrix is "on demand." In some embodiments, chambers in a channel are non-contiguous. In some embodiments, chambers in a channel may be contiguous with adjacent chambers. In some embodiments, chambers may share polymer matrix walls with one another. In some embodiments, chambers may be synthesized with slits or other orifices large enough to permit passage of certain components, e.g. beads, but small enough to prevent passage of other components, e.g. cells.

Hydrogel Compositions. In some embodiments, a channel of a fluidic device of a system of the invention comprises one or more polymer precursors for forming chambers. In some embodiments, the one or more polymer precursors comprise hydrogel precursors. Such precursors may be selected from a wide variety of compounds including, but not limited to, polyethylene glycol (PEG)-thiol, PEG-acrylate, acrylamide, N,N'-bis(acryloyl) cystamine, PEG, polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly (lactic acid) (PLA), poly(lactic-co-glycolic acid) (PLGA), polycaprolactone (PCL), poly(vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, collagen, bisacrylamide, diacrylate, diallylamine, triallylamine, divinyl sulfone, diethyleneglycol diallyl ether, ethyleneglycol diacrylate, polymethyleneglycol diacrylate, polyethyleneglycol diacrylate, trimethylopropoane trimethacrylate, ethoxylated trimethylol triacrylate, or ethoxylated pentaerythritol tetraacrylate, or combinations or mixtures thereof. In some embodiments, the hydrogel comprises an enzymatically degradable hydrogel, PEGthiol/PEG-acrylate, acrylamide/N,N'-bis(acryloyl) cystamine (BACy), or PEG/PPO. In some embodiments, the following precursors and crosslinker may be used to form chambers with degradable polymer matrix (hydrogel) walls. Polymer precursors may be formed by using any hydrogel precursor and crosslinkers of Table 2A (columns 1 and 3, respectively). The resulting polymer matrices may be degraded with the indicated degradation agents in Table 2A (column 4).

TABLE 2A

| Precursors | Hydrogels | Crosslinkers | Degradation Agents |
|---|---|---|---|
| Acrylamide | Poly-acrylamide | Bis-acryloyl cystamine (structure 1) | DTT/TCEP/THP |
| PEG-based acryloyl | PEG | Bis(2-methacryloly)oxyethyl disulfide (structure 2) | DTT/TCEP/THP |
| Dextran-based acryloyl | Dextran | N,N'-(1,2-Dihydroxylethylene)bis-acrylamide( structure 3) | NaIO4 |
| Polysaccharide-base acryloyl | Poly-saccharide | Structure 4 | NaOH, ethanolamine DTT/TCEP/THP |
| Gelatin-base acryloyl | Gelatin | Structure 5 | NaOH, ethanolamine, nucleophilic bases |
| | | Structure 6 | NaOH, alkali, organic bases |
| | | Structure 7 | Acid |

TABLE 2B

| Structure Number | Formula |
|---|---|
| 1 | 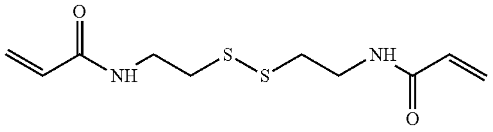 [SMILES: C=CC(=O)NCCSSCCNC(=O)C=C] |
| 2 | 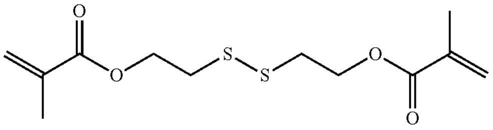 [SMILES: C=C(C)C(=O)OCCSSCCOC(=O)C(=C)C] |
| 3 | 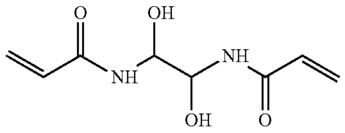 |
| 4 | 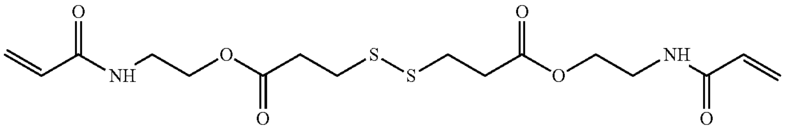 [SMILES: C=CC(=O)NCCOC(=O)CCSSCCC(=O)OCCNC(=O)C=C] |
| 5 | 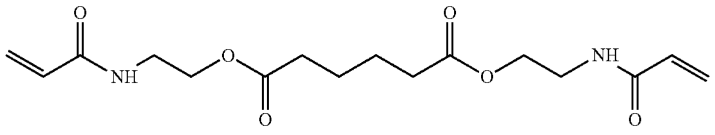 [SMILES: C=CC(=O)NCCOC(=O)CCCCC(=O)OCCNC(=O)C=C] |
| 6 | 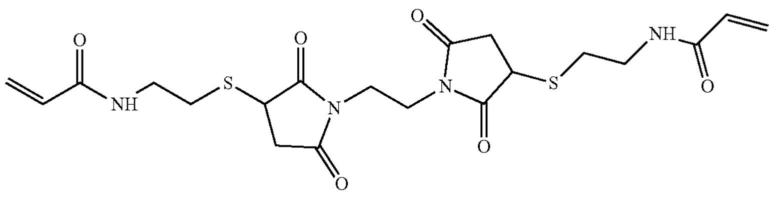 [SMILES: C=CC(=O)NCCSC1CC(=O)N(CCN2C(=O)CC(SCCNC(=O)C=C)C2=O)C1=O] |

TABLE 2B-continued

| Structure Number | Formula |
| --- | --- |
| 7 | 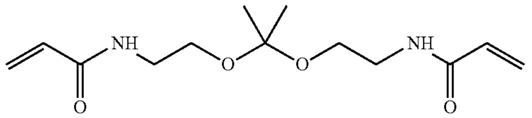 [SMILES: C=CC(=O)NCCOC(C)(C)OCCNC(=O)C=C] |

Hydrogel Degradation. In some embodiments, hydrogel chambers of the invention are degradable or depolymerizable either generally within a channel or "on demand" within a channel. Hydrogel chambers that are generally degradable are degraded by treatment with a degradation agent, or equivalently, a depolymerization agent that is exposed to all chambers within channel. Exemplary depolymerization agents include, but are not limited to, heat, light, and/or chemical depolymerization reagents (also sometimes referred to a cleaving reagents or degradation reagents). In some embodiments, on demand degradation may be implemented using polymer precursors that permit photo-crosslinking and photo-degradation, for example, using different wavelengths for crosslinking and for degradation. For example, Eosin Y may be used for radical polymerization at defined regions using 500 nm wavelength, after which illumination at 380 nm can be used to cleave the cross linker. In other embodiments, photo-caged hydrogel cleaving reagents may be included in the formation of polymer matrix walls. For example, acid labile crosslinkers (such as esters, or the like) can be used to create the hydrogel and then UV light can be used to generate local acidic conditions which, in turn, degrades the hydrogel. In some embodiments, the at least one polymer matrix is degradable by at least one of: (i) contacting the at least one polymer matrix with a cleaving reagent; (ii) heating the at least one polymer matrix to at least 90° C.; or (iii) exposing the at least one polymer matrix to a wavelength of light that cleaves a photo-cleavable cross linker that cross links the polymer of the at least one polymer matrix. In some embodiments, the at least one polymer matrix comprises a hydrogel. In some embodiments, the cleaving reagent degrades the hydrogel. In some embodiments, the cleaving reagent comprises a reducing agent, an oxidative agent, an enzyme, a pH based cleaving reagent, or a combination thereof. In some embodiments, the cleaving reagent comprises dithiothreitol (DTT), tris(2-carboxyethyl) phosphine (TCEP), tris(3-hydroxypropyl)phosphine (THP), or a combination thereof. In some embodiments, the surface of the polymer matrix or hydro gel may be functionalized by coupling a functional group to the polymer matrix or hydrogel. Some nonlimiting examples of functional group may include a capture reagent (e.g., pyridinecarboxaldehyde (PCA)), an acrylamide, an agarose, a biotin, a streptavidin, a strep-tag II, a linker, a functional group comprising an aldehyde, a phosphate, a silicate, an ester, an acid, an amide, an aldehyde dithiolane, PEG, a thiol, an alkene, an alkyne, an azide, or a combination thereof. In some cases, the functionalized polymer matrix may be used to capture biomolecules inside a polymer matrix compartment formed adjacent to (e.g., around or on) the biological component. The biomolecule may be produced by the biological component (e.g., secretome from a cell). The functionalized surface of the polymer matrix inside the compartment may be used to capture reagents or molecules from outside the compartment. The functionalized surface may increase surface area covered by a reagent, a molecular sensor, or any molecule of interest (e.g., an antibody).

Partial Degradation. In some embodiments, existing polymer matrix walls may be partially degraded, e.g. to change porosity. In some embodiments, polymer precursors may include degradable beads that form part of, and are embedded in, the polymer matrix walls when synthesized, after which either on-demand or generally, may be degraded, thereby creating an increase in porosity.

Photosynthesis. In some embodiments, the generation of a polymer matrix within said fluidic device comprises exposing the one or more polymer precursors to an energy source. In some embodiments, the energy source is a light generating device. In some embodiments, the light generating device generates light at 350 nm to 800 nm. In some embodiments, the light generating device generates light at 350 nm to 600 nm. In some embodiments, the light generating device generates light at 350 nm to 450 nm. In some embodiments, the light generating device generates UV light. In some embodiments, the generation of a polymer matrix within said fluidic device is performed using a spatial light modulator (SLM) (i.e. a spatial energy modulation element that is capable of generating desired light intensity pattern spatially). In some embodiments, the SLM is a digital micromirror device (DMD). In some embodiments, the SLM is a laser beam steered using a galvanometer. In some embodiments, the SLM is liquid-crystal based.

Systems and Instrumentation

In some embodiments, systems of the invention comprise (a) a channel comprising a first surface, a plurality of cells disposed on the first surface, and one or more polymer precursors; (b) a spatial energy modulating element in optical communication with the first surface; (c) a detector in optical communication with the first surface and in operable association with the spatial energy modulating element, the detector detecting each of the plurality of cells and determining a position thereof on the first surface; and (d) a plurality of gel chambers each gel chamber enclosing a single cell of the plurality of cells wherein the gel chambers are synthesized by projecting light into the channel with the spatial energy modulating element such that the projected light causes cross-linking of the one or more polymer precursors to form polymer matrix walls of the chambers, wherein the positions of the synthesized chambers are determined by the positions of cells enclosed thereby identified by the detector. It is understood that the term "detector" as used herein may include, but not be limited by, a microscope element that collects and optionally magnifies an image of a portion of a channel and an image analysis element that comprises software for identifying cells, cellular features, chambers, and other objects, for storing such information as well as associated position information. A computer element uses such information generated by a detector together with user input to generate commands to other elements, such as, the spatial energy modulating element to carry out a variety of functions including, but not limited to, synthesizing chambers, "on-demand" degrading of chambers, photo-lysing cells, and the like. Exemplary configurations of such embodiments are illustrated in FIGS. 5A-5B which are described above. In some embodiments, a channel of a fluidic device further comprises a second surface wherein said first surface and the second surface are disposed opposite one another across the channel, and wherein the polymer matrix walls of the chambers extend from the first surface to the second surface to form chambers each having an interior. In some embodiments, chambers in a channel each enclose a single cell. In some embodiments both the first wall and the second wall are made of optically transmissive materials, such as, glass, plastic, or the like, and are positioned so that the first surface and second surface are substantially parallel to one another. the perpendicular distance between a first surface and a second surface may be in the range of from 10 μm to 500 μm, or in the range of from 50 μm to 250 μm. In some embodiments, the perpendicular distance between a first surface and a second surface may be in the range of from twice the average size of the cells to be analyzed to five times the average size of the cells to be analyzed.

In other embodiments, the first surface may comprise capture elements for capturing cells at predetermined locations. For example, capture elements may include, but are not limited to, capture antibodies specific for all or a subpopulation of cells. Capture elements may also include, but not be limited to, non-specific capture materials, such as, polylysine, fibronectin, treated plastics (e.g. Maxysorb™ plastic, ThermoFisher), and the like. In some embodiments, such cellular capture moieties (for example, antibodies) may be restricted to spots or reaction sites arrayed in a regular pattern on the first surface; thus, cells captured at such reaction sites may be disposed on the first surface in a regular pattern that may be more efficiently than a random disposition for chamber synthesis and/or optical signal detection. Guidance for providing surfaces with cellular capture antibodies may be found in the following references: Zhu et al, Analytica Chemica Acta, 608: 186-196 (2008); Sekine et al, J. Immunol. Methods, 313 (1-2): 96-109 (2006); and the like. In some embodiments, such reaction sites or spots have diameters in the range of from 5-500 μm or in the range of from 10-1000 μm. In some embodiments, such spots or reaction sites are arranged in a rectilinear array, or are arranged in a hexagonal array. In some embodiments, such arrays of such spots or reaction sites have a density in the range of from 10 to 2500 sites/$mm^2$, or from 10 to 1000 sites/$mm^2$, or from 10 to 500 sites/$mm^2$, or from 10 to 100 sites/$mm^2$.

In some embodiments, cells may be disposed randomly on the first surface. In some embodiments, cells are disposed randomly on the first surface in a Poisson distribution. In some embodiments, in such Poisson distribution cells have a nearest neighbor distance equal to or greater 10 μm, equal to or greater 20 μm, equal to or greater 30 μm, equal to or greater 40 μm, equal to or greater 50 μm, or equal to or greater 100 μm. In some embodiments, a subset of such Poisson distributed cells are each enclosed by an annular-like shaped chamber having a diameter in the range of from 10-500 μm. In some embodiments, cells are disposed randomly on the first surface in a Poisson distribution having a density in the range of from 10 to 2500 cells/$mm^2$, or from 10 to 1000 cells/$mm^2$, or from 10 to 500 cells/$mm^2$, or from 10 to 100 cells/$mm^2$.

In some embodiments, a plurality of channels may be arranged together in a flow channel as illustrated in FIGS. 6A-6B. In some embodiments, the plurality of channels may be in the range of from 2 to 12, or from 2 to 8, or from 2 to 6, or in the range of from 2 to 4. Exemplary flow cell (600) is shown in a cross-sectional view and a top view. Flow cell (600) has bottom, or first, wall (606) with first surface (605); top, or second, wall (602) with second surface (601); and sandwiched sealingly therebetween spacer (604) whose longitudinal holes form channels 1-6, one of which is indicated by (608) in the cross-sectional view, and by (612) in the top view. In some embodiments, spacer (604) may have a thickness in the range of from 10 μm to 500 μm, or in the range of from 50 μm to 250 μm, which determines the interior height of the channels. Top wall (602) comprises inlets (614) and outlets (616) for either separately or jointly loading and removing reagents and cells from channels 1-6. In some embodiments, at least one of walls (602) and (606) are made of light transmissive materials, such as glass, plastic, or the like. Flow cell (600) may be operationally associated with a fluidic device that delivers reagents and cells to any of channels 1-6 under programmed control. Guidance for particular designs, including fluid handling and valving for such fluidic systems may be found in U.S. Pat. Nos. 8,921,073; 8,173,080; 8,900,828; and the like, which are incorporated herein by reference. FIG. 6B illustrates channels of flow cell (600) with random distributions (not to scale) of hydrogel chambers with annulus-like cross-sections, such as (620), on their first surfaces.

As noted above, any of first surfaces, second surfaces or polymer matrix wall of chambers may comprise capture elements and other functional groups for carrying out a variety of operations including, but not limited to, capturing cells, capturing constituents of cells (such as, mRNA, secreted proteins, intracellular proteins, or genomic sequences), capturing constituents of analytical reagents (such as, oligonucleotide labels from antibodies), and the like. Derivatizing surfaces for such purposes is well-known to those skilled in the art, as evidenced by the following exemplary references: Zhu et al (cited above); Sekine et al (cited above); Integrated DNA Technologies brochure (cited above); Hermanson (cited above); and the like.

As noted above, in some embodiments, a fluidic device of the method comprises or is operationally associated with a detector that either may share an optical path of the spatial energy modulating element or may be disposed adjacent to the second wall or opposite the first wall from the spatial energy modulating element in embodiments, such as wells, that have only a first wall and first surface. The detector is positioned so that it is capable of detecting optical signals from or adjacent to cells in the channel, for example, distributed over the first surface in chambers. In some embodiments, the first and second walls each comprise optically transmissive material, for example, so that a spatial energy modulating element may project light energy to the interior of the channel, and so that a detector may detect optical signals, such as fluorescent emissions or reflected light from biological components. In some embodiments, the projected energy from the spatial energy modulating element is a light energy from a light beam. In some embodiments, the light beam projected by the spatial energy modulating element may have a complex cross-section that permits (in various embodiments) the simultaneous synthesis of a plurality of chambers. Optically transmissive materials include, but are not limited to, glass, quartz, plastic, and like materials. In some embodiments, the step of synthesizing chambers includes positioning the chambers so that they encapsulate the one or more biological components based on the optical signals detected by the detector. That is, in some embodiments, the detector is operationally associated with the spatial energy modulating element to selectively project one or more light beams to locations where detected optical signals indicate the presence of cell of interest. In such embodiments, the detector and spatial energy modulating element are operationally associated so that the spatial energy modulating element is configured to generate an energy beam having predetermined beam characteristics. For example, one such characteristic may be a beam cross-section which results in the biological components of interest being enclosed by annular-like shaped chambers. In such operational association, optical signals detected by the detector may include, but is not limited to, morphology of biological components, for example, cell morphology; cell motility; interaction of one cell type with another cell type, such as binding of one cell type to another cell type; a presence, absence or quantity of a label on the cell, or the like.

Spatial energy modulating elements using light energy for polymerization may comprise physical photomasks or virtual photomask, such as, a digital micromirror device (DMD). The following references, which are hereby incorporated by reference, provide guidance in selecting and operating a DMD for photopolymering gels: Chung et al, U.S. Pat. No. 10,464,307; Hribar et al, U.S. Pat. No. 10,351,819; Das et al, U.S. Pat. No. 9,561,622; Huang et al, Biomicrofluidics, 5: 034109 (2011); and the like.

While the present invention has been described with reference to several particular example embodiments, those skilled in the art will recognize that many changes may be made thereto without departing from the spirit and scope of the present invention. The present invention is applicable to a variety of sensor implementations and other subject matter, in addition to those discussed above.

Definitions

Unless otherwise specifically defined herein, terms and symbols of nucleic acid chemistry, biochemistry, genetics, and molecular biology used herein follow those of standard treatises and texts in the field, e.g. Kornberg and Baker, DNA Replication, Second Edition (W. H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Abbas et al, Cellular and Molecular Immunology, $6^{th}$ edition (Saunders, 2007).

"Chimeric antigen receptor T cell" (CAR-T cell) means a T cell engineered to express an antigen-specific receptor formed by fusing antigen-binding components with transmembrane and signaling components, which is capable of eliciting a cytotoxic T cell response whenever the antigen-specific component binds to its target. Exemplary references teaching the manufacture and application of CAR-T cells include the following references that are incorporated herein by reference: U.S. Pat. No. 8,822,647; and U.S. patent publications 2014/0134142; 2014/0314795; 2012/0148552; 2013/0288368; and the like.

"Cleavable linkage" or "cleavable nucleotide" means any of wide variety of cleavable linkages, or more particularly, cleavable nucleotides, may be used with embodiments of the invention. As used herein, the term "cleavable site" refers to a nucleotide or backbone linkage of a single stranded nucleic acid sequence that can be excised or cleaved under predetermined conditions, thereby separating the single stranded nucleic acid sequence into two parts. In some embodiments, a step of cleaving a cleavable nucleotide or a cleavable linkage leaves a free 3'-hydroxyl on a cleaved strand, thereby, for example permitting the cleaved strand to be extended by a polymerase. Cleaving steps may be carried out chemically, thermally, enzymatically or by light-based cleavage. Sometimes the term "releasing" may be used in reference to cleaving an oligonucleotide label, for example, by a releasing reagent or agent, which may be one or more of those listed above. In some embodiments, cleavable nucleotides may be nucleotide analogs such as deoxyuridine or 8-oxo-deoxyguanosine that are recognized by specific glycosylases (e.g. uracil deoxyglycosylase followed by endonuclease VIII, and 8-oxoguanine DNA glycosylase, respectively). In some embodiments, cleavage by glycosylases and/or endonucleases may require a double stranded DNA substrate. Methods synthesizing and cleaving nucleic acids containing chemically cleavable, thermally cleavable, and photo-labile groups are described for example, in U.S. Pat. No. 5,700,642, which is incorporated herein by reference. Further cleavable linkages are disclosed in the following references: Pon, R., Methods Mol. Biol. 20:465-496 (1993); Verma et al., Ann. Rev. Biochem. 67:99-134 (1998); U.S. Pat. Nos. 5,739,386, 5,700,642 and 5,830,655; and U.S. Patent Publication Nos. 2003/0186226 and 2004/0106728, Urdea et al, U.S. Pat. No. 5,367,066, which are incorporated herein by reference. Synthesis and cleavage conditions of chemically cleavable oligonucleotides are described in U.S. Pat. Nos. 5,700,642 and 5,830,655. Phosphorothioate internucleotide linkage may be selectively cleaved under mild oxidative conditions. Selective cleavage of the phosphoramidate bond may be carried out under mild acid conditions, such as 80% acetic acid. Selective cleavage of ribose may be carried out by treatment with dilute ammonium hydroxide. In another embodiment, a cleavable linking moiety may be an amino linker. The resulting oligonucleotides bound to the linker via a phosphoramidite linkage may be cleaved with 80% acetic acid yielding a 3'-phosphorylated oligonucleotide, which may (if desired) be removed by a phosphatase. In some embodiments, the cleavable linking moiety may be a photocleavable linker, such as an ortho-nitrobenzyl photocleavable linker. Synthesis and cleavage conditions of photolabile oligonucleotides on solid supports are described, for example, in Venkatesan et al., J. Org. Chem. 61:525-529 (1996), Kahl et al., J. Org. Chem. 64:507-510 (1999), Kahl et al., J. Org. Chem. 63:4870-4871 (1998), Greenberg et al., J. Org. Chem. 59:746-753 (1994), Holmes et al., J. Org. Chem. 62:2370-2380 (1997), and U.S. Pat. No. 5,739,386. Ortho-nitrobenzyl-based linkers, such as hydroxymethyl, hydroxyethyl, and Fmoc-aminoethyl carboxylic acid linkers, may also be obtained commercially. In some embodiments, ribonucleotides may be employed as cleavable nucleotides, wherein a cleavage step may be implemented using a ribonuclease, such as RNase H. In other embodiments, cleavage steps may be carried out by treatment with a nickase.

"Hydrogel" means a gel comprising a crosslinked hydrophilic polymer network with the ability to absorb and retain large amounts of water (for example, 60 to 90 percent water, or 70 to 80 percent) without dissolution due to the establishment of physical or chemical bonds between the polymeric chains, which may be covalent, ionic or hydrogen bonds. Hydrogels exhibit high permeability to the oxygen and nutrients, making them attractive materials for cell encapsulation and culturing applications. Hydrogels may comprise natural or synthetic polymers and may be reversible (i.e. degradable or depolymerizable) or irreversible. Exemplary synthetic hydrogel polymers include polyethylene glycol (PEG), poly(2-hydroxyethyl methacrylate) and poly(vinyl alcohol). Exemplary natural hydrogel polymers include alginate, hyaluronic acid and collagen. The following reference describe hydrogels and their biomedical uses: Drury et al, Biomaterials, 24: 4337-4351 (2003); Garagorri et al, Acta Biomatter, 4(5): 1139-1147 (2008); Caliari et al, Nature Methods, 13(5): 405-414 (2016); Bowman et al, U.S. Pat. No. 9,631,092; Koh et al, Langmuir, 18(7): 2459-2462 (2002).

"On demand" means an operation may be directed to individual, discrete, selected locations (e.g. a spatial location of polymer precursor solution; or a selected polymer matrix chamber). Such selection may be based on manual observation of optical signals or data collected by a detector, or such selection may be based on a computer algorithm operating on optical signals or data collected by a detector. Manual observation of optical signals or data collected by a detector can include either real-time detection or detection at a time period prior to modulating a unit of energy to polymerize polymer precursors or degrading a chamber. For example, a subset of chambers (all formed with photo-degradable polymer matrix walls) may be pre-selected for releasing and removing their contents based on position information and the values of optical signals from an analytical assay carried out in the chambers. The pre-selected chambers may be photo-degraded by selectively projecting a light beam of appropriate wavelength characteristics (for example, with the spatial energy modulating element) to degrade the polymer matrix walls of the pre-selected chambers. In another example, a plurality of chambers may be observed in real-time (e.g. via fluorescent microscopy) for detection of an analyte of interest and one or more chambers of the plurality of chambers is selected, in real-time, upon detection of the analyte of interest, for degradation.

"Physical photomask" generally refers to a physical structure having a plurality of apertures or holes through which light may be projected. Physical photomasks can be used to create hydrogel matrices as described herein by causing the polymer precursor solution to polymerize and forming three-dimensional structures that correspond to the pattern on the photomask. A physical photomask can be patterned with a specific layout or geometric pattern. A physical photomask may be adhered to the upper surface of a flow cell.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature>90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 nL, to a few hundred μL, e.g. 200 μL. "Reverse transcription PCR," or "RT-PCR," means a PCR that is preceded by a reverse transcription reaction that converts a target RNA to a complementary single stranded DNA, which is then amplified, e.g. Tecott et al, U.S. Pat. No. 5,168,038, which patent is incorporated herein by reference. "Real-time PCR" or "quantitative PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("taqman"); Wittwer et al, U.S. Pat. Nos. 6,174,670 and 6,569,627 (intercalating dyes); Tyagi et al, U.S. Pat. No. 5,925,517 (molecular beacons); which patents are incorporated herein by reference. Detection chemistries for real-time PCR are reviewed in Mackay et al, Nucleic Acids Research, 30: 1292-1305 (2002), which is also incorporated herein by reference.

"Polymer matrix" generally refers to a phase material (e.g. continuous phase material) that comprises at least one polymer. In some embodiments, the polymer matrix refers to the at least one polymer as well as the interstitial space not occupied by the polymer. A polymer matrix may be composed of one or more types of polymers. A polymer matrix may include linear, branched, and crosslinked polymer units. A polymer matrix may also contain non-polymeric species intercalated within its interstitial spaces not occupied by polymer chains. The intercalated species may be solid, liquid, or gaseous species. For example, the term "polymer matrix" may encompass desiccated hydrogels, hydrated hydrogels, and hydrogels containing glass fibers. A polymer matrix may comprise a polymer precursor, which generally refers to one or more molecules that upon activation can trigger or initiate a polymeric reaction. A polymer precursor can be activated by electrochemical energy, photochemical energy, a photon, magnetic energy, or any other suitable energy. As used herein, the term "polymer precursor" includes monomers (that are polymerized to produce a polymer matrix) and crosslinking compounds, which may include photo-initiators, other compounds necessary or useful for generating polymer matrices, especially polymer matrices that are hydrogels.

"Transfection" and/or "transformation" and/or "transduction" are used synonymously herein mean the transfer of exogenous genetic material to a target mammalian cell. Such transfer may be result in temporary or transient expression of a transgene or temporary or transient transcription of an RNA, for example, because of exhaustion of genetic material, loss or degradation of genetic material, lack of replication of genetic material, or the like. In some embodiments, "transfection" means "stable transfection" as the latter term is commonly used, e.g. Kim et al, Anal. Bioanal. Chem., 379: 3173-3178 (2010). Exogenous genetic material may include plasmids, viral vectors, transgenes, transposons, or the like. "Stable" as used herein means that the exogenous genetic material persists through multiple cell divisions or for the life of the cellular host. The exogenous genetic material may be integrated into the genome of a target mammalian cell or it may comprise episomal DNA, such as a plasmid.

What is claimed is:

1. A method, comprising:

(a) introducing a first cell into a fluidic device;

(b) introducing a second cell into the fluidic device;

(c) introducing a polymer precursor into the fluidic device;

(d) using a virtual photomask to selectively apply light to the fluidic device to polymerize the polymer precursor, thereby selectively enclosing the first cell and the second cell in the fluidic device; and (e) measuring cytotoxicity of the first cell against the second cell.

2. The method of claim 1, wherein in (b), a plurality of second cells are introduced into the fluidic device.

3. The method of claim 2, wherein the measuring the cytotoxicity comprises counting dead cells, viable cells, or a combination thereof, from among the plurality of second cells.

4. The method of claim 3, wherein the counting comprises staining the dead cells with a vital dye.

5. The method of claim 1, wherein in (d), the first cell and the second cell are selectively enclosed within a chamber comprising a polymer matrix wall.

6. The method of claim 5, wherein the polymer matrix wall extends from a first surface of the fluidic device to a second surface opposite of the first surface, thereby forming an interior of the chamber, wherein the interior of the chamber comprises the first cell and the second cell.

7. The method of claim 1, further comprising detecting a protein secreted by the first cell, the second cell, or the first cell and the second cell.

8. The method of claim 7, wherein the detecting comprises binding the protein to a protein affinity reagent coupled to a protein-capture surface.

9. The method of claim 8, wherein the protein-capture surface comprises a bead.

10. The method of claim 8, wherein in (d), the first cell and the second cell are selectively enclosed within a chamber comprising a polymer matrix wall, and wherein the protein-capture surface is disposed within the chamber.

11. The method of claim 7, wherein the detecting further comprises binding a protein detection antibody to the protein, and detecting the protein detection antibody.

12. The method of claim 1, wherein the introducing of the first cell in (a), the introducing of the second cell in (b), and the introducing of the polymer precursor in (c) are performed at the same time.

13. The method of claim 7, wherein the protein is secreted by the first cell, and wherein the protein is a cytokine or an immune active protein.

14. The method of claim 13, wherein the protein secreted by the first cell is an interferon-gamma (IFN-g), an interferon-alpha (IFN-a), an interleukin, a colony stimulating factor (CSF), a tumor necrosis factor (TNF), or an effector molecule.

15. The method of claim 5, further comprising introducing a plurality of protein-capture surfaces each coupled to a plurality of protein affinity reagents into the fluidic device;

co-enclosing at least a protein-capture surface of the plurality of protein-capture surfaces in the chamber, wherein the plurality of protein affinity reagents are configured to bind to a plurality of proteins secreted by the first cell; and measuring binding of the plurality of proteins secreted by the first cell to the plurality of protein affinity reagents, thereby detecting the plurality of proteins secreted by the first cell.

16. The method of claim 15, wherein each protein-capture surface of the plurality of protein-capture surfaces comprises a single type of protein affinity reagent of the plurality of protein affinity reagents.

17. The method of claim 1, further comprising detecting a surface protein expressed by the first cell, the second cell, or the first cell and the second cell.

18. The method of claim 17, wherein the detecting comprises binding an antibody to the surface protein, and detecting the antibody.

19. The method of claim 1, further comprising measuring a proliferative capacity, proliferation rate, activation status, cellular identity, purity, gene expression profile, transcriptome, epigenetic profile, sequence copy number, integrated viral copy number, plasmid copy number, gene copy number, or any combination thereof, of the first cell.

20. The method of claim 1, wherein the measuring of the cytotoxicity comprises incubating the first cell with a dye configured to generate an optical signal in response to a characteristic of a dead cell.

21. The method of claim 1, further comprising detecting activation of the first cell.

22. The method of claim 1, further comprising identifying the first cell.

23. The method of claim 22, wherein the identifying comprises detecting a surface protein expressed by the first cell, detecting a protein secreted by the first cell, detecting an mRNA transcript expressed by the first cell, or any combination thereof.

24. The method of claim 5, further comprising removing an additional cell that is not enclosed by the chamber from the fluidic device.

25. The method of claim 5, wherein the polymer matrix wall comprises a hydrogel.

26. The method of claim 5, further comprising at least partially degrading the chamber.

27. The method of claim 1, further comprising, prior to (d), determining a location of at least the first cell within the fluidic device.

28. The method of claim 27, wherein the determining of the location is performed using a detector.

29. The method of claim 1, wherein the virtual photomask is generated from a spatial light modulator (SLM).

30. The method of claim 1, wherein the first cell comprises an effector cell, and wherein the second cell comprises a target cell.

31. The method of claim 30, wherein the effector cell is an immune cell.

32. The method of claim 31, wherein the immune cell is a cytotoxic T lymphocyte, a regulatory T cell, a CD4+ T cell, a CD8+ T cell, a natural killer cell, an antigen-presenting cell, or a dendritic cell.

33. The method of claim 30, wherein the target cell comprises a cancer cell.

34. A method, comprising:

(a) introducing a first cell into a fluidic device;

(b) introducing a second cell into the fluidic device;

(c) introducing a polymer precursor into the fluidic device;

(d) using a virtual photomask to selectively apply light to the fluidic device to polymerize the polymer precursor, thereby selectively enclosing the first cell and the second cell in the fluidic device; and (e) detecting a protein secreted by the first cell, the second cell, or the first cell and the second cell, wherein the detecting comprises binding the protein to a protein affinity reagent coupled to a protein-capture surface, and wherein in (d), the first cell and the second cell are selectively enclosed within a chamber comprising a polymer matrix wall, and wherein the protein-capture surface is disposed within the chamber.

35. The method of claim 34, wherein the protein-capture surface comprises a bead.

36. The method of claim 34, wherein the protein is secreted by the first cell, and wherein the protein is a cytokine or an immune active protein.

37. A method, comprising:

(a) introducing a first cell into a fluidic device;

(b) introducing a second cell into the fluidic device;

(c) introducing a polymer precursor into the fluidic device;

(d) using a virtual photomask to selectively apply light to the fluidic device to polymerize the polymer precursor, thereby selectively enclosing the first cell and the second cell in the fluidic device; and (e) detecting a protein secreted by the first cell, wherein the protein secreted by the first cell is an interferon-gamma (IFN-g), an interferon-alpha (IFN-a), an interleukin, a colony stimulating factor (CSF), a tumor necrosis factor (TNF), or an effector molecule.

38. A method, comprising:

(a) introducing a first cell into a fluidic device;

(b) introducing a second cell into the fluidic device;

(c) introducing a polymer precursor into the fluidic device; and (d) using a virtual photomask to selectively apply light to the fluidic device to polymerize the polymer precursor, thereby selectively enclosing the first cell and the second cell in the fluidic device, wherein the introducing of the first cell in (a), the introducing of the second cell in (b), and the introducing of the polymer precursor in (c) are performed at the same time.

39. A method, comprising:

(a) introducing a first cell into a fluidic device;

(b) introducing a second cell into the fluidic device;

(c) introducing a polymer precursor into the fluidic device;

(d) introducing a plurality of protein-capture surfaces each coupled to a plurality of protein affinity reagents into the fluidic device, wherein the plurality of protein affinity reagents are configured to bind to a plurality of proteins secreted by the first cell;

(e) using a virtual photomask to selectively apply light to the fluidic device to polymerize the polymer precursor, thereby selectively co-enclosing (i) the first cell, (ii) the second cell, and (iii) at least a protein-capture surface of the plurality of protein-capture surfaces in a chamber comprising a polymer matrix wall in the fluidic device; and (f) measuring binding of the plurality of proteins secreted by the first cell to the plurality of protein affinity reagents, thereby detecting the plurality of proteins secreted by the first cell.

40. The method of claim 39, wherein each protein-capture surface of the plurality of protein-capture surfaces comprises a single type of protein affinity reagent of the plurality of protein affinity reagents.

41. A method, comprising:

(a) introducing a first cell into a fluidic device;

(b) introducing a second cell into the fluidic device;

(c) introducing a polymer precursor into the fluidic device;

(d) using a virtual photomask to selectively apply light to the fluidic device to polymerize the polymer precursor, thereby selectively enclosing the first cell and the second cell in the fluidic device; and (e) detecting activation of the first cell.

42. A method, comprising:

(a) introducing a first cell into a fluidic device;

(b) introducing a second cell into the fluidic device;

(c) introducing a polymer precursor into the fluidic device;

(d) using a virtual photomask to selectively apply light to the fluidic device to polymerize the polymer precursor, thereby selectively enclosing the first cell and the second cell in a chamber comprising a polymer matrix wall in the fluidic device; and (e) removing an additional cell that is not enclosed by the chamber from the fluidic device.

43. A method, comprising:

(a) introducing a first cell into a fluidic device;

(b) introducing a second cell into the fluidic device;

(c) introducing a polymer precursor into the fluidic device; and (d) using a virtual photomask to selectively apply light to the fluidic device to polymerize the polymer precursor, thereby selectively enclosing the first cell and the second cell in a chamber comprising a polymer matrix wall in the fluidic device, wherein the polymer matrix wall comprises a hydrogel.

44. A method, comprising:

(a) introducing a first cell into a fluidic device;

(b) introducing a second cell into the fluidic device;

(c) introducing a polymer precursor into the fluidic device; and (d) using a virtual photomask to selectively apply light to the fluidic device to polymerize the polymer precursor, thereby selectively enclosing the first cell and the second cell in a chamber comprising a polymer matrix wall in the fluidic device; and (e) at least partially degrading the chamber.

45. A method, comprising:

(a) introducing a first cell into a fluidic device;

(b) introducing a second cell into the fluidic device;

(c) introducing a polymer precursor into the fluidic device;

(d) determining a location of at least the first cell within the fluidic device; and (e) subsequent to (d), using a virtual photomask to selectively apply light to the fluidic device to polymerize the polymer precursor, thereby selectively enclosing the first cell and the second cell in the fluidic device.

46. The method of claim 45, wherein the determining of the location is performed using a detector.

* * * * *